United States Patent
Huitema et al.

(10) Patent No.: US 8,216,257 B2
(45) Date of Patent: *Jul. 10, 2012

(54) CLIP APPLIER CONFIGURED TO PREVENT CLIP FALLOUT

(75) Inventors: Thomas W. Huitema, Cincinnati, OH (US); Mark A. Davison, Mason, OH (US); Robert L. Koch, Jr., Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/111,400

(22) Filed: May 19, 2011

(65) Prior Publication Data

US 2011/0224696 A1    Sep. 15, 2011

Related U.S. Application Data

(63) Continuation of application No. 11/162,587, filed on Sep. 15, 2005, now Pat. No. 8,038,686, which is a continuation-in-part of application No. 10/907,763, filed on Apr. 14, 2005, now Pat. No. 7,297,149, and a continuation-in-part of application No. 10/907,764, filed on Apr. 14, 2005, now Pat. No. 7,288,098, and a continuation-in-part of application No. 10/907,765, filed on Apr. 14, 2005, now Pat. No. 7,261,724, and a continuation-in-part of application No. 10/907,766, filed on Apr. 14, 2005, now Pat. No. 7,686,820, and a continuation-in-part of application No. 10/907,768, filed on Apr. 14, 2005, now Pat. No. 7,731,724.

(51) Int. Cl.
*A61B 17/08* (2006.01)

(52) U.S. Cl. ...................................................... 606/142
(58) Field of Classification Search .................. 606/139, 606/142, 143, 151, 157, 158; 227/175.1–182.1
See application file for complete search history.

(56) References Cited

U.S. PATENT DOCUMENTS 2,968,041 A    1/1961    Skold
(Continued)

FOREIGN PATENT DOCUMENTS

DE    3490145    5/1985
(Continued)

OTHER PUBLICATIONS

Auto Suture Premium Surgiclip Titanium Disposable Automatic Clip Appliers, U.S. Surgical Corporation, Copyright 1988.
(Continued)

*Primary Examiner* — Kathleen Sonnett
(74) *Attorney, Agent, or Firm* — Nutter McClennen & Fish LLP

(57) ABSTRACT

A surgical clip applier and methods for applying surgical clips to a vessel, duct, shunt, etc., during a surgical procedure are provided. In one exemplary embodiment, a surgical clip applier is provided having a housing with a trigger movably coupled thereto and a shaft extending therefrom with opposed jaws formed on a distal end thereof. The trigger is adapted to advance a clip to position the clip between the jaws, and to move the jaws from an open position to a closed position to crimp the clip positioned therebetween. The surgical clip applier can include a variety of features to facilitate use of the device, including features to align a clip with the jaws, features to prevent unintentional migration of a clip, and features to prevent clip fallout during formation.

19 Claims, 45 Drawing Sheets

U.S. PATENT DOCUMENTS

| | | |
|---|---|---|
| 3,459,029 A | 8/1969 | Rosenfeld et al. |
| 4,038,987 A | 8/1977 | Komiya |
| 4,064,881 A | 12/1977 | Meredith |
| 4,080,820 A | 3/1978 | Allen |
| 4,152,920 A | 5/1979 | Green |
| 4,188,953 A | 2/1980 | Klieman et al. |
| 4,242,902 A | 1/1981 | Green |
| 4,296,751 A | 10/1981 | Blake, III et al. |
| 4,298,072 A | 11/1981 | Baker et al. |
| 4,372,316 A | 2/1983 | Blake, III et al. |
| 4,408,603 A | 10/1983 | Blake, III et al. |
| 4,448,193 A | 5/1984 | Ivanov |
| 4,449,530 A | 5/1984 | Bendel et al. |
| 4,452,376 A | 6/1984 | Klieman et al. |
| 4,513,746 A | 4/1985 | Aranyi et al. |
| 4,522,207 A | 6/1985 | Klieman et al. |
| 4,532,925 A | 8/1985 | Blake, III |
| 4,556,058 A | 12/1985 | Green |
| 4,557,263 A | 12/1985 | Green |
| 4,576,165 A | 3/1986 | Green et al. |
| 4,588,580 A | 5/1986 | Gale et al. |
| 4,590,937 A | 5/1986 | Deniega |
| 4,611,595 A | 9/1986 | Klieman et al. |
| 4,616,650 A | 10/1986 | Green et al. |
| 4,651,737 A | 3/1987 | Deniega |
| 4,662,374 A | 5/1987 | Blake, III |
| 4,674,504 A | 6/1987 | Klieman et al. |
| 4,676,504 A | 6/1987 | Ponza |
| 4,702,274 A | 10/1987 | Kramer |
| 4,712,549 A | 12/1987 | Peters et al. |
| 4,741,336 A | 5/1988 | Failla et al. |
| 4,799,481 A | 1/1989 | Transue et al. |
| 4,834,096 A | 5/1989 | Oh et al. |
| 4,844,066 A | 7/1989 | Stein |
| 4,850,355 A | 7/1989 | Brooks et al. |
| 4,976,722 A | 12/1990 | Failla |
| 4,979,950 A | 12/1990 | Transue et al. |
| 5,009,661 A | 4/1991 | Michelson |
| 5,012,666 A | 5/1991 | Chen et al. |
| 5,030,226 A | 7/1991 | Green et al. |
| 5,047,038 A | 9/1991 | Peters et al. |
| 5,049,152 A | 9/1991 | Simon et al. |
| 5,062,846 A | 11/1991 | Oh et al. |
| 5,084,057 A | 1/1992 | Green et al. |
| 5,086,901 A | 2/1992 | Petronis et al. |
| 5,100,416 A | 3/1992 | Oh et al. |
| 5,100,420 A | 3/1992 | Green et al. |
| 5,104,395 A | 4/1992 | Thornton et al. |
| 5,112,343 A | 5/1992 | Thornton |
| 5,116,349 A | 5/1992 | Aranyi |
| 5,127,730 A | 7/1992 | Brelje et al. |
| 5,129,885 A | 7/1992 | Green et al. |
| 5,156,609 A | 10/1992 | Nakao et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,190,203 A | 3/1993 | Rodak |
| 5,192,288 A | 3/1993 | Thompson et al. |
| 5,197,970 A | 3/1993 | Green et al. |
| 5,201,746 A | 4/1993 | Shichman |
| 5,222,961 A | 6/1993 | Nakao et al. |
| 5,232,450 A | 8/1993 | Green et al. |
| 5,246,450 A | 9/1993 | Thornton et al. |
| 5,269,792 A | 12/1993 | Kovac et al. |
| 5,270,171 A | 12/1993 | Cercek et al. |
| 5,282,807 A | 2/1994 | Knoepfler |
| 5,282,808 A | 2/1994 | Kovac et al. |
| 5,286,255 A | 2/1994 | Weber |
| 5,300,081 A | 4/1994 | Young et al. |
| 5,306,149 A | 4/1994 | Schmid et al. |
| 5,336,232 A | 8/1994 | Green et al. |
| 5,354,304 A | 10/1994 | Allen et al. |
| 5,358,506 A | 10/1994 | Green et al. |
| 5,366,458 A | 11/1994 | Korthoff et al. |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,381 A | 3/1995 | Green et al. |
| 5,403,326 A | 4/1995 | Harrison et al. |
| 5,403,327 A | 4/1995 | Thornton et al. |
| 5,409,498 A | 4/1995 | Braddock et al. |
| 5,423,835 A | 6/1995 | Green et al. |
| 5,431,667 A | 7/1995 | Thompson et al. |
| 5,431,668 A | 7/1995 | Burbank, III et al. |
| 5,431,669 A | 7/1995 | Thompson et al. |
| 5,433,721 A | 7/1995 | Hooven et al. |
| 5,434,081 A | 7/1995 | Maekawa |
| 5,439,156 A | 8/1995 | Grant et al. |
| 5,468,250 A | 11/1995 | Paraschac et al. |
| 5,470,007 A | 11/1995 | Plyley et al. |
| 5,474,732 A | 12/1995 | Korthoff et al. |
| 5,484,095 A | 1/1996 | Green et al. |
| 5,484,451 A | 1/1996 | Akopov et al. |
| 5,496,333 A | 3/1996 | Sackier et al. |
| 5,497,933 A | 3/1996 | DeFonzo et al. |
| 5,499,998 A | 3/1996 | Meade |
| 5,501,693 A | 3/1996 | Gravener |
| 5,509,920 A | 4/1996 | Phillips et al. |
| 5,514,149 A | 5/1996 | Green et al. |
| 5,527,318 A | 6/1996 | McGarry |
| 5,527,319 A | 6/1996 | Green et al. |
| 5,527,320 A | 6/1996 | Carruthers et al. |
| 5,547,117 A | 8/1996 | Hamblin et al. |
| 5,547,474 A | 8/1996 | Kloeckl et al. |
| 5,562,694 A | 10/1996 | Sauer et al. |
| 5,575,206 A | 11/1996 | Szyszko |
| 5,575,806 A | 11/1996 | Nakao et al. |
| 5,580,067 A | 12/1996 | Hamblin et al. |
| 5,582,615 A | 12/1996 | Foshee et al. |
| 5,582,617 A | 12/1996 | Klieman et al. |
| 5,591,178 A | 1/1997 | Green et al. |
| 5,601,224 A | 2/1997 | Bishop et al. |
| 5,601,573 A | 2/1997 | Fogelberg et al. |
| 5,605,272 A | 2/1997 | Witt et al. |
| 5,607,273 A | 3/1997 | Kecmer et al. |
| 5,607,436 A | 3/1997 | Pratt et al. |
| 5,618,291 A | 4/1997 | Thompson et al. |
| 5,624,452 A | 4/1997 | Yates |
| 5,625,592 A | 4/1997 | Shinozaki |
| 5,626,585 A | 5/1997 | Mittelstadt et al. |
| 5,626,586 A | 5/1997 | Pistl et al. |
| 5,630,539 A | 5/1997 | Plyley et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,667,517 A | 9/1997 | Hooven |
| 5,673,841 A | 10/1997 | Schulze et al. |
| 5,681,330 A | 10/1997 | Hughett et al. |
| 5,695,502 A | 12/1997 | Pier et al. |
| 5,697,543 A | 12/1997 | Burdorff |
| 5,700,270 A | 12/1997 | Peyser et al. |
| 5,700,271 A | 12/1997 | Whitfield et al. |
| 5,706,824 A | 1/1998 | Whittier |
| 5,713,911 A | 2/1998 | Racenet et al. |
| 5,720,756 A | 2/1998 | Green et al. |
| 5,725,537 A | 3/1998 | Green et al. |
| 5,725,538 A | 3/1998 | Green et al. |
| 5,749,881 A | 5/1998 | Sackier et al. |
| 5,755,726 A | 5/1998 | Pratt et al. |
| 5,772,673 A | 6/1998 | Cuny et al. |
| 5,776,147 A | 7/1998 | Dolendo |
| 5,792,149 A | 8/1998 | Sherts et al. |
| 5,792,150 A | 8/1998 | Pratt et al. |
| 5,792,165 A | 8/1998 | Klieman et al. |
| 5,794,834 A | 8/1998 | Hamblin et al. |
| 5,830,221 A | 11/1998 | Stein et al. |
| 5,833,695 A | 11/1998 | Yoon |
| 5,833,696 A | 11/1998 | Whitfield et al. |
| 5,833,881 A | 11/1998 | Roe |
| 5,843,097 A | 12/1998 | Mayenberger et al. |
| 5,843,101 A | 12/1998 | Fry |
| 5,849,019 A | 12/1998 | Yoon |
| 5,855,311 A | 1/1999 | Hamblin et al. |
| 5,868,759 A | 2/1999 | Peyser et al. |
| 5,868,761 A | 2/1999 | Nicholas et al. |

| | | | | | | |
|---|---|---|---|---|---|---|
| 5,869,435 | A | 2/1999 | Kelly et al. | 2006/0235439 A1 | 10/2006 | Molitor et al. |
| 5,895,394 | A | 4/1999 | Kienzle et al. | 2006/0235440 A1 | 10/2006 | Huitema et al. |
| 5,902,312 | A | 5/1999 | Frater et al. | 2006/0235441 A1 | 10/2006 | Huitema et al. |
| 5,904,693 | A | 5/1999 | Dicesare et al. | 2006/0235442 A1 | 10/2006 | Huitema |
| 5,928,251 | A | 7/1999 | Aranyi et al. | 2006/0235443 A1 | 10/2006 | Huitema et al. |
| 5,938,667 | A | 8/1999 | Peyser et al. | 2006/0235444 A1 | 10/2006 | Huitema et al. |
| 5,941,439 | A | 8/1999 | Kammerer et al. | 2008/0004639 A1 | 1/2008 | Huitema et al. |
| 5,972,003 | A | 10/1999 | Rousseau et al. | 2008/0015615 A1 | 1/2008 | Molitor et al. |
| 5,993,465 | A | 11/1999 | Shipp et al. | 2008/0027465 A1 | 1/2008 | Vitali et al. |
| RE36,720 | E | 5/2000 | Green et al. | 2008/0027466 A1 | 1/2008 | Vitali et al. |
| 6,059,799 | A | 5/2000 | Aranyi et al. | 2010/0185215 A1 | 7/2010 | Huitema et al. |
| 6,063,097 | A | 5/2000 | Oi et al. | 2010/0249804 A1 | 9/2010 | Huitema |
| 6,066,145 | A | 5/2000 | Wurster | 2011/0087241 A1 | 4/2011 | Nguyen |
| 6,096,058 | A | 8/2000 | Boche | 2011/0087243 A1 | 4/2011 | Nguyen et al. |
| 6,139,555 | A | 10/2000 | Hart et al. | 2011/0144440 A1 | 6/2011 | Cropper et al. |
| 6,152,920 | A | 11/2000 | Thompson et al. | 2011/0218553 A1 | 9/2011 | Huitema et al. |
| 6,217,590 | B1 | 4/2001 | Levinson | 2011/0218555 A1 | 9/2011 | Huitema |
| 6,228,097 | B1 | 5/2001 | Levinson et al. | 2011/0218556 A1 | 9/2011 | Nguyen et al. |
| 6,241,740 | B1 | 6/2001 | Davis et al. | | | |
| 6,277,131 | B1 | 8/2001 | Kalikow | | | |
| 6,306,149 | B1 | 10/2001 | Meade | | | |
| 6,306,150 | B1 | 10/2001 | Levinson | | | |
| 6,423,079 | B1 | 7/2002 | Blake, III | | | |
| 6,440,144 | B1 | 8/2002 | Bacher | | | |
| 6,458,142 | B1 | 10/2002 | Faller et al. | | | |
| 6,460,749 | B1 | 10/2002 | Levinson et al. | | | |
| 6,462,345 | B1 | 10/2002 | Simon et al. | | | |
| 6,507,400 | B1 | 1/2003 | Pina et al. | | | |
| 6,533,157 | B1 | 3/2003 | Whitman | | | |
| 6,537,289 | B1 | 3/2003 | Kayan et al. | | | |
| 6,544,271 | B1 | 4/2003 | Adams et al. | | | |
| 6,548,142 | B1 | 4/2003 | Kar et al. | | | |
| 6,548,796 | B1 | 4/2003 | Silvermintz et al. | | | |
| 6,549,275 | B1 | 4/2003 | Cabuz et al. | | | |
| 6,569,171 | B2 | 5/2003 | DeGuillebon et al. | | | |
| 6,589,792 | B1 | 7/2003 | Malachowski | | | |
| 6,597,438 | B1 | 7/2003 | Cabuz et al. | | | |
| 6,610,073 | B1 | 8/2003 | Levinson | | | |
| 6,646,742 | B1 | 11/2003 | Gangstead et al. | | | |
| 6,673,083 | B1 | 1/2004 | Kayan et al. | | | |
| 6,687,052 | B1 | 2/2004 | Wilson et al. | | | |
| 6,695,854 | B1 | 2/2004 | Kayan et al. | | | |
| 6,727,071 | B1 | 4/2004 | Dunlay et al. | | | |
| 6,752,823 | B2 | 6/2004 | Prestel | | | |
| 6,869,435 | B2 | 3/2005 | Blake, III | | | |
| 6,911,033 | B2 | 6/2005 | de Guillebon et al. | | | |
| 7,052,504 | B2 | 5/2006 | Hughett | | | |
| 7,211,092 | B2 | 5/2007 | Hughett | | | |
| 7,261,724 | B2 | 8/2007 | Molitor et al. | | | |
| 7,288,098 | B2 | 10/2007 | Huitema et al. | | | |
| 7,297,149 | B2 | 11/2007 | Vitali et al. | | | |
| 7,686,820 | B2 | 3/2010 | Huitema et al. | | | |
| 7,731,641 | B1 | 6/2010 | Chen | | | |
| 7,731,724 | B2 | 6/2010 | Huitema et al. | | | |
| 7,740,641 | B2 | 6/2010 | Huitema | | | |
| 8,038,686 | B2 * | 10/2011 | Huitema et al. ............. 606/142 | | | |
| 8,075,571 | B2 | 12/2011 | Vitali et al. | | | |
| 2002/0099388 | A1 | 7/2002 | Mayenberger | | | |
| 2002/0123767 | A1 | 9/2002 | Prestel | | | |
| 2002/0128668 | A1 | 9/2002 | Manetakis et al. | | | |
| 2002/0138086 | A1 | 9/2002 | Sixto et al. | | | |
| 2002/0177863 | A1 | 11/2002 | Mandel et al. | | | |
| 2002/0198541 | A1 | 12/2002 | Smith et al. | | | |
| 2003/0014060 | A1 | 1/2003 | Wilson et al. | | | |
| 2003/0023249 | A1 | 1/2003 | Manetakis | | | |
| 2003/0040756 | A1 | 2/2003 | Field | | | |
| 2003/0040759 | A1 | 2/2003 | de Guillebon et al. | | | |
| 2003/0065358 | A1 | 4/2003 | Frecker et al. | | | |
| 2003/0069474 | A1 | 4/2003 | Couvillon | | | |
| 2003/0135224 | A1 | 7/2003 | Blake | | | |
| 2003/0191478 | A1 | 10/2003 | Kortenbach et al. | | | |
| 2004/0087979 | A1 | 5/2004 | Field et al. | | | |
| 2004/0097970 | A1 | 5/2004 | Hughett | | | |
| 2004/0097971 | A1 | 5/2004 | Hughett | | | |
| 2004/0097972 | A1 | 5/2004 | Shipp et al. | | | |
| 2004/0153107 | A1 | 8/2004 | Kayan et al. | | | |
| 2004/0167545 | A1 | 8/2004 | Sadler et al. | | | |
| 2006/0235437 | A1 | 10/2006 | Vitali et al. | | | |
| 2006/0235438 | A1 | 10/2006 | Huitema et al. | | | |

FOREIGN PATENT DOCUMENTS

| | | |
|---|---|---|
| DE | 3152411 | 8/1986 |
| DE | 4015562 A1 | 11/1991 |
| DE | 4303544 A1 | 9/1993 |
| DE | 19534320 C1 | 2/1997 |
| DE | 19537299 A1 | 4/1997 |
| DE | 19643073 A1 | 4/1997 |
| DE | 19647354 A1 | 5/1998 |
| DE | 1993372 | 2/2001 |
| DE | 19933672 A1 | 2/2001 |
| EP | 90815 A1 | 10/1983 |
| EP | 152226 A1 | 8/1985 |
| EP | 409569 A1 | 1/1991 |
| EP | 500353 A1 | 8/1992 |
| EP | 0510826 | 10/1992 |
| EP | 0671148 A2 | 9/1995 |
| EP | 674876 A2 | 10/1995 |
| EP | 681810 A2 | 11/1995 |
| EP | 0704190 | 3/1996 |
| EP | 0769274 | 4/1997 |
| EP | 832605 A1 | 4/1998 |
| EP | 834286 A1 | 4/1998 |
| EP | 908152 A1 | 4/1999 |
| EP | 1317906 A1 | 6/2003 |
| EP | 1405601 A1 | 4/2004 |
| EP | 1522264 A1 | 4/2005 |
| EP | 1537883 | 6/2005 |
| EP | 1764045 A1 | 3/2007 |
| FR | 900376 A | 6/1945 |
| SU | 620263 A1 | 8/1978 |
| SU | 1560125 A1 | 4/1990 |
| WO | WO-8910094 A1 | 11/1989 |
| WO | WO-9608203 A1 | 3/1996 |
| WO | WO-9902090 A1 | 1/1999 |
| WO | WO-0042922 A1 | 7/2000 |
| WO | WO-0126705 A2 | 4/2001 |
| WO | WO-0156455 A2 | 8/2001 |
| WO | WO-0215797 | 2/2002 |
| WO | WO-0228268 | 4/2002 |
| WO | WO-03005878 | 1/2003 |
| WO | WO-03005911 A1 | 1/2003 |
| WO | WO-2004050971 A2 | 6/2004 |

OTHER PUBLICATIONS

European Search Report for 06252080.4, dated Dec. 27, 2006 (6 Pages).
European Search Report for 0625479.3, dated Feb. 16, 2009 (8 Pages).
European Search Report for 06254793.0, dated Oct. 1, 2009. (6 Pages).
European Search Report for 06254800.3, dated Jan. 15, 2007 (6 Pages).
European Search Report for 06254801.1, dated Jan. 17, 2007 (6 Pages).
European Search Report for 10179717.3, dated Nov. 19, 2010 (5 Pages).
European Search Report for 10179743.9, dated Feb. 7, 2011 (10 Pages).

International Search Report for PCT/US 02/21609, dated Nov. 21, 2002 (3 Pages).
New Surgical Procedure for Indirect Hernias, Innovative Surgical Device, Inc.
Notice of Opposition filed in EP 1,764,044 on Feb. 4, 2010.
Partial European Search Report for 06252083.8, dated Dec. 27, 2006 (4 Pages).
Partial European Search Report for 10179741.3, dated Nov. 5, 2010 (6 Pages).
Singapore Supplementary Search Report for 200602116-6, dated Feb. 9, 2009. (6 pages).
Singapore Written Opinion for 0806148-3, dated Oct. 19 2009. (5 pages).

* cited by examiner

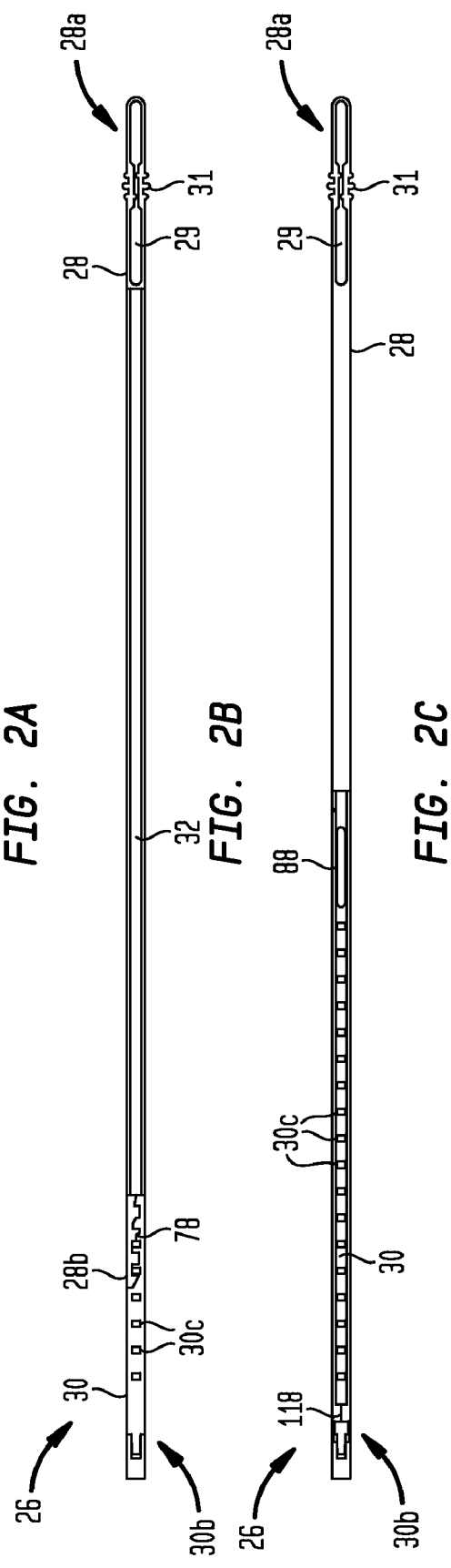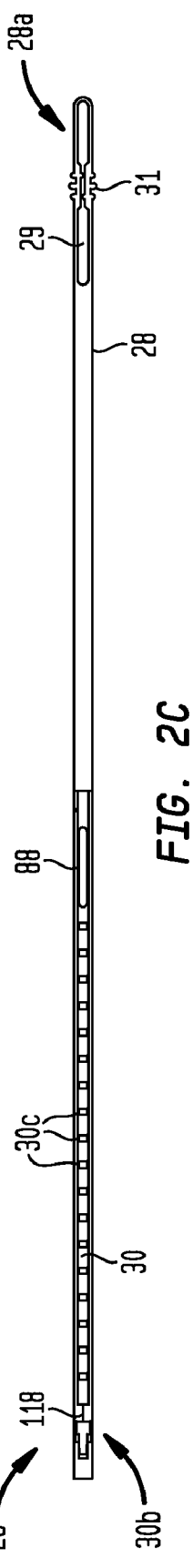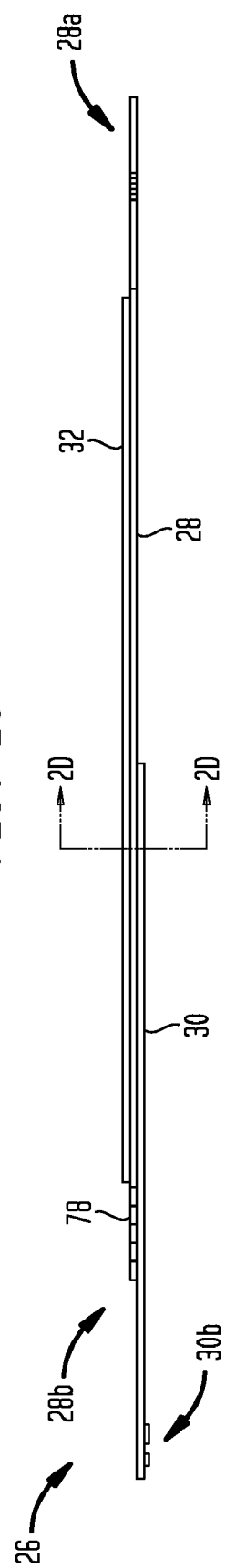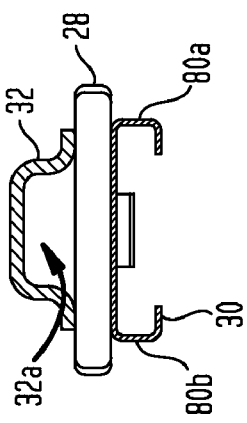

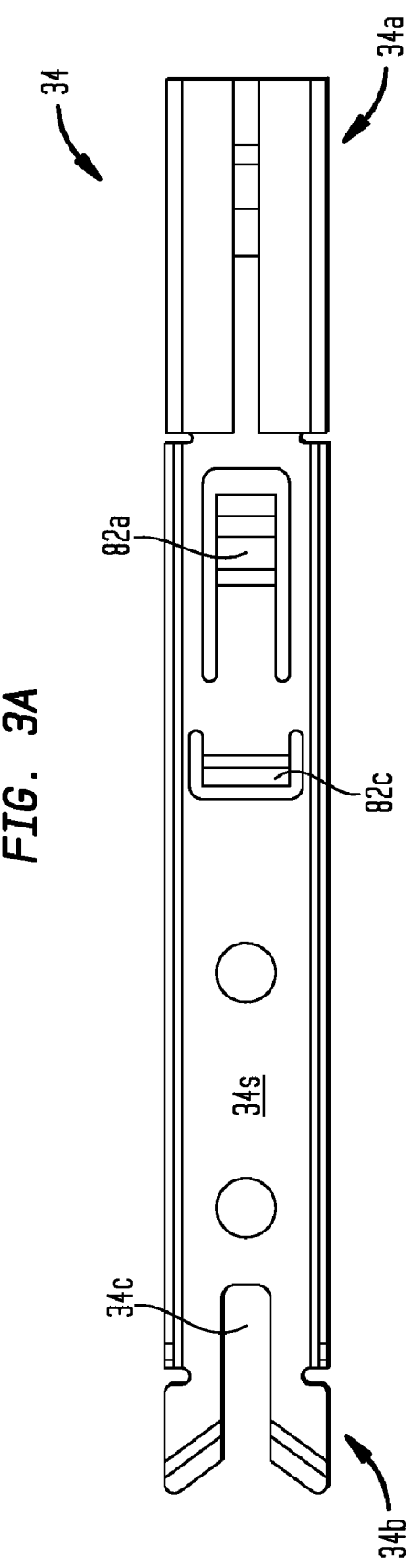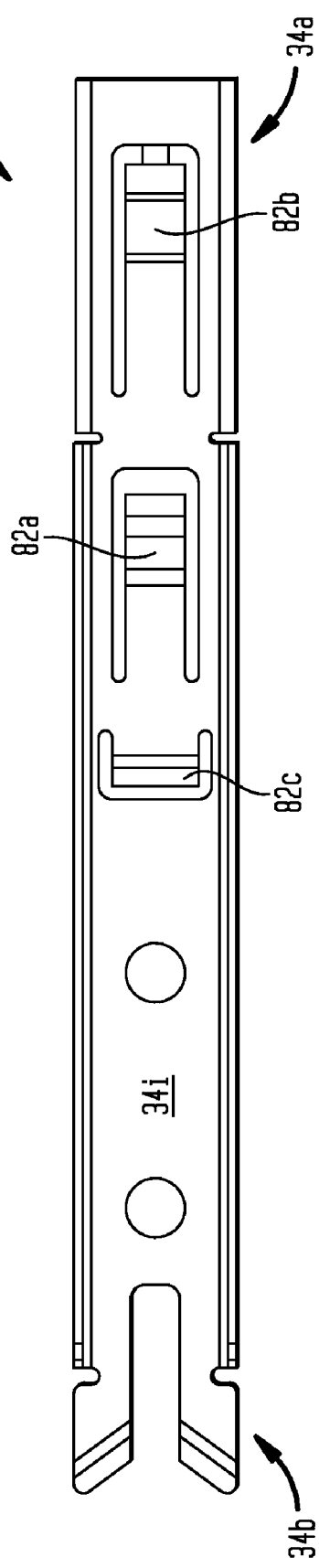

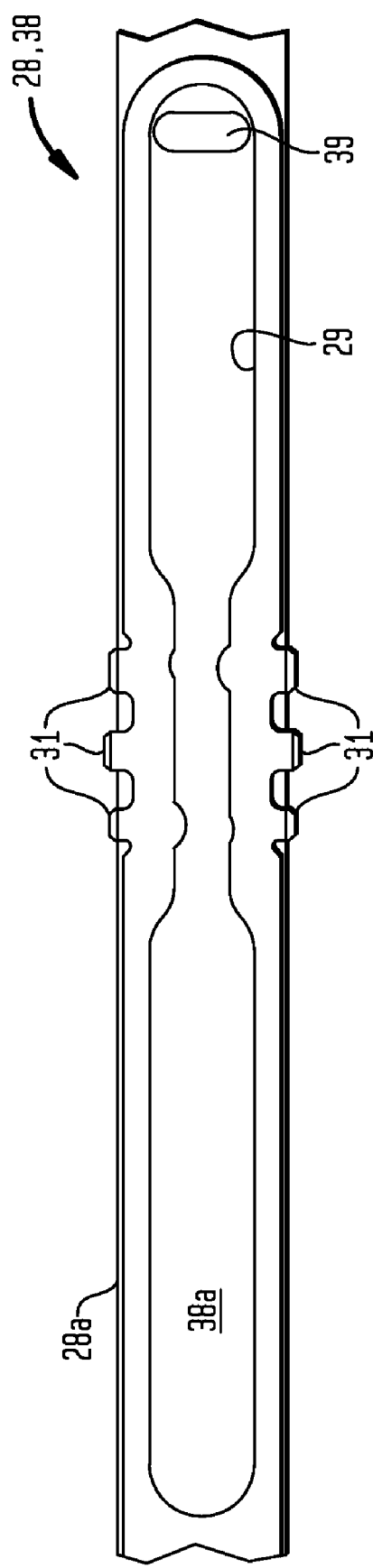
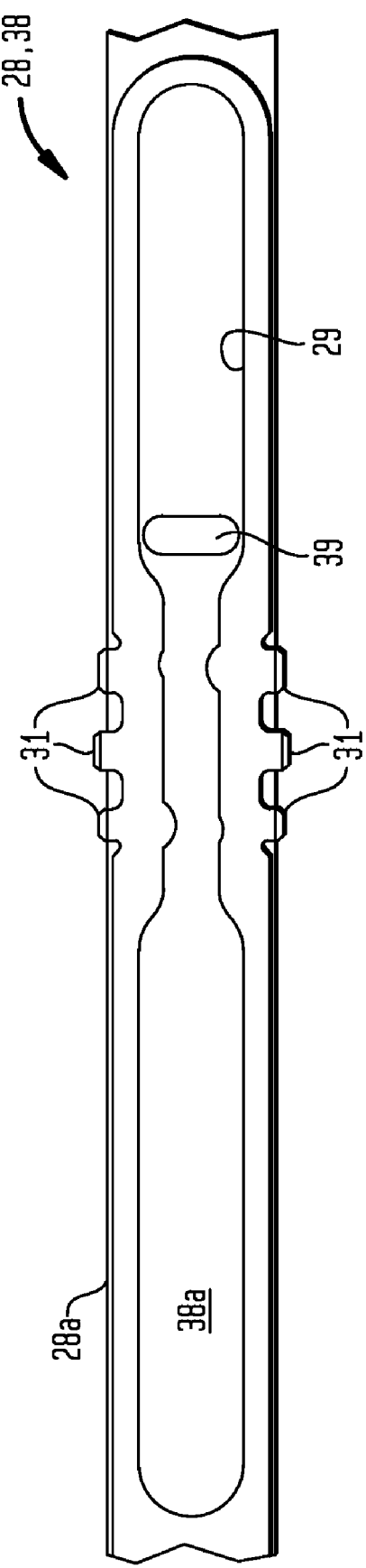

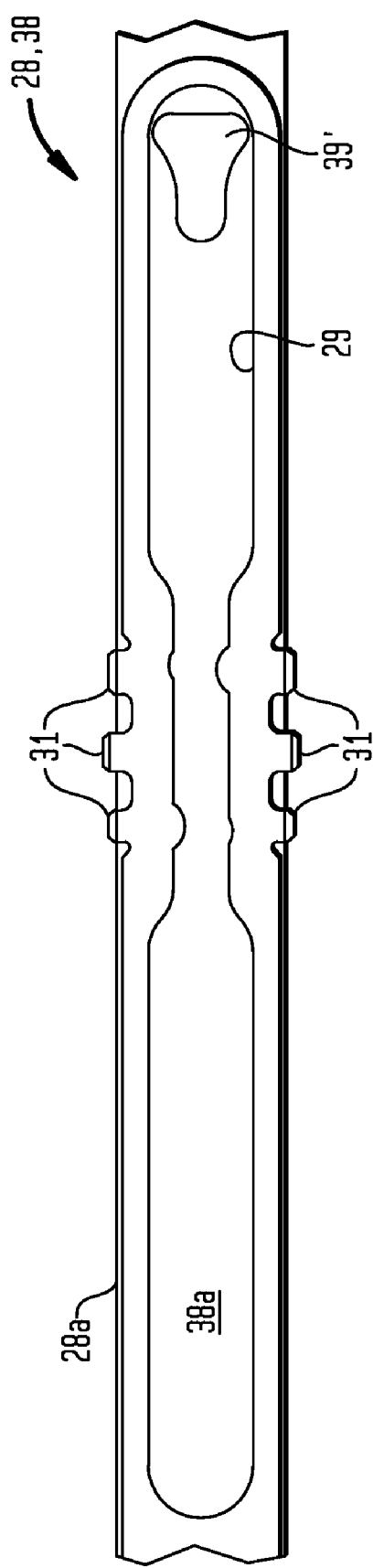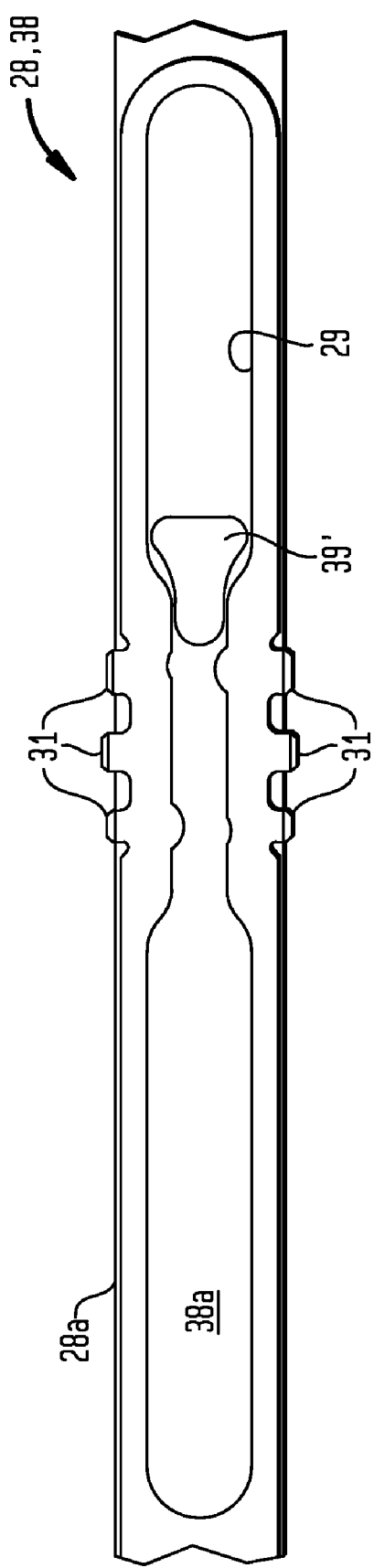

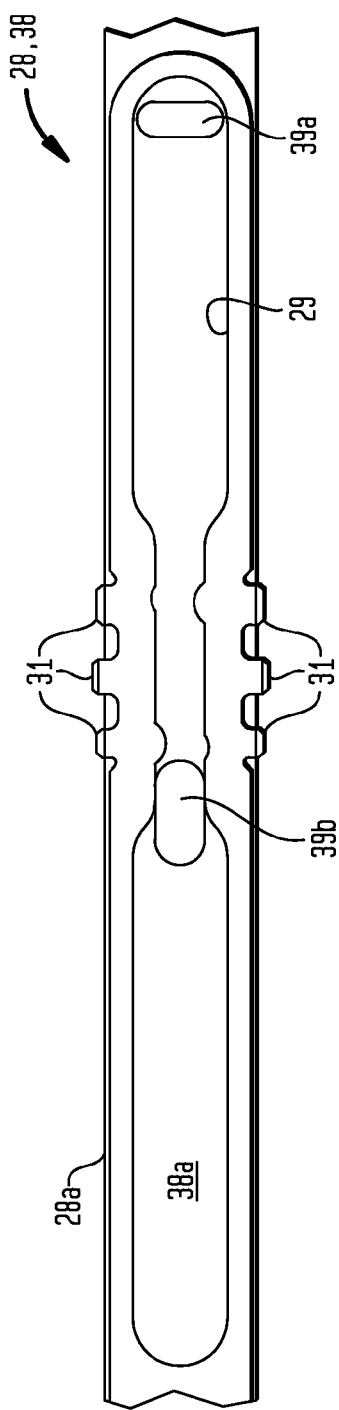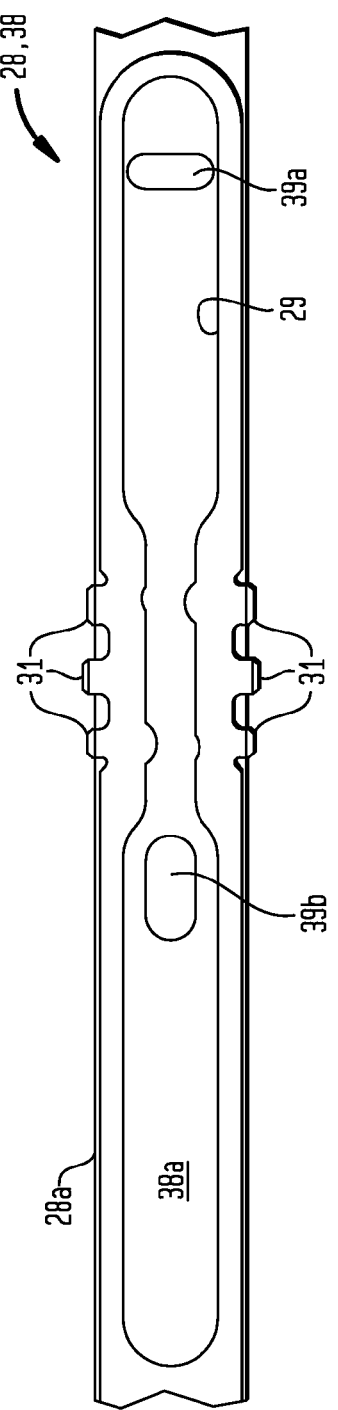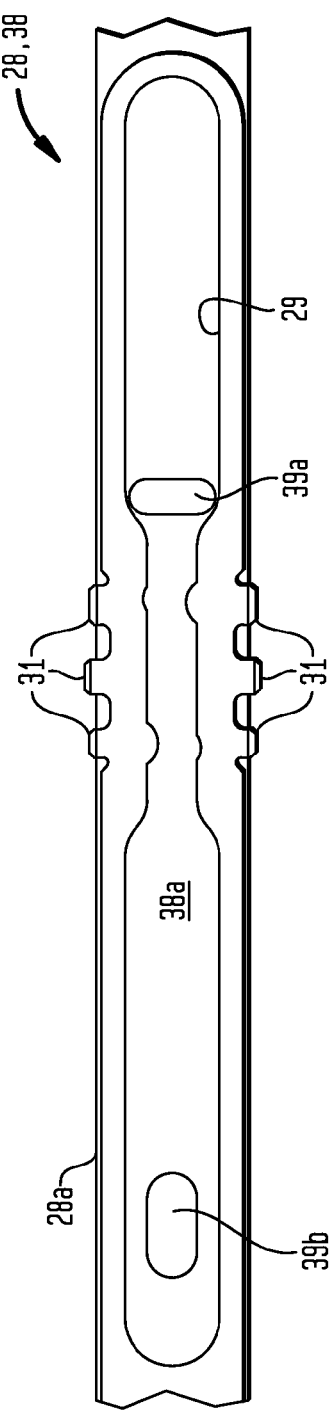

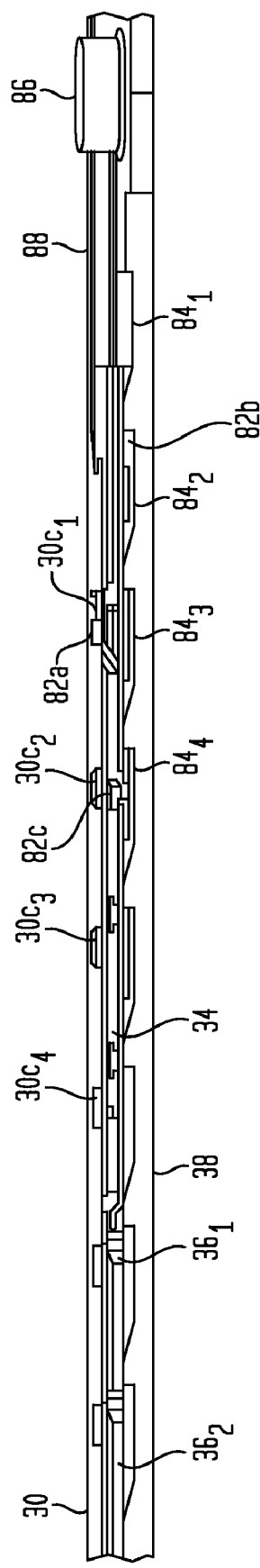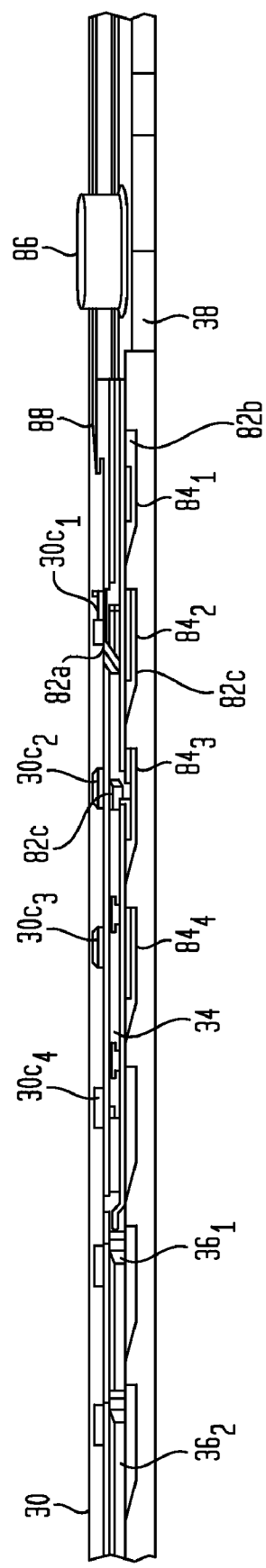

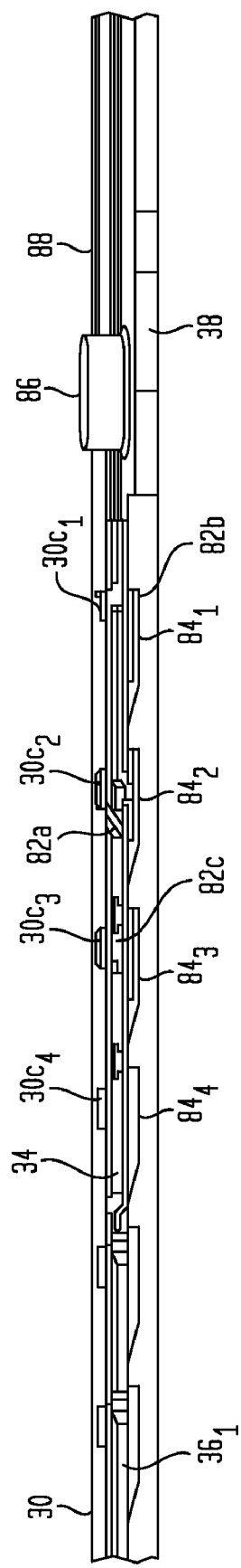
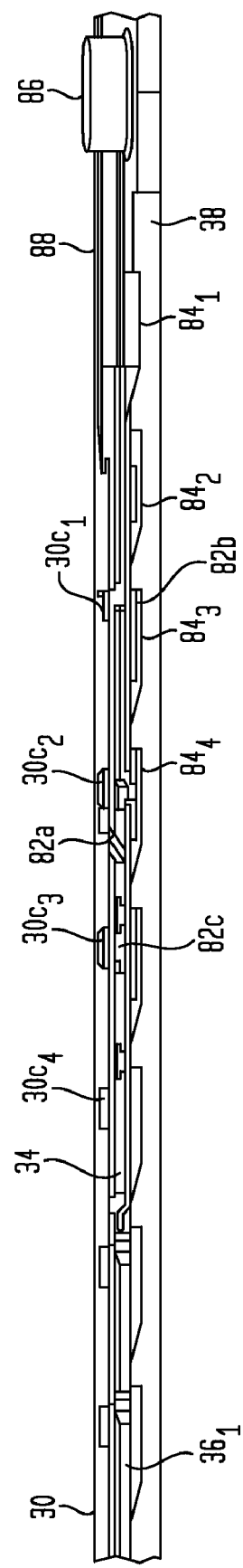
FIG. 6C
FIG. 6D

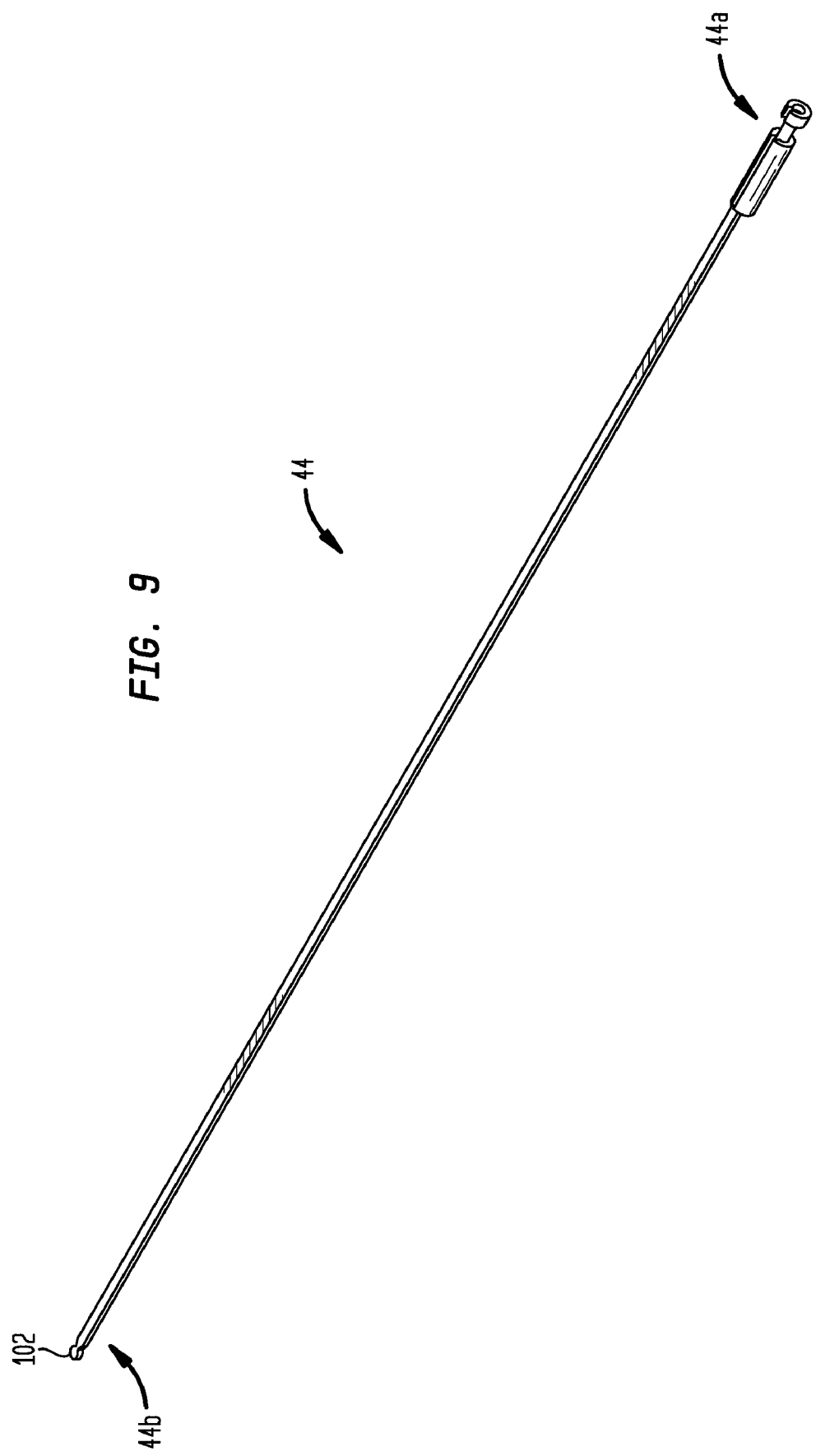

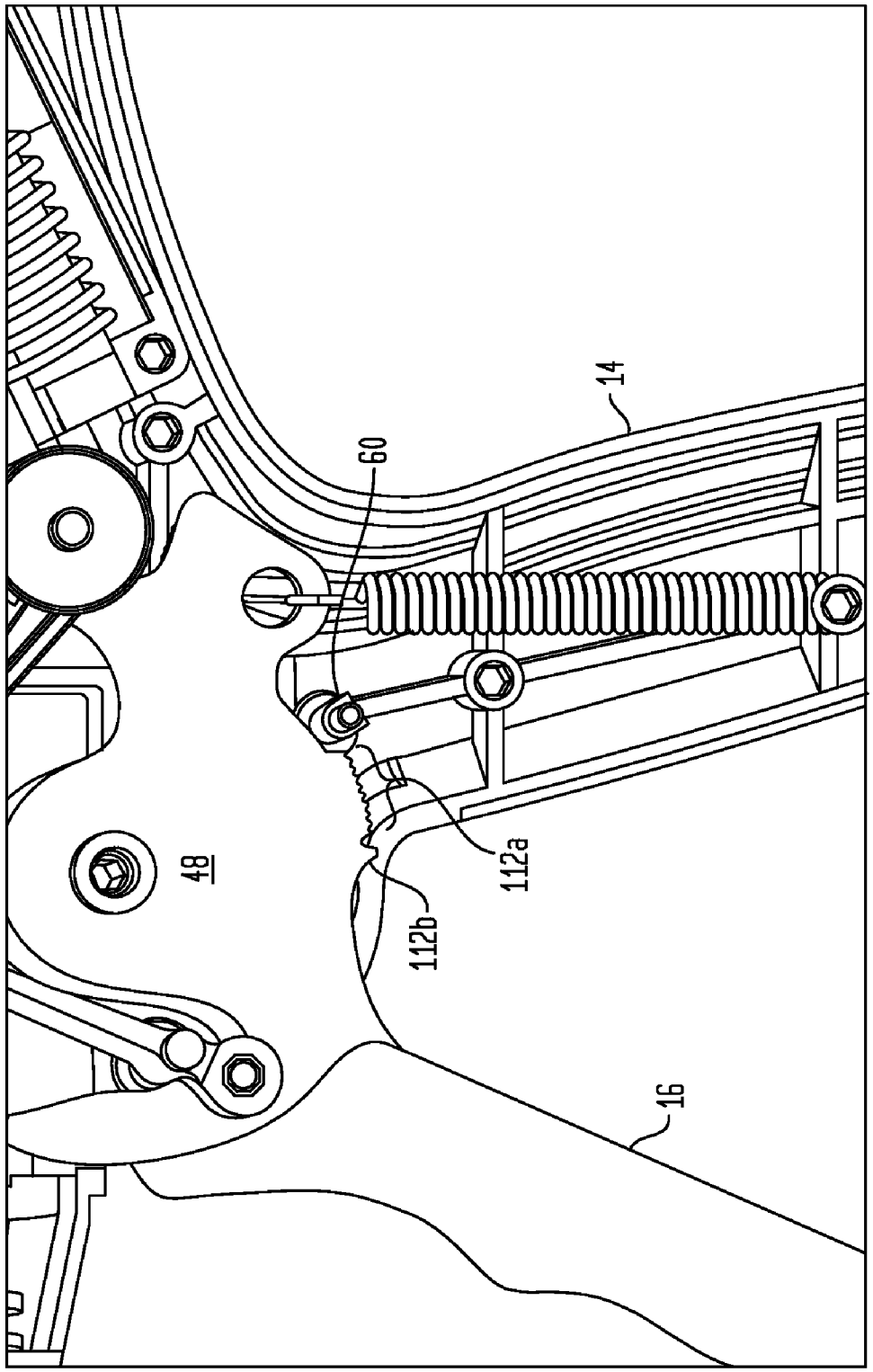

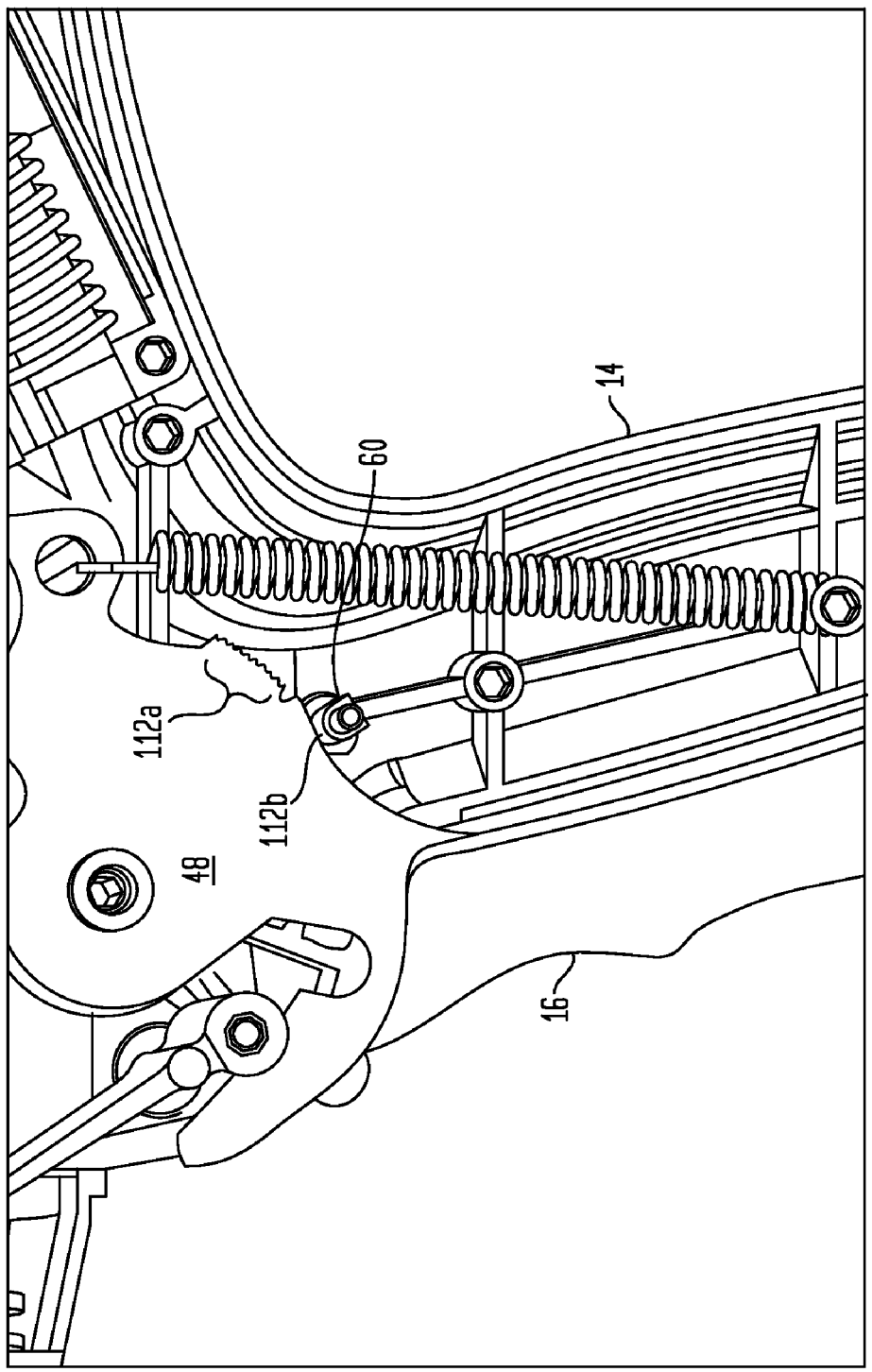

CLIP APPLIER CONFIGURED TO PREVENT CLIP FALLOUT

CROSS-REFERENCE TO RELATED APPLICATIONS

The present application is a continuation of U.S. patent application Ser. No. 11/162,587 (now U.S. Pat. No. 8,038, 686) filed on Sep. 15, 2005 entitled "Clip Applier Configured to Prevent Clip Fallout," which is a continuation-in-part of U.S. patent application Ser. No. 10/907,763 (now U.S. Pat. No. 7,297,149) filed on Apr. 14, 2005 and entitled "Surgical Clip Applier Methods," U.S. patent application Ser. No. 10/907,764 (now U.S. Pat. No. 7,288,098) filed on Apr. 14, 2005 and entitled "Force Limiting Mechanism For Medical Instrument," U.S. patent application Ser. No. 10/907,765 (now U.S. Pat. No. 7,261,724) filed on Apr. 14, 2005 and entitled "Surgical Clip Advancement Mechanism," U.S. patent application Ser. No. 10/907,766 (now U.S. Pat. No. 7,686,820) filed on Apr. 14, 2005 and entitled "Surgical Clip Applier Ratchet Mechanism," and U.S. patent application Ser. No. 10/907,768 (now U.S. Pat. No. 7,731,724) filed on Apr. 14, 2005 and entitled "Surgical Clip Advancement And Alignment Mechanism." These references are hereby incorporated by reference in their entirety.

FIELD OF THE INVENTION

The present invention relates broadly to surgical devices, and in particular to methods and devices for applying surgical clips to ducts, vessels, shunts, etc.

BACKGROUND OF THE INVENTION

In recent years surgery has markedly advanced through the performance of laparoscopic and endoscopic surgical procedures such as cholecystectomies, gastrostomies, appendectomies, and hernia repair. These procedures are accomplished through a trocar assembly, which is a surgical instrument used to puncture a body cavity. The trocar typically contains a sharpened obturator tip and a trocar tube or cannula. The trocar cannula is inserted into the skin to access the body cavity, by using the obturator tip to penetrate the skin. After penetration, the obturator is removed and the trocar cannula remains in the body. It is through this cannula that surgical instruments are placed.

One surgical instrument that is commonly used with a trocar cannula is a surgical clip applier for ligating a blood vessel, a duct, shunt, or a portion of body tissue during surgery. Most clip appliers typically have a handle with an elongate shaft having a pair of movable opposed jaws formed on an end thereof for holding and forming a ligation clip therebetween. The jaws are positioned around the vessel or duct, and the clip is crushed or formed on the vessel by the closing of the jaws.

In many of the prior art clip appliers, the feeding and forming mechanisms require precise timing and coordinated movement of components to operate. This need for precise timing and control has resulted in the need for complex mechanical designs, thereby increasing the cost of the clip appliers. Many prior art clip appliers also use a spring-loaded clip advancing assembly to advance one or more clips through the shaft of the device. As a result, the jaws must contain a mechanism for preventing accidental projection of the clip from the device before the clip is formed. Other drawbacks of current clip appliers include the inability to handle an overload applied to the jaws by the trigger under a variety of conditions. Many devices require full closure of the jaws, which can result in overload on the jaws when the vessel or duct positioned therebetween is too large to allow full closure, or when a foreign object is positioned between the jaws.

Accordingly, there remains a need for improved methods and devices for applying surgical clips to vessels, ducts, shunts, etc.

SUMMARY OF THE INVENTION

The present invention provides method and devices for applying a surgical clip to a vessel, duct, shunt, etc. In one exemplary embodiment, a surgical clip applier is provided having a housing with a trigger movably coupled thereto and an elongate shaft extending therefrom with opposed jaws formed on a distal end thereof. The trigger is adapted to advance a clip to position the clip between the jaws, and to move the jaws from an open position to a closed position to crimp the clip positioned therebetween.

The surgical clip applier can have a variety of configurations, and it can include a variety of features to facilitate advancement and formation of a surgical clip. In one embodiment, the surgical clip applier can include a feeder shoe that is slidably disposed within the elongate shaft and that is adapted to drive at least one surgical clip through the elongate shaft. In an exemplary embodiment, the feeder shoe can be adapted to move only in a distal direction, such that proximal movement of the feeder shoe is substantially prevented. The elongate shaft can also include a clip track disposed therein and adapted to seat at least one surgical clip. The feeder shoe can be slidably disposed within the clip track.

A variety of techniques can be used to facilitate distal movement and prevent proximal movement of the feeder shoe. In one exemplary embodiment, the feeder shoe can include a tang adapted to engage the clip track to prevent proximal movement of the feeder shoe within the clip track, yet allow distal movement of the feeder shoe within the clip track. The clip track can include several openings formed therein for receiving the tang to prevent proximal movement of the feeder shoe within the clip track. In another exemplary embodiment, the feeder shoe can include a tang and the feed bar can include several detents formed therein and adapted to engage the tang to move the feeder shoe distally when the feed bar is moved distally.

In another embodiment, the elongate shaft can include a feed bar slidably disposed therein and coupled to the trigger such that movement of the trigger toward a closed position is adapted to advance the feed bar distally thereby advancing the feeder shoe distally. By way of non-limiting example, the feed bar can be coupled to the trigger by a trigger insert that is mated to the trigger, and by a link that extends between the trigger insert and the proximal end of the feed bar. The proximal end of the feed bar can include a coupler that is adapted to receive a portion of the link. The feed bar can also include a distal end having an advancer that is adapted to engage a distal-most clip and to drive the distal-most clip into the jaws. In certain exemplary embodiments, the feed bar can be adapted to engage and initiate advancement of a distal-most clip into the jaws prior to initiating advancement of the feeder shoe.

In another embodiment, a clip advancing assembly for advancing a clip through a surgical clip applier is provided. The clip advancing assembly can be used with a variety of surgical clip appliers, including those known in the art. In one exemplary embodiment, the clip advancing assembly can include a clip track that is adapted to seat at least one clip, and a feeder shoe that is adapted to slidably mate to the clip track and to move in a distal direction to move at least one clip disposed within the clip track in a distal direction. The feeder shoe can include, in one exemplary embodiment, a tang that is adapted to engage the clip track to prevent proximal movement of the feeder shoe within the clip track, and that is adapted to allow distal movement of the feeder shoe within the clip track. The clip track can include a plurality of openings formed therein for receiving the tang to prevent proximal movement of the feeder shoe within the clip track.

The clip advancing assembly can also include a feed bar that is adapted to couple to a movable trigger formed on a housing of a surgical clip applier and that is adapted to slidably move distally when the trigger is closed to advance the feeder shoe and at least one clip disposed within the clip track. The feed bar can have a variety of configurations, and in one exemplary embodiment the distal end of the feed bar can include an advancer that is adapted to engage a distal-most clip to drive the distal-most clip from the clip track into jaws formed on a distal end of a surgical clip applier. In another exemplary embodiment, the feeder shoe can include a tang, and the feed bar can include a plurality of detents formed therein that are adapted to engage the tang to move the feeder shoe distally when the feed bar is moved distally. In use, the proximal end of the feed bar can include a coupler that is adapted to receive a link for coupling the feed bar to a trigger of a surgical clip applier.

An exemplary method for advancing a surgical clip through an elongate shaft of a surgical clip applier is also provided. In one embodiment, a feed bar can be distally advanced within an elongate shaft of a surgical clip applier to distally drive a feeder shoe disposed within the elongate shaft and thereby distally advance at least one clip. The feed bar can be distally advanced by, for example, actuating a trigger coupled to a housing that is mated to a proximal end of the elongate shaft. In one exemplary embodiment, when the feed bar is distally advanced, an advancer on the distal end of the feed bar can engage a distal-most clip and advance the clip between opposed jaws formed on a distal end of the elongate shaft. The method can also include proximally retracting the feed bar within the elongate shaft while the feeder shoe is maintained in a substantially fixed position.

In another exemplary embodiment, a method for applying a surgical clip is provided and includes moving a trigger coupled to a housing a first distance toward a closed position to actuate a clip advancing assembly disposed within the housing, thereby advancing a clip into a jaw assembly formed on a distal end of the elongate shaft, and further moving the trigger a second distance toward the closed position to actuate a clip forming assembly disposed within the housing, thereby forming the clip disposed within the jaw assembly. The trigger is preferably pliant relative to the clip advancing assembly during actuation of the clip forming assembly. The clip forming assembly can also be pliant relative to the jaw assembly during actuation thereof.

In other aspects, an overload mechanism is provided for use with a surgical device. In one exemplary embodiment, the overload mechanism can include a force-receiving member pivotally and slidably disposed in a housing and having a surface with a first end and an opposed second end, and a biasing assembly disposed in the housing and adapted to resist movement of the force-receiving member. In an exemplary embodiment, the resistance increases from the first end to the second end.

The force-receiving member can have a variety of configurations, but in one embodiment the force-receiving surface formed thereon is positioned within an opening in the housing. The force-receiving surface can include a first portion that is adapted to receive a force for pivotally moving the force-receiving member within the housing, and a second portion that is adapted to receive a force for slidably moving the force-receiving member within the housing. The biasing assembly can also have a variety of configurations, but in one exemplary embodiment the biasing assembly can include a spring disposed around a spring post, and a plunger slidably disposed relative to the spring post and having a head formed thereon and adapted to compress the spring upon slidable movement of the plunger toward the spring post.

In another embodiment, the housing can include a pivoting assembly that is coupled between the force-receiving member and the biasing assembly such that pivoting assembly is adapted to transfer a force applied to the force-receiving member to the biasing assembly to overcome the resistance. In one exemplary embodiment, the pivoting assembly can include a toggle link that is pivotally coupled to the force-receiving member, and a pivot link that is pivotally coupled to the toggle link and that is adapted to apply a force to the biasing assembly upon pivotal movement thereof.

In another embodiment, a surgical clip applier is provided having an overload mechanism for preventing overload of a closing force applied to jaws of the clip applier. In one exemplary embodiment, the surgical clip applier can include a housing having a trigger movably coupled thereto, an elongate shaft extending from the housing with opposed jaws formed on a distal end thereof and movable between an open position and a closed position, and a camming assembly disposed within the housing and the elongate shaft and coupled to the trigger. The camming assembly can be adapted to apply a closing force to the jaws upon actuation of the trigger to move the jaws from the open position toward the closed position. The camming assembly can also be adapted to transfer the closing force to an overload mechanism disposed within the housing when the closing force is greater than a resistance of the overload mechanism that is applied to the camming assembly. In an exemplary embodiment, the resistance of the overload mechanism correlates to a force required to move the jaws from the open position toward the closed position.

While various techniques can be used to couple the camming assembly to the overload mechanism, in one exemplary embodiment the camming assembly moves relative to a force-receiving surface of the overload mechanism such that the closing force of the camming assembly is applied across the force-receiving surface of the overload mechanism as the trigger is actuated to cause the camming assembly to move the jaws from the open position toward the closed position. The force-receiving surface of the overload mechanism can be adapted to resist movement in a proximal direction and the resistance can increase as the trigger is actuated to cause the camming assembly to move relative to the force-receiving surface and to move the jaws from the open position toward the closed position.

In another exemplary embodiment, the overload mechanism can include a housing having a profile link slidably and pivotally disposed therein and having the force-receiving surface formed thereon and positioned adjacent to an opening formed in the housing. The force-receiving surface can include a first portion that is adapted to receive a force for pivotally moving the force-receiving member within the housing, and a second portion that is adapted to receive a force for slidably moving the force-receiving member within the housing. The overload mechanism can also include a biasing assembly that is adapted to apply a resistance to the profile link. In one exemplary embodiment, the biasing assembly can be coupled to the profile link by a pivoting assembly that is adapted to pivot upon pivotal movement of the profile link, and that is adapted to slide upon slidable movement of the profile link to apply a force to the biasing assembly to overcome the resistance.

Methods for applying a surgical clip applier having an overload mechanism are also provided. In one exemplary embodiment, a closing force can be applied to a pair of opposed jaws formed on a surgical clip applier. The closing force can be effective to move the opposed jaws from an open position to a closed position. When the closing force is greater than a threshold force of an overload mechanism, the closing force is transferred to the overload mechanism disposed within the surgical clip applier. In an exemplary embodiment, the threshold force of the overload mechanism increases as the jaws are moved from an open position toward the closed position.

While the overload mechanism can have a variety of configurations, in one embodiment the overload mechanism can include a force-receiving element that is adapted to receive the closing force, and a biasing assembly that is adapted to resist movement of the force-receiving element in response to the closing force. The surgical clip applier can include a camming assembly that is adapted to apply the closing force to the jaws, and that includes a roller member that rolls across the force-receiving element as the closing force is applied to the jaws. The threshold force of the overload mechanism can increase as the roller member rolls across the force-receiving element. In particular, when the roller member rolls across a first portion of the force-receiving element, the force-receiving elements can pivot if the closing force is greater than the threshold force, and when the roller member rolls across a second portion of the force-receiving element, the force-receiving element can slide if the closing force is greater than the threshold force. In an exemplary embodiment, the threshold force required to pivot the force-receiving element is less than the threshold force required to slide the force-receiving element.

In other aspects, a surgical clip applier is provided and it can include a clip advancing assembly coupled to a trigger and adapted to advance at least one surgical clip through an elongate shaft extending from a housing, and a clip forming assembly coupled to a trigger and adapted to actuate a jaw assembly formed on a distal end of the elongate shaft to form a surgical clip. The trigger can be coupled to the housing and adapted to actuate the clip advancing assembly and the clip forming assembly. In an exemplary embodiment, the trigger has two sequential stages of actuation. The trigger can be effective to actuate the clip advancing assembly during the first stage of actuation, and it can be effective to actuate the clip forming assembly during the second stage of actuation while being pliant relative to the clip advancing assembly.

In other embodiments, a surgical clip applier is provided having features to prevent unintentional clip migration, for example during shipping of the device. In one exemplary embodiment, a surgical clip applier is provided having a clip advancing assembly with a pusher mechanism that is disposed within a clip track and movable toward the jaws to advance a plurality of clips sequentially into the jaws. The pusher mechanism can be adapted to generate friction with the clip track to prevent unintentional movement of the pusher mechanism within the clip track, but it can be adapted to move when the clip advancing assembly is actuated to advance the pusher mechanism distally.

While various techniques can be used to generate friction between a pusher mechanism and a clip track, in one embodiment the clip track can include one or more protrusions formed thereon and in contact with the pusher mechanism to generate friction with the clip track. In another embodiment, the pusher mechanism can include a deflectable tang formed thereon and biased against the feed bar to generate friction with the feed bar. The deflectable tang can include a lip formed thereon and adapted to engage a corresponding ridge formed in the feed bar. In yet another embodiment, the pusher mechanism can have a cantilevered configuration to generate friction with the clip track. In one embodiment, opposed sidewalls extending along a length of the clip track can bias the pusher mechanism from a substantially V-shaped cross-section into a substantially straight cross-section, thereby generating friction.

In yet another embodiment, a surgical clip applier is provided having a housing with a trigger movably coupled thereto and a shaft extending therefrom with opposed jaws formed on a distal end thereof. A clip track extends through the shaft and is adapted to retain a plurality of clips. The surgical clip applier can also include a feeder shoe slidably disposed within the clip track and adapted to advance the plurality of clips through the clip track. The feeder shoe can be configured to generate friction with the clip track to resist unintentional movement of the feeder shoe. For example, the feeder shoe and/or the clip track can include at least one of a protrusion, a deflectable tang, or other surface feature adapted to generate friction with the clip track. In other embodiments, the pusher can include a deflectable tang with a lip formed thereon and adapted to engage a corresponding ridge formed in the clip track. Alternatively, or in addition, the feeder shoe can have a cantilevered configuration to generate friction with the clip track. The clip track can include a support surface with opposed side walls extending therealong, and the feeder shoe can be slidably disposed between the opposed sidewalls. The opposed sidewalls can bias the feeder shoe from a substantially V-shaped cross-section into a substantially straight cross-section, thereby generating friction.

In yet another embodiment, a surgical clip applier is provided having a housing, a shaft extending from the housing, first and second jaws formed on a distal end of the shaft and adapted to receive tissue therebetween, a clip track extending through the shaft and adapted to retain a plurality of clips, and a clip pusher disposed within the clip track and adapted to advance the plurality of clips through the clip track and into the first and second jaws. The clip pusher can be biased within the clip track such that movement of the clip pusher is prevented unless a force is applied to the clip pusher that is greater than a biasing force created between the clip pusher and the clip track.

In one exemplary embodiment, the clip pusher can include a biasing mechanism formed thereon and adapted to bias the clip pusher within the clip track. The biasing mechanism can be, for example, a protrusion formed on the clip pusher, or a deflectable tang formed on the clip pusher. In other embodiments, the clip pusher can have a width that is greater than a width of the clip track such that the clip pusher is biased within the clip track. The clip track can optionally be sized to deform the clip pusher to create a biasing force between the clip track and the clip pusher. In an exemplary embodiment, the clip pusher is deflected by the clip track such that the clip pusher is compressed from a substantially V-shaped profile to a planar or flattened profile, thereby generating friction.

In yet another embodiment, a surgical clip applier is provided having features to prevent a clip from falling out during formation. In one exemplary embodiment, an improved endoscopic surgical clip applier is provided having jaws which close together to approximate tissues to be clipped, a push rod adapted to close the jaws, a trigger adapted to actuate the push rod, and a ratchet mechanism adapted to prevent the trigger from opening during at least a portion of a closing stroke. A preloaded joint is formed between the push rod and a linkage coupling the push rod to the trigger. The preloaded joint is effective to maintain the jaws in a substantially fixed partially closed position when the trigger is partially opened during a closing stroke to retain a partially formed clip between the jaws. The preloaded joint can also be adapted to maintain the push rod in a substantially fixed position while allowing the linkage to move proximally.

The preloaded joint can have a variety of configurations, but in one embodiment the preloaded joint is a biasing element that is adapted to be compressed by the push rod during a closing stroke, and that is adapted to apply a biasing force to the push rod when the trigger is partially opened. The biasing element can be, for example, a cantilevered beam or a spring. In an exemplary embodiment, a proximal end of the push rod and the biasing element are disposed within a recess formed in a coupling mechanism, and the cantilevered beam or spring biases the proximal end of the push rod distally. The recess can also optionally include ridges formed therein and adapted to maintain the spring at a substantially constant load as the spring is compressed during a closing stroke. The ridges can also be adapted to prevent the spring from fully compressing.

In yet another embodiment, a surgical clip applier is provided having a handle with a shaft extending therefrom, jaws formed on a distal end of the shaft, a jaw closing mechanism extending through the shaft and coupled to the jaws, and a trigger adapted to actuate the jaw closing mechanism to close the jaws. A preloaded joint is formed between the jaw closing mechanism and the trigger, and it is configured to prevent a clip from falling out of the jaws when the trigger is partially opened during a closing stroke. In one embodiment, the preloaded joint can be a spring adapted to be compressed by a portion of the jaw closing mechanism during a closing stroke. The spring can be formed from, for example, Nitinol. In another embodiment, the preloaded joint can be disposed within a recess formed in a coupling mechanism extending between a push rod and the trigger. The preloaded joint can be adapted to be compressed by the push rod during a closing stroke.

In other aspects, a surgical clip applier is provided having a housing, a shaft extending distally from the housing, first and second jaws formed on a distal end of the shaft, a trigger movably coupled to the housing, and an anti-backup mechanism adapted to engage the trigger when the trigger is released during at least a partial closing stroke. An assembly is coupled between the trigger and the jaws and it can be adapted to maintain the jaws in a substantially fixed position to prevent clip fallout when the trigger is released during at least a partial closing stroke.

In an exemplary embodiment, the assembly can include a preloaded joint formed therein for maintaining a portion of the assembly in a fixed position and allowing a portion of the assembly to move proximally when the trigger is released during at least a partial closing stroke. In certain aspects, the preloaded joint can be formed between a push rod adapted to advance a cam over the jaws to close the jaws, and a coupling mechanism for coupling the push rod to the trigger. The preloaded joint can maintain the push rod in a fixed position while allowing the coupling mechanism to move proximally when the trigger is released during at least a partial closing stroke. In certain exemplary embodiments, the preloaded joint is a spring disposed between the push rod and the coupling mechanism.

The present invention also provides exemplary techniques for aligning a clip with opposed jaws formed on a distal end of a surgical clip applier, and preferably for maintaining the clip in alignment with the jaws during clip formation. In one exemplary embodiment, a surgical clip applier is provided having a shaft with proximal and distal ends, opposed jaws formed on the distal end of the shaft, and a guide member coupled to the jaws and having an alignment mechanism formed thereon and adapted to guide a clip into the opposed jaws and to maintain the clip in alignment with the opposed jaws as opposed legs of the clip are closed. The alignment mechanism can also be adapted to abut against an inferior surface of at least a portion of a clip being formed between the opposed jaws to limit or prevent vertical movement of the clip, i.e., pivoting of the apex and legs in a superior-inferior direction.

The alignment mechanism can be formed on various portions of the clip applier, but in one exemplary embodiment, the guide member is a tissue stop having a distal end with a recess formed therein for seating a vessel. The alignment mechanism can be a ramped member protruding from a superior surface of the tissue stop. In an exemplary embodiment, the ramped member increases in height from a proximal end to a distal end of the tissue stop.

In another embodiment, a surgical clip applier is provided having a shaft, opposed jaws formed on a distal end of the shaft and adapted to close together to approximate tissues to be clipped, and a clip advancing assembly movably coupled to the shaft and adapted to advance a clip into the opposed jaws. An advancer guide is disposed just proximal to the opposed jaws and is adapted to guide a clip being advanced by the clip advancing assembly into the opposed jaws. The advancer guide can be adapted to align the clip with the opposed jaws. The advancer guide can also be adapted to limit or prevent vertical movement of a clip being formed between the opposed jaws.

In certain exemplary embodiments, the advancer guide can be formed on a tissue stop coupled to the opposed jaws, and having a recess formed in a distal tip thereof and adapted to receive tissue therein. The advancer guide can be in the form of a ramped member protruding above a superior surface of the tissue stop.

In other aspects, an improved endoscopic surgical clip applier is provided having jaws which close together to approximate tissues to be clipped and a clip advancing assembly adapted to sequentially advance a plurality of clips into the jaws. A ramped guide member is positioned just proximal to the opposed jaws and is adapted to align and guide a clip being advanced by the clip advancing assembly into the opposed jaws, and to limit or prevent vertical movement of the clip as the clip is being formed between the opposed jaws. In one embodiment, the ramped guide member can be formed on a tissue stop coupled to the opposed jaws, and the tissue stop can include a distal tip adapted to receive tissue therein to align the jaws with tissue to be clipped. In certain exemplary embodiments, the ramped guide member increases in height from a proximal end to a distal end thereof. The ramped guide member can be adapted to abut against an inferior surface of at least a portion of a clip being formed between the opposed jaws to limit or prevent vertical movement of the clip, i.e., pivoting of the apex and legs in a superior-inferior direction. In an exemplary embodiment, the ramped guide member has a maximum height of about 0.025", and/or it is inclined at an angle in the range of about 5° to 45°.

BRIEF DESCRIPTION OF THE DRAWINGS

The invention will be more fully understood from the following detailed description taken in conjunction with the accompanying drawings, in which:

FIG. 2A is a top view of a jaw retainer assembly of the surgical clip applier shown in FIG. 1A;

FIG. 2B is a bottom view of the jaw retainer assembly shown in FIG. 2A;

FIG. 2C is a side view of the jaw retainer assembly shown in FIG. 2B;

FIG. 2D is a cross-sectional view of the jaw retainer assembly shown in FIG. 2C taken across line D-D;

FIG. 3A is a top view of a feeder shoe for use with the jaw retainer assembly shown in FIGS. 2A-2D;

FIG. 3B is a bottom view of the feeder shoe shown in FIG. 3A;

FIG. 4B is a side view of the proximal end of the feed bar shown in FIG. 4A and the proximal end of the jaw retainer shaft shown in FIGS. 2A and 2B, showing the feed bar in a proximal-most position;

FIG. 4C is a side view of the feed bar and jaw retainer shaft shown in FIG. 4B, showing the feed bar in a distal-most position;

FIG. 4D is a side view of another embodiment of a proximal end of a feed bar shown in connection with the proximal end of the jaw retainer shaft shown in FIGS. 2A and 2B, showing the feed bar in the proximal-most position;

FIG. 4E is a side view of the feed bar and jaw retainer shaft shown in FIG. 4D, showing the feed bar in a distal-most position;

FIG. 4F is a side view of yet another embodiment of a proximal end of a feed bar shown in connection with the proximal end of the jaw retainer shaft shown in FIGS. 2A and 2B, showing the feed bar in the proximal-most position;

FIG. 4G is a side view of the feed bar and jaw retainer shaft shown in FIG. 4F, showing the feed bar in an intermediate position;

FIG. 4H is a side view of the feed bar and jaw retainer shaft shown in FIG. 4F, showing the feed bar in a distal-most position;

FIG. 6A is a cross-sectional view of a clip advancing assembly, which includes the jaw retainer assembly shown in FIGS. 2A-2D, the feeder shoe shown in FIGS. 3A-3B, and the feed bar shown in FIG. 4A, showing the feed bar in an initial, proximal position relative to the clip track of the jaw retainer assembly;

FIG. 6B is a cross-sectional view of the clip advancing assembly shown in FIG. 6A, showing the feed bar moved in a distal direction;

FIG. 6C is a cross-sectional view of the clip advancing assembly shown in FIG. 6B, showing the feed bar moved further distally, thereby moving the feeder shoe and a clip supply disposed distally of the feeder shoe in a distal direction;

FIG. 6D is a cross-sectional view of the clip advancing assembly shown in FIG. 6C, showing the feed bar returned to the initial, proximal position, shown in FIG. 6A, while the feeder shoe and clip supply remain in the advanced position shown in FIG. 6C;

FIG. 9 is a top perspective view of a push rod that is adapted to couple to the cam shown in FIG. 8 for moving the cam relative to the jaws shown in FIG. 7;

FIG. 22A is a side, partially cross-sectional view of a portion of the handle of the surgical clip applier shown in FIG. 1A, showing the anti-backup mechanism in an initial position;

FIG. 22C is a side, partially cross-sectional view of a portion of the handle of the surgical clip applier shown in FIG. 22B, showing the anti-backup mechanism in a fully actuated position;

DETAILED DESCRIPTION OF THE INVENTION

Figure 1A:
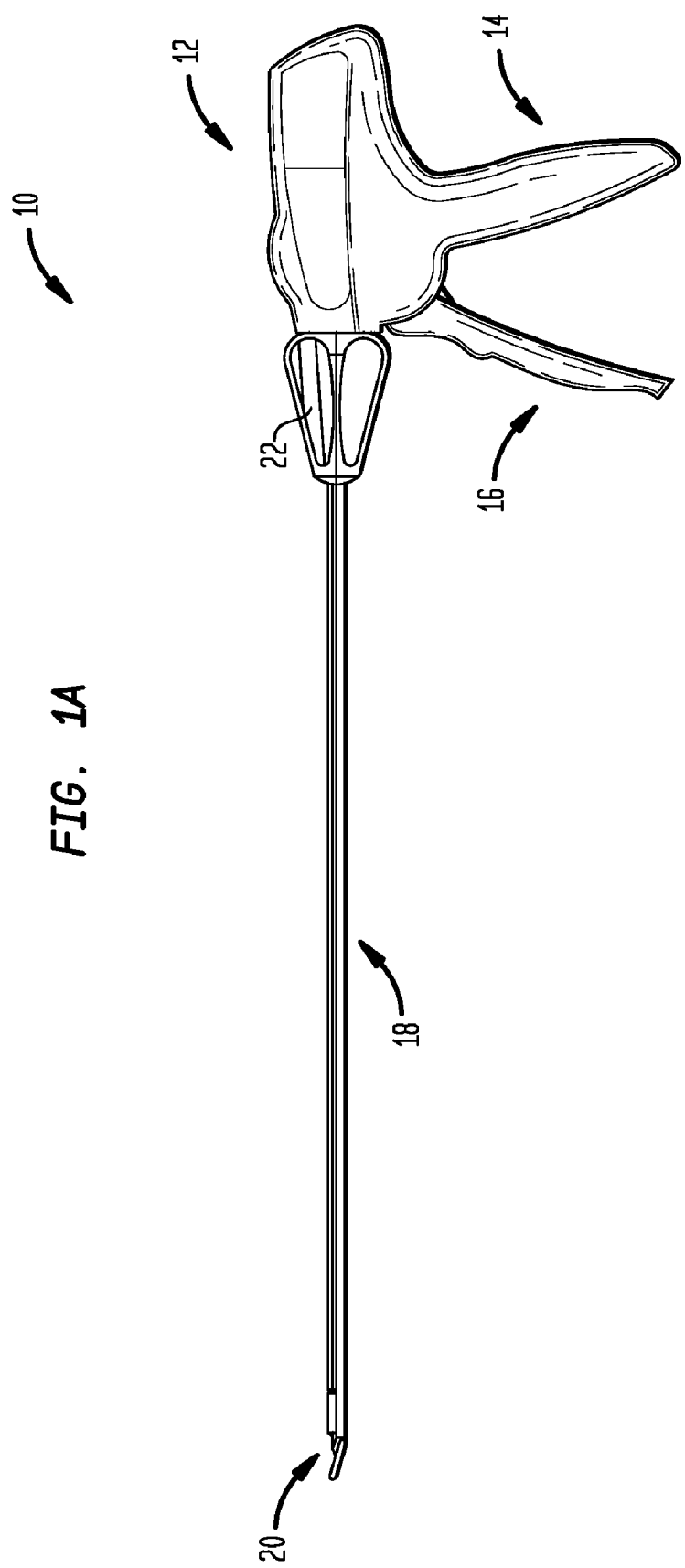
FIG. 1A is a side view of one exemplary embodiment of a surgical clip applier.

The present invention generally provides a surgical clip applier and methods for using a surgical clip applier to apply surgical clips to a vessel, duct, shunt, etc., during a surgical procedure. An exemplary surgical clip applier can include a variety of features to facilitate application of a surgical clip, as described herein and illustrated in the drawings. However, a person skilled in the art will appreciate that the surgical clip applier can include only some of these features and/or it can include a variety of other features known in the art. The surgical clip applier described herein is merely intended to represent certain exemplary embodiments.

Figure 1B:
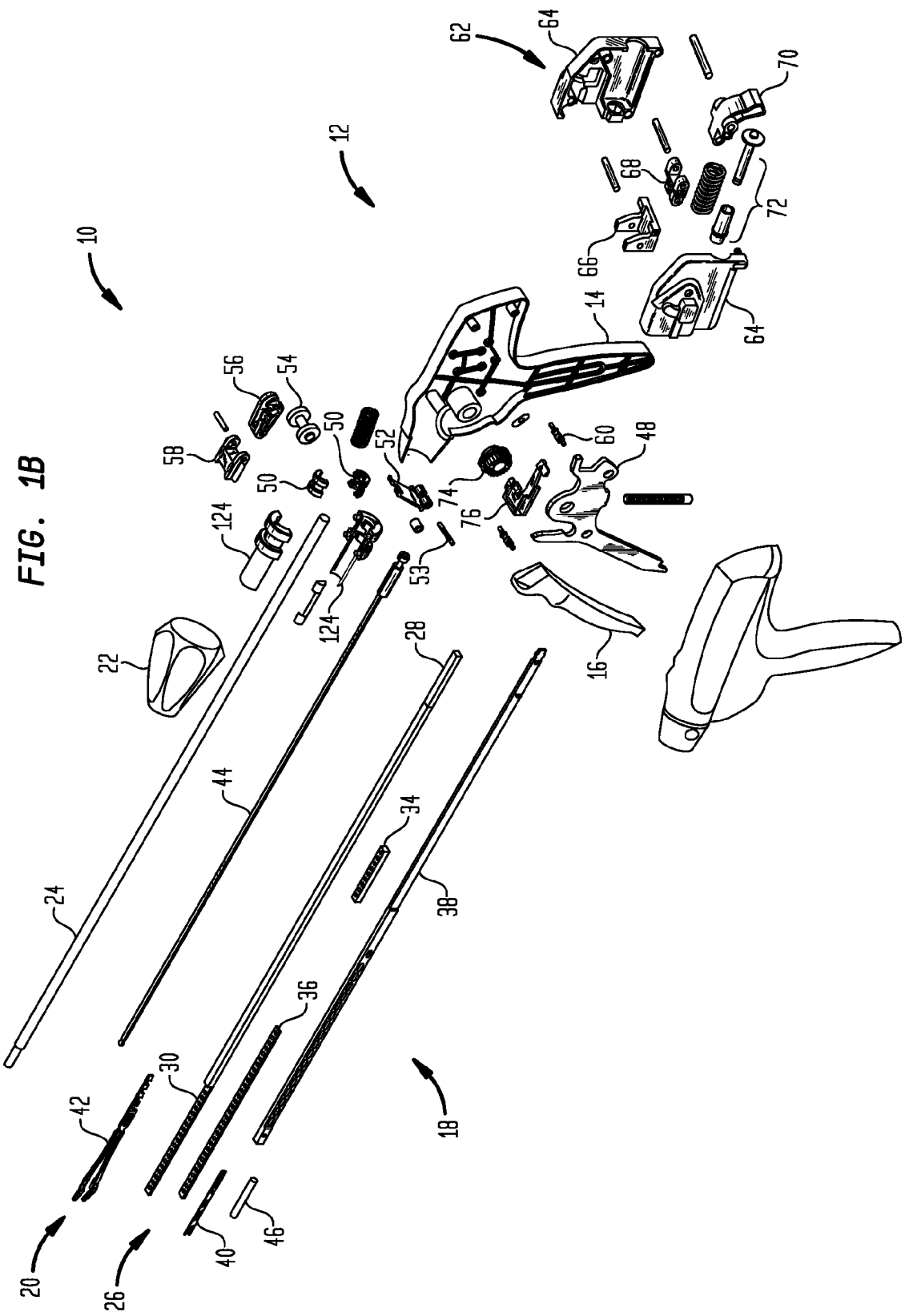
FIG. 1B is an exploded view of the surgical clip applier shown in FIG. 1A.

FIG. 1A illustrates one exemplary surgical clip applier 10. As shown, the clip applier 10 generally includes a housing 12 having a stationary handle 14 and a movable handle or trigger 16 that is pivotally coupled to the housing 12. An elongate shaft 18 extends from the housing 12 and it includes a pair of opposed jaws 20 formed on a distal end thereof for crimping a surgical clip. The elongate shaft 18 can be rotatably coupled to the housing 12, and it can include a rotation knob 22 for rotating the shaft 18 relative to the housing 12. FIG. 1B illustrates an exploded view of the surgical clip applier 10 shown in FIG. 1A, and the various components will be described in more detail below.

FIGS. 2A-12 illustrate exemplary embodiments of the various components of the shaft 18 of the surgical clip applier 10. In general, referring to FIG. 1B, the shaft 18 includes an outer tube 24 that houses the shaft components, which can include a jaw retaining assembly 26 having a jaw retainer shaft 28 with a clip track 30 and a push rod channel 32 formed thereon. The jaws 20 can be configured to mate to a distal end of the clip track 30. The shaft assembly 18 can also include a clip advancing assembly, which in one exemplary embodiment can include a feeder shoe 34 that is adapted to be slidably disposed within the clip track 30 to advance a series of clips 36 positioned therein, and a feed bar 38 that is adapted to drive the feeder shoe 34 through the clip track 30. The feed bar 38 can include an advancer assembly 40 that is adapted to mate to a distal end thereof for advancing a distal-most clip into the jaws 20. The shaft assembly 18 can also include a clip forming or camming assembly, which in one exemplary embodiment can include a cam 42 that is adapted to slidably mate to the jaws 20, and a push rod 44 that can couple to the cam 42 to move the cam 42 relative to the jaws 20. The shaft assembly can also include a tissue stop 46 that can mate to a distal end of the clip track 30 for facilitating positioning of the jaws 20 relative to a surgical site.

The various components of one exemplary clip advancing assembly are shown in more detail in FIGS. 2A-5. Referring first to FIGS. 2A-2D, the jaw retaining assembly 26 is shown and it includes an elongate, substantially planar jaw retainer shaft 28 having a proximal end 28a that mates to the outer tube 24, and a distal end 28b that is adapted to mate to the jaws 20. While a variety of techniques can be used to mate the proximal end 28a of the jaw retainer shaft 28 to the outer tube 24, in the illustrated embodiment the proximal end 28a includes teeth 31 formed on opposed sides thereof that are adapted to be received within corresponding holes or openings (not shown) formed in the outer tube 24, and a cut-out 29 formed therein that allows the opposed sides of the proximal end 28a to deflect or to form a spring. In particular, the cut-out 29 allows the opposed sides of the proximal end 28a of the jaw retainer shaft 28 to be compressed toward one another when the jaw retainer shaft 28 is inserted in the outer tube 24. Once the teeth 31 are aligned with the corresponding openings in the outer tube 24, the proximal end 28a of the jaw retainer shaft 28 will return to its original, uncompressed configuration thereby causing the teeth 31 to extend into the corresponding openings to engage the outer 24. As will be discussed in more detail below with respect to FIG. 4A, the device can also include a feature to prevent compression of the opposed sides of the proximal end 28a of the jaw retainer shaft 28 during use of the device to prevent accidental disengagement of the teeth 31 from the outer tube 24.

A variety of techniques can also be used to mate the distal end 28b of the jaw retainer shaft 28 to the jaws 20, however in the illustrated embodiment the distal end 28b of the jaw retainer shaft 28 includes several cut-outs or teeth 78 formed therein for mating with corresponding protrusions or teeth 94 formed on the jaws 20, which will be discussed in more detail below with respect to FIG. 7. The teeth 78 allow a proximal portion of the jaws 20 to be substantially co-planar with the jaw retainer shaft 28.

The jaw retaining assembly 26 can also include a push rod channel 32 formed thereon for slidably receiving the push rod 44, which is used to advanced the cam 42 over the jaws 20, as will be discussed in more detail below. The push rod channel 32 can be formed using a variety of techniques, and it can have any shape and size depending on the shape and size of the push rod 44. As shown in FIG. 2D, the push rod channel 32 is fixedly attached, e.g., by welding, to a superior surface of the retainer shaft 28, and it has a substantially rectangular shape and defines a pathway 32a extending therethrough. The push rod channel 32 can also extend along all or only a portion of the retainer shaft 28. A person skilled in the art will appreciate that the jaw retaining assembly 26 does not need to include a push rod channel 32 for facilitating movement of the push rod 44 within the elongate shaft 18 of the surgical clip applier 10.

As is further shown in FIGS. 2A-2D, the jaw retaining assembly 26 can also include a clip track 30 mated thereto or formed thereon. The clip track 30 is shown mated to an inferior surface of the jaw retainer shaft 28, and it extends distally beyond the distal end 28b of the jaw retainer shaft 28 to allow a distal end 30b of the clip track 30 to be substantially aligned with the jaws 20. In use, the clip track 30 is configured to seat at least one, and preferably a series, of clips therein. Accordingly, the clip track 30 can include opposed side rails 80a, 80b that are adapted to seat opposed legs of one or more clips therein, such that the legs of the clips are axially aligned with one another. In an exemplary embodiment, the clip track 30 can be configured to seat about twenty clips that are pre-disposed within the clip track 30 during manufacturing. A person skilled in the art will appreciate that the shape, size, and configuration of the clip track 30 can vary depending on the shape, size, and configuration of clips, or other closure devices such as staples, adapted to be received therein. Moreover, a variety of other techniques can be used, instead of a clip track 30, to retain a clip supply with the elongate shaft 18.

The clip track 30 can also include several openings 30c formed therein for receiving a tang 82a formed on a feeder shoe 34 adapted to be disposed within the clip track 30, as will be discussed in more detail below. In an exemplary embodiment, the clip track 30 includes a quantity of openings 30c that corresponds to at least the number of clips adapted to be pre-disposed within the device 10 and applied during use. The openings 30c are preferably equidistant from one another to ensure that the tang 82a on the feeder shoe 34 engages an opening 30c each time the feeder shoe 34 is advanced. While not shown, the clip track 30 can include detents, rather than openings 30c, or it can include other features that allow the clip track 30 to engage the feeder shoe 34 and prevent distal movement, yet allow proximal movement, of the feeder shoe 34. The clip track 30 can also include a stop tang 118 formed thereon, as shown in FIG. 2B, that is effective to be engaged by a corresponding stop tang formed on the feeder shoe 34 to prevent movement of the feeder shoe 34 beyond a distal-most position, as will be discussed below. The stop tang 118 can have a variety of configurations, but in one exemplary embodiment it is in the form of two adjacent tabs that extend toward one another to enclose a portion of the clip track, thus allowing clips to pass therethrough.

An exemplary feeder shoe 34 is shown in more detail in FIGS. 3A and 3B, and it can be adapted to directly driving clips through the clip track 30. While the feeder shoe 34 can have a variety of configurations, and a variety of other techniques can be used to drive clips through the clip track 30, in an exemplary embodiment the feeder shoe 34 has a generally elongate shape with proximal and distal ends 34a, 34b. The distal end 34b can be adapted to cradle the proximal-most clip in the clip track 30 to push the clip(s) through the clip track 30. In the illustrated exemplary embodiment, the distal end 34b is substantially v-shaped for seating a v-shaped bight portion of a clip. The distal end 34b also includes a rectangular-shaped notch 34c formed therein for allowing the advancer 40 to engage a distal-most clip and advance it into the jaws 20, as will be discussed in more detail below. The distal end 34b can, of course, vary depending on the configuration of the clip, or other closure mechanism, being used with the device 10.

In another exemplary embodiment, the feeder shoe 34 can also include features to facilitate distal movement of the feeder shoe 34 within the clip track 30, and to substantially prevent proximal movement of the feeder shoe 34 within the clip track 30. Such a configuration will ensure advancement and proper positioning of the clips within the clip track 30, thus allowing a distal-most clip to be advanced between the jaws 20 with each actuation of the trigger 16, as will be discussed in more detail below. In the illustrated exemplary embodiment, the feeder shoe 34 includes a tang 82*a* formed on a superior surface 34*s* thereof and angled proximally for engaging one of the openings 30*c* formed in the clip track 30. In use, the angle of the tang 82*a* allows the feeder shoe 34 to slide distally within the clip track 30. Each time the feeder shoe 34 is advanced, the tang 82*a* will move in a distal direction from one opening 30*c* to the next opening 30*c* in the clip track 30. The engagement of the tang 82*a* with the opening 30*c* in the clip track 30 will prevent the feeder shoe 34 from moving proximally to return to the previous position, as will be described in more detail below.

In order to facilitate proximal movement of the feeder shoe 34 within the clip track 30, the feeder shoe 34 can also include a tang 82*b* formed on the inferior surface 34*i* thereof, as shown in FIG. 3B, for allowing the feeder shoe 34 to be engaged by the feed bar 38 (FIG. 4A) as the feed bar 38 is moved distally. The inferior tang 82*b* is similar to the superior tang 82*a* in that it can be angled proximally. In use, each time the feed bar 38 is moved distally, a detent 84 formed in the feed bar 38 can engage the inferior tang 82*b* and move the feeder shoe 34 distally a predetermined distance within the clip track 30. The feed bar 38 can then be moved proximally to return to its initial position, and the angle of the inferior tang 82*b* will allow the tang 82*b* to slide into the next detent 84 formed in the feed bar 38. As previously noted, a variety of other features rather than tangs 82*a*, 82*b* and openings 30*c* or detents 84 can be used to control movement of the feeder shoe 34 within the clip track 30.

As previously mentioned, the feeder shoe 34 can also include a stop formed thereon that is adapted to stop movement of the feeder shoe 34 when the feeder shoe 34 is in the distal-most position and there are no clips remaining in the device 10. While the stop can have a variety of configurations, FIGS. 3A and 3B illustrate a third tang 82*c* formed on the feeder shoe 34 and extending in an inferior direction for engaging the stop tang 118 (FIG. 2B) formed on the clip track 30. The third tang 82*c* is positioned such that it will engage the stop tang 118 on the clip track 30 when the feeder shoe 34 is in a distal-most position, thereby preventing movement of the feeder shoe 34 and the feed bar 38 when the clip supply is depleted.

Figure 4A:
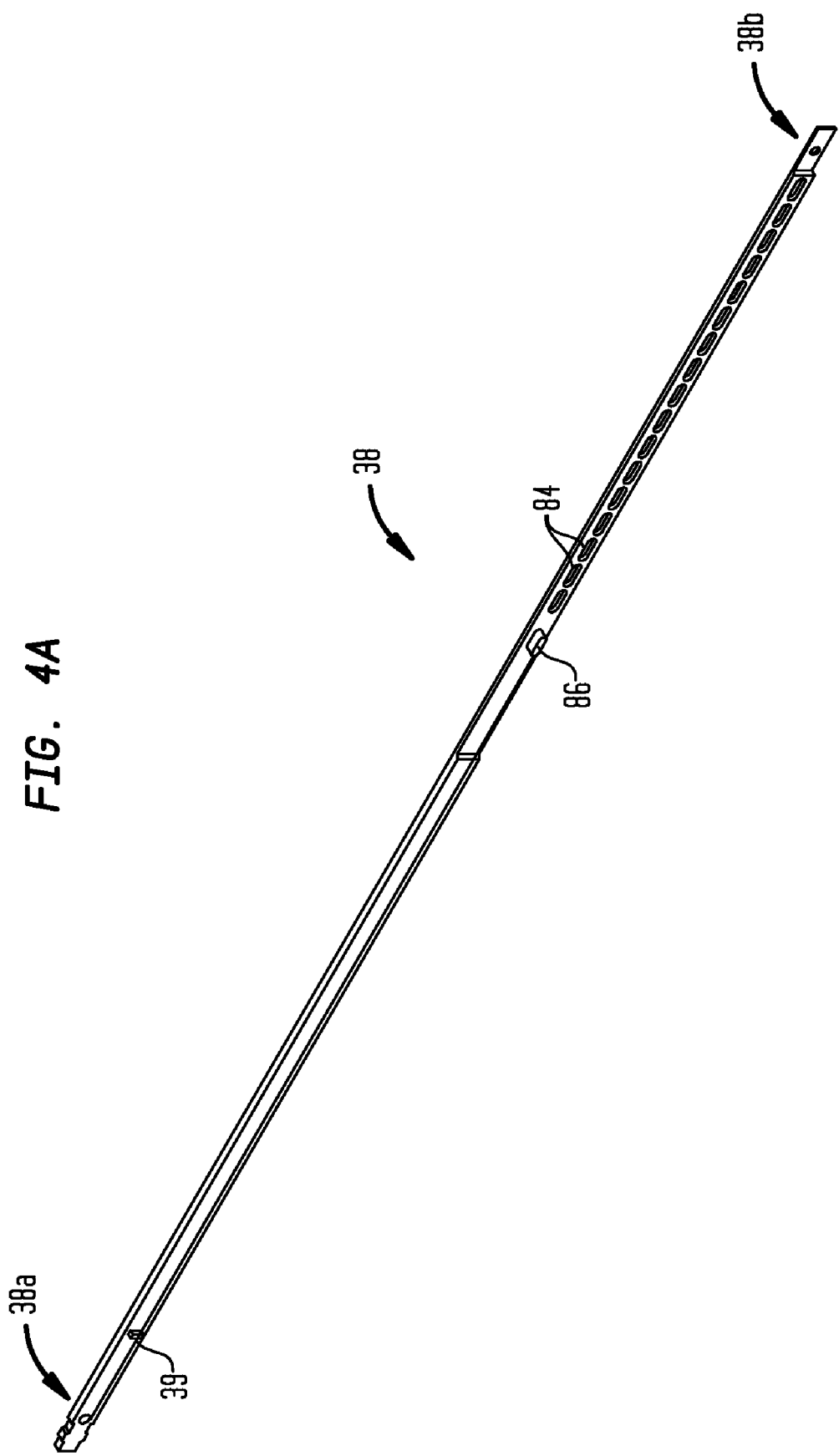
FIG. 4A is a side perspective view of a feed bar that is configured to advance the feeder shoe of FIGS. 3A and 3B through the jaw retainer assembly shown in FIGS. 2A-2D.
Figure 5A:
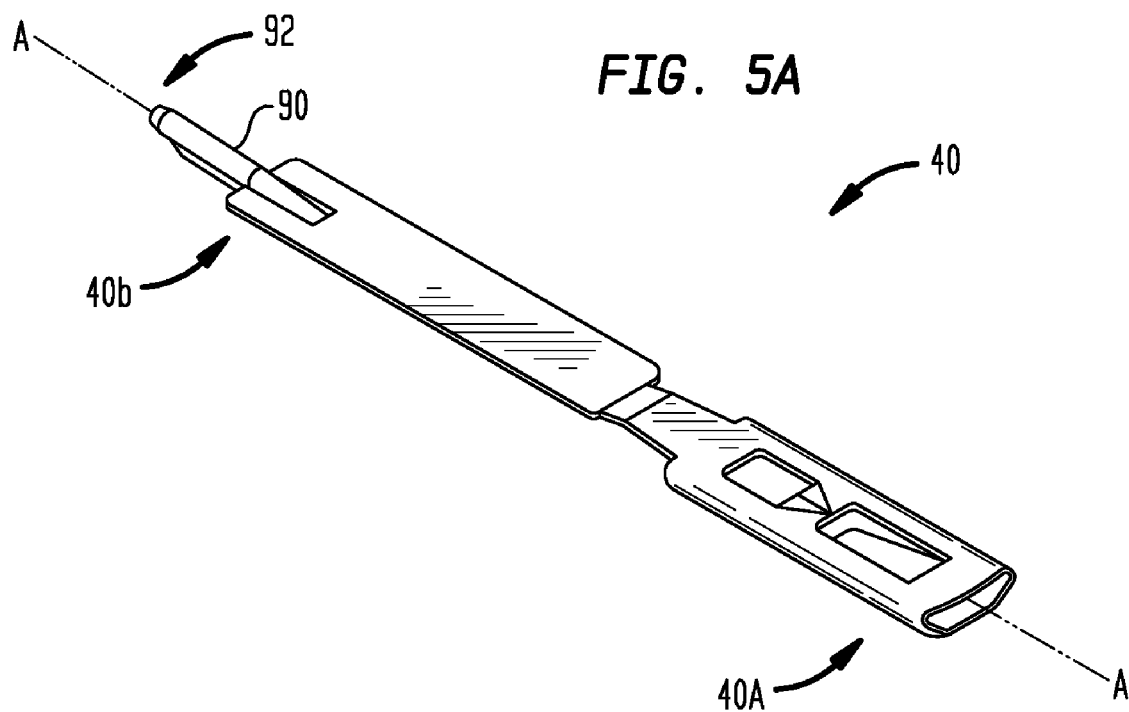
FIG. 5A is a side perspective view of an advancer that is configured to couple to a distal end of the feed bar shown in FIG. 4A.
Figure 5B:
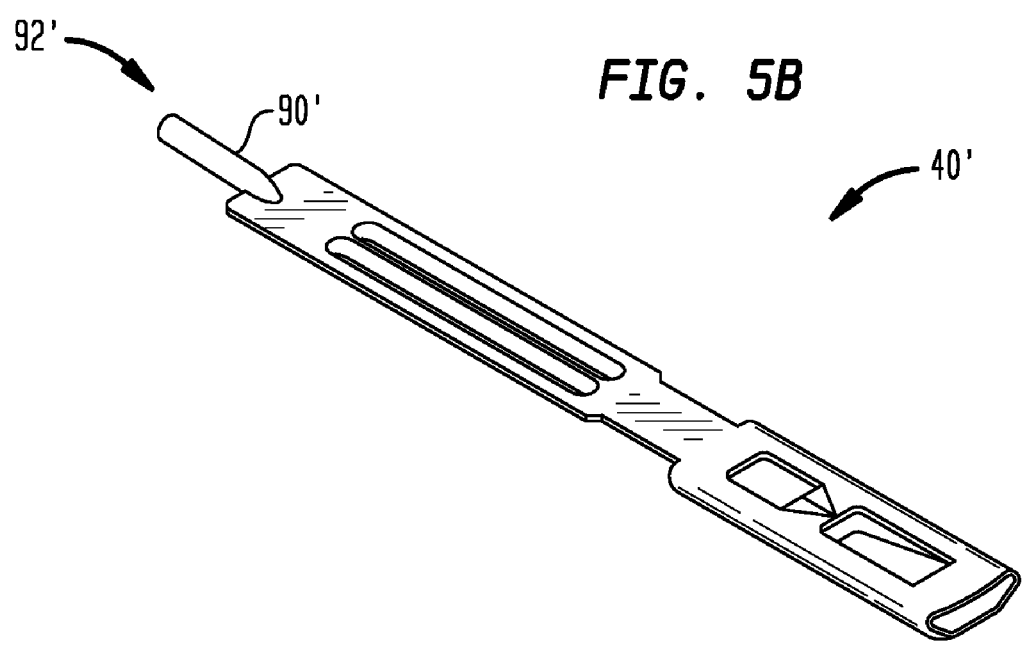
FIG. 5B is a side perspective view of another embodiment of an advancer that is configured to couple to a distal end of the feed bar shown in FIG. 4A.

FIG. 4A illustrates an exemplary feed bar 38 for driving the feeder shoe 34 through the clip track 30 of the jaw retaining assembly 26. As shown, the feed bar 38 has a generally elongate shape with proximal and distal ends 38*a*, 38*b*. The proximal end 38*a* of the feed bar 38*a* can be adapted to mate to a feed bar coupler 50 (FIG. 1B), which will be discussed in more detail below. The feed bar coupler 50 can mate to a feed link 52 that is effective, upon actuation of the trigger 16, to slidably move the feed bar 38 in a distal direction within the elongate shaft 18. The distal end 38*b* of the feed bar 38*b* can be adapted to mate to an advancer 40, 40', exemplary embodiments of which are shown in FIGS. 5A and 5B, that is effective to drive a distal-most clip disposed within the clip track 30 into the jaws 20, which will be discussed in more detail below.

As previously mentioned, the proximal end 38*a* of the feed bar 38 can include a feature to prevent compression of the opposed sides of the proximal end 28*a* of the jaw retainer shaft 28 (FIGS. 2A and 2B) during use of the device to prevent accidental disengagement of the teeth 31 from the outer tube 24. In one exemplary embodiment, shown FIGS. 4A-4C, the proximal end 38*a* of the feed bar 38 can include a protrusion 39 formed thereon that is adapted to extend into the opening 29 formed in the proximal end 28*a* of the jaw retainer shaft 28. When the feed bar 38 is in a proximal-most position (i.e., when the trigger 16 is in an open position), the protrusion 39 will be positioned at the proximal end of the opening 29, as shown in FIG. 4B, allowing the proximal end 28*a* of the jaw retainer shaft 28 to compress to allow the shaft 28 to slide into the outer tube 24. When the feed bar 38 is in a distal-most position (i.e., when the trigger 16 is in at least a partially closed position), the protrusion 39 will be positioned at an intermediate location adjacent to the teeth 31 as shown in FIG. 4C, to prevent compression of the proximal end 28*a* of the jaw retainer shaft 28. This is particularly advantageous during use of the device, as the protrusion 39 will prevent accidental disengagement of the jaw retainer shaft 28 from the outer tube 24 during use of the device. While FIGS. 4A-4C illustrate a protrusion 39 having a rectangular cross-sectional shape with rounded edges, the protrusion 39 can have a variety of other shapes and sizes. For example, as shown in FIGS. 4D and 4E, the protrusion 39' has a cross-sectional shape that is somewhat triangular with a tapering end that is adapted to extend between the teeth 31 to further ensure that the proximal end 28*a* of the jaw retainer shaft 28 can not be compressed during use of the device. More than one protrusion can also be used. For example, FIGS. 4F-4H illustrate another embodiment in which the proximal end 38*a'* of the feed bar 38 includes two protrusions 39*a*, 39*b* formed thereon and spaced a distance apart from one another. The two protrusions 39*a*, 39*b* will prevent compression of the proximal end 28*a* of the jaw retainer shaft 28 when the feed bar 38 is in a proximal-most position, as shown in FIG. 4F, and when the feed bar 38 is in a distal-most position, as shown in FIG. 4H. Compression of the proximal end 28*a* of the jaw retainer shaft 28 can only occur when the feed bar 38 is at an intermediate position such that the teeth 31 are positioned between the protrusions 39*a*, 39*b*, as shown in FIG. 4G.

As was also previously mentioned, the feed bar 38 can include one or more detents 84 formed therein for engaging the inferior tang 82*b* formed on the feeder shoe 34. The quantity of detents 84 can vary, but in an exemplary embodiment the feed bar 38 has a quantity of detents 84 that corresponds to or is greater than a quantity of clips adapted to be delivered by the device 10, and more preferably it has one more detent 84 than the quantity of clips adapted to be delivered by the device 10. By way of non-limiting example, the feed bar 38 can include eighteen detents 84 formed therein for delivering seventeen clips that are pre-disposed within the clip track 30. Such a configuration allows the feed bar 38 to advance the feeder shoe 34 seventeen times, thereby advancing seventeen clips into the jaws 20 for application. The detents 84 are also preferably equidistant from one another to ensure that the feeder shoe 34 is engaged and advanced by the feed bar 38 each time the feed bar 38 is advanced.

The feed bar 38 can also include a feature to control the amount of movement of the feed bar 38 relative to the clip track 30. Such a configuration will ensure that the feeder shoe 34 is advanced a predetermined distance each time the trigger 16 is actuated, thereby advancing only a single clip into the jaws 20. While a variety of techniques can be used to control the distal of movement of the feed bar 38, in an exemplary embodiment the feed bar 38 can include a protrusion 86 formed thereon that is adapted to be slidably received within a corresponding slot 88 (FIG. 2B) formed in the jaw retainer shaft 28. The length of the slot 88 is effective to limit movement of the protrusion 86 therein, thus limiting movement of the feed bar 38. Accordingly, in use the feed bar 38 can slide between a fixed proximal position and a fixed distal position with respect to the clip track 30, thereby allowing the feed bar 38 to advance the feeder shoe 34 by a predetermined distance with each advancement of the feed bar 38.

FIG. 5A illustrates one exemplary embodiment of an advancer 40 that is adapted to mate to the distal end 38b of the feed bar 38 and which is effective to drive a distal-most clip from the clip track 30 into the jaws 20. A variety of techniques can be used to mate the advancer 40 to the feed bar 38, but in the illustrated embodiment the proximal end 40a of the advancer 40 is in the form of a female connector that is adapted to receive the male connector formed on the distal end 38b of the feed bar 38. The advancer 40 preferably fixedly mates to the feed bar 38, however it can optionally be integrally formed with the feed bar 38. The distal end 40b of the feed bar 38 is preferably adapted to advance a clip into the jaws 20 and thus the distal end 40b of the advancer 40 can include, for example, a clip-pusher member 90 formed thereon. The clip-pusher member 90 can have a variety of shapes and sizes, but in one exemplary embodiment it has an elongate shape with a recess 92 formed in the distal end thereof for seating the bight portion of a clip. The shape of the recess 92 can vary depending on the particular configuration of the clip. The clip-pusher member 90 can also extend at an angle in a superior direction with respect to a longitudinal axis A of the advancer 40. Such a configuration allows the clip-pusher member 90 to extend into the clip track 30 to engage a clip, while the remainder of the advancer 40 extends substantially parallel to the clip track 30. FIG. 5B illustrates another exemplary embodiment of a clip-pusher member 90' of an advancer 40'. In this embodiment, the clip-pusher member 90' is slightly more narrow and it has a small recess 92' formed in the distal-most end thereof. In use, the advancer 40 can engage and advance only the distal-most clip disposed within the clip track 30 into the jaws 20. This is due to the positioning of the feed bar 38, which is slidably movable between a fixed proximal and distal positions, as previously discussed.

Figure 6E:
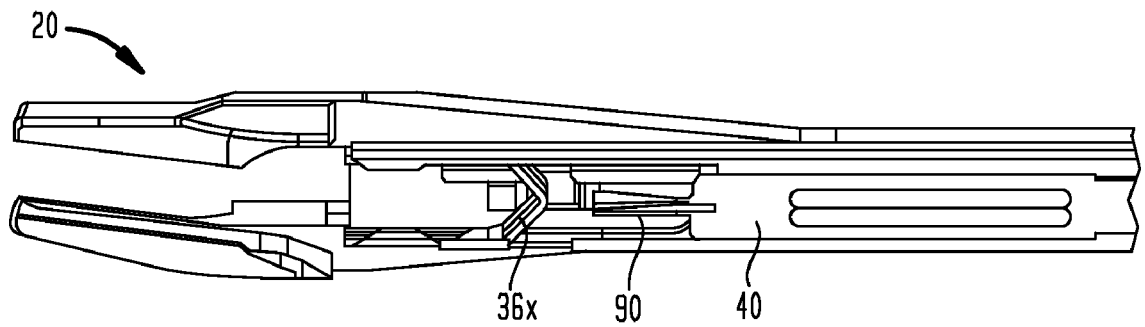
FIG. 6E is a bottom perspective view of the advancer shown in FIG. 5A disposed within the clip track of the jaw retainer assembly shown in FIGS. 2A-2D, showing the advancer in a proximal-most position.
Figure 6F:
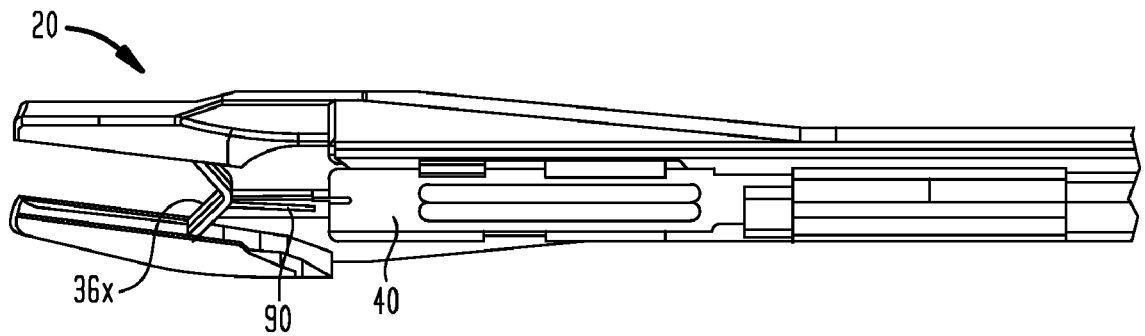
FIG. 6F is a bottom perspective view of the advancer shown in FIG. 6E, showing the advancer in a distal-most position after advancing a clip into the jaws of the surgical clip applier.

FIGS. 6A-6G illustrate the clip advancing assembly in use, and in particular FIGS. 6A-6D illustrate movement of the feed bar 38 within the clip track 30 to advance the feeder shoe 34 and clip supply 36, and FIGS. 6E-6F illustrate movement of the advancer 40 to advance a distal-most clip into the jaws 20. The components in the housing 12 that are used to actuate the clip advancing assembly will be discussed in more detail below.

As shown in FIG. 6A, in the resting position the feed bar 38 is in a proximal-most position such that the protrusion 86 is positioned proximally within the elongate slot 88 in the jaw retainer shaft 28. The feeder shoe 34 is disposed within the clip track 30 and, assuming the device 10 has not yet been used, the feeder shoe 34 is in a proximal-most position such that the superior tang 82a on the feeder shoe 34 is engaged with the proximal-most or first opening $30c_1$ formed in the clip track 30 to prevent proximal movement of the feeder shoe 34, and the inferior tang 82b on the feeder shoe 34 is positioned between the first detent $84_1$ and the second detent $84_2$ in the feed bar 38, such that the inferior tang 82b is biased in a superior direction by the feed bar 38. The detents 84 in the feed bar are labeled sequentially as $84_1$, $84_2$, etc., and the openings 30c in the clip track 30 are labeled sequentially as $30c_1$, $30c_2$, etc. As is further shown in FIG. 6A, a series of clips 36, labeled sequentially as $36_1$, $36_2$, . . . $36_x$ with $36_x$ being the distal-most clip, are positioned within the clip track 30 distal of the feeder shoe 34.

Upon actuation of the trigger 16, the feed bar 38 is advanced distally, causing the protrusion 86 to slide distally within the slot 88. As the feed bar 38 moves distally, the inferior tang 82b on the feeder shoe 34 will slide into the first detent $84_1$ in the feed bar 38. Further distal movement of the feed bar 38 will cause the first detent $84_1$ to engage the inferior tang 82b, as shown in FIG. 6B, and to move the feeder shoe 34 and clip supply $36_1$, $36_2$, etc. in a distal direction. As shown in FIG. 6C, when the protrusion 86 abuts the distal end of the elongate slot 88 in the jaw retainer shaft 28, the feed bar 38 is prevented from further distal movement. In this position, the feeder shoe 34 has advanced a predetermined distance to advance the clip supply $36_1$, $36_2$, . . . $36_x$ within the clip track 30 by a predetermined distance. The superior tang 82a of the feeder shoe 34 has been advanced into the second opening $30c_2$ in the clip track 30 to prevent proximal movement of the feeder shoe 34, and the inferior tang 82b on the feeder shoe 34 is still engaged by the first detent $84_1$ in the feed bar 38.

Movement of the feed bar 38 from the initial, proximal-most position, shown in FIG. 6A, to the final, distal-most position, shown in FIG. 6C, will also advance the distal-most clip $36_x$ into the jaws 20. In particular, as shown in FIG. 6E, distal movement of the feed bar 38 will cause the clip-pusher member 90 of the advancer 40, which is attached to the distal end of the feed bar 38, to engage the distal-most clip $36_x$ disposed within the clip track 30 and to advance the clip $36_x$ into the jaws 20, as shown in FIG. 6F. In an exemplary embodiment, the advancer 40 will engage and initiate advancement of the distal-most clip $36_x$ prior to engaging and initiating advancement of the feeder shoe 34. As a result the distal-most clip $36_x$ will advance a distance that is greater than a distance traveled by the feeder shoe 34. Such a configuration allows only the distal-most clip $36_x$ to be advanced into the jaws 20 without accidentally advancing an additional clip into the jaws 20.

Once the clip $36_x$ has been partially or fully formed, the trigger 16 can be released to release the formed clip $36_x$. Release of the trigger 16 will also retract the feed bar 38 in a proximal direction until the protrusion 86 returns to the initial proximal-most position within the elongate slot 88, as shown in FIG. 6D. As the feed bar 38 is retracted proximally, the feeder shoe 34 will not move proximally since the superior tang 82a will engage the second opening $30c_2$ in the clip track 30. The inferior tang 82b will not interfere with proximal movement of the feed bar 38, and once the feed bar 38 is in the initial, proximal-most position, as shown, the inferior tang 82b will be positioned between the second detent $84_2$ and the third detent $84_3$ in the feed bar 38.

The process can be repeated to advance another clip into the jaws 20. With each actuation of the trigger 16, the inferior tang 82b will be engaged by the next detent, i.e., detent $84_2$ formed in the feed bar 38, the superior tang 82a on the feeder shoe 34 will be moved distally into the next opening, i.e., opening $30c_3$ on the clip track 30, and the distal-most clip will be advanced into the jaws 20 and released. Where the device 10 includes a predetermined amount of clips, e.g., seventeen clips, the trigger 16 can be actuated seventeen times. Once the last clip has been applied, the stop, e.g., the third tang 82c, on the feeder shoe 34 can engage the stop tang 118 on the clip track 30 to prevent further distal movement of the feeder shoe 34.

The feeder shoe 34, feed bar 38, and/or the clip track 30 can also optionally include features to prevent accidental or unintentional movement of the feeder shoe 34, for example during shipment of the device. This is particularly advantageous as migration of the feeder shoe 34, particularly prior to first use of the device, can cause the device to malfunction. For example, if the feeder shoe 34 migrates distally, the feeder shoe 34 will advance two clips into the jaws simultaneously, thereby resulting in delivery of two misformed clips. Accordingly, in an exemplary embodiment the feeder shoe 34, feed bar 38, and/or the clip track 30 can include an engagement mechanism and/or can be configured to generate a frictional force therebetween that is sufficient to resist movement, but that can be overcome by actuation of the trigger 16 to allow the feed bar to advance the feeder shoe 34 through the clip track 30.

Figure 27A:
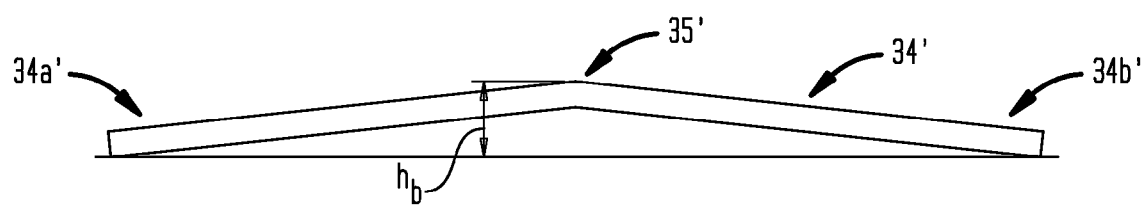
FIG. 27A is a side view illustration showing another embodiment of a feeder shoe having a pre-formed A-shaped bend formed therein and configured to create friction between the feeder shoe and the clip track.

While various techniques can be used to prevent undesirable migration of the feeder shoe 34 within the clip track 30, FIGS. 27A-29C illustrate various exemplary embodiments of techniques for creating friction or an engagement mechanism between the feeder shoe 34, feed bar 38, and/or the clip track 30. Referring first to FIG. 27A, one exemplary embodiment of a feeder shoe 34' is shown having a pre-formed cantilevered or bowed configuration in a free state (i.e., when the feeder shoe 34' is removed from the clip track 30) such that the feeder shoe 34' forms a cantilevered spring when disposed within the clip track 30. In particular, a portion of the feeder shoe 34' can include a bend 35' formed therein such that the opposed ends 34a', 34b' of the feeder shoe 34' are angled relative to one another. The bend 35' can cause the height $h_b$ of the feeder shoe 34' to be greater than the height of the clip track 30. While the height $h_b$ can vary, in an exemplary embodiment the bend 35' is configured to increase a height of the feeder shoe 34' by an amount that is sufficient to create a frictional drag force between the feeder shoe 34' and the clip track 30, but that still allows the feeder shoe 34' to slide within the clip track 30 when the trigger 16 is actuated. In an exemplary embodiment, the height of the feeder shoe 34' is increased at least about 30%, or more preferably about 40%. In use, the clip track 30 will force the feeder shoe 34' into a substantially planar configuration such that the feeder shoe 34' is biased against the clip track 30 when disposed therein. The bend 35' of the feeder shoe 34', as well as the terminal ends 34a', 34b' of the feeder shoe 34', will therefore apply a force to the clip track 30, thereby creating a frictional drag force between the feeder shoe 34' and the clip track 30. The frictional force will prevent the feeder shoe 34' from migrating relative to the clip track 30 unless the trigger 16 is actuated, in which case the force applied by the trigger 16 will overcome the frictional forces.

Figure 27B:
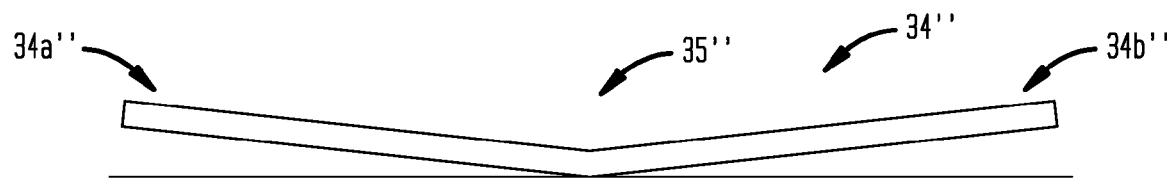
FIG. 27B is a side view illustration of another embodiment of a feeder shoe having a pre-formed V-shaped bend formed therein and configured to create friction between the feeder shoe and the clip track.

A person skilled in the art will appreciate that the bend 35' can have a variety of configurations, and it can be formed anywhere along the length of the feeder shoe 34'. In FIG. 27A the bend 35' is formed at or near the mid-portion of the feeder shoe 34'. The bend 35' can also extend in various directions. While FIG. 27A illustrates the bend 35' extending in a direction perpendicular to the axis such that the bend 35' and the ends 34a', 34b' apply a force to the clip track 30, the bend 35' can alternatively extend along a longitudinal axis of the feeder shoe 34' such that the feeder shoe 34' applies a force to the opposed side rails 80a, 80b (FIG. 2D) of the clip track 30. The bend 35' can also angle the opposed ends 34a', 34b' in a downward direction, as shown in FIG. 27A, such that the feeder shoe 34' is substantially A-shaped, or alternatively the bend 35" can angle the opposed ends 34a", 34b" in an upward direction, as shown in FIG. 27B, such that the feeder shoe 34" is substantially V-shaped. The feeder shoe 34' can also include any number of bends formed therein. A person skilled in the art will appreciate that the particular configuration of the bend(s) can be modified based on the properties of the feeder shoe 34' and the clip track 30 to obtain a desired amount of frictional force therebetween.

Figure 28A:
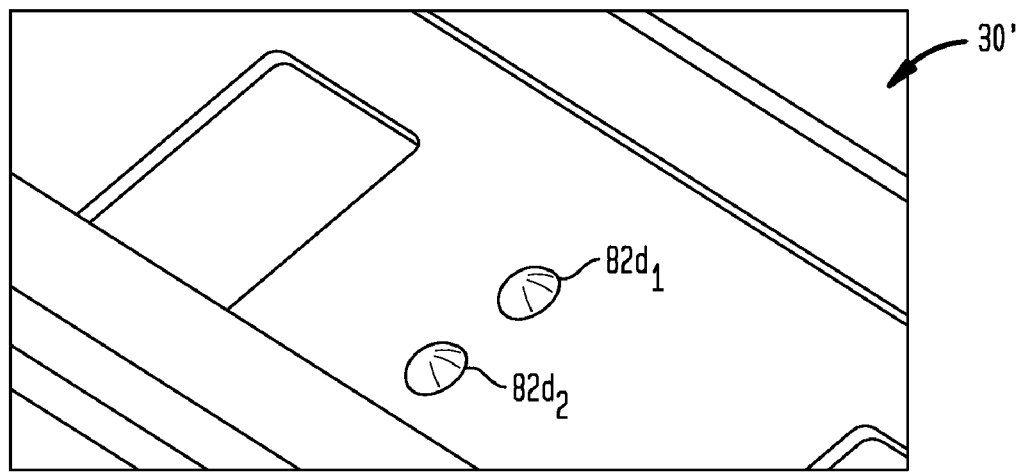
FIG. 28A is a perspective top view of a portion of a clip track having surface protrusions formed therein and configured to create friction between with the feeder shoe according to another embodiment of the invention.
Figure 28B:
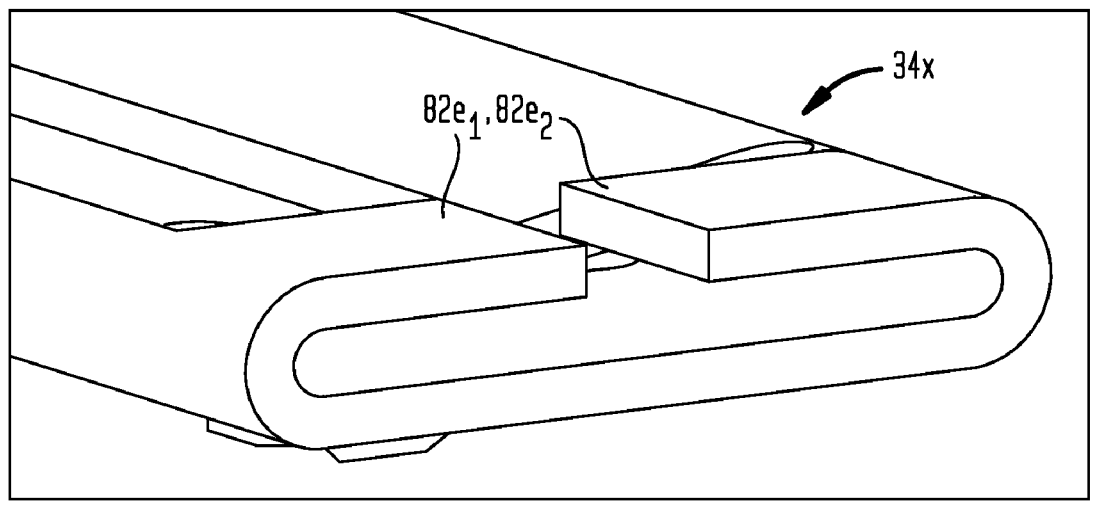
FIG. 28B is perspective end view of another embodiment of a feeder shoe having a tang formed thereon and adapted to engage the surface protrusions formed in the clip track shown in FIG. 28A.

FIGS. 28A and 28B illustrate another embodiment of a technique for creating frictional forces between the feeder shoe and clip track. In this embodiment, the clip track 30' and/or the feeder shoe $34_x$ can include one or more surface protrusions formed thereon. As shown in FIG. 28A, two surface protrusions $82d_1$, $82d_2$ are formed on the clip track 30'. While the surface protrusions $82d_1$, $82d_2$ can be formed at various locations on the clip track 30', including inside the opposed side rails or along the entire length of the clip track 30', or at various locations on the feeder shoe $34_x$, in the illustrated embodiment two protrusions $82d_1$, $82d_2$ are formed adjacent to the proximal end of the clip track 30' and they are positioned to prevent initial migration of the feeder shoe prior to use, e.g., during shipping. The size of the protrusions $82d_1$, $82d_2$ can vary depending upon the amount of frictional force necessary to prevent unintentional migration of the feeder shoe $34_x$.

While the protrusions $82d_1$, $82d_2$ can be configured to provide a sufficient amount of friction to prevent unintentional migration of the feeder shoe $34_x$, the feeder shoe $34_x$ and/or clip track 30' can optionally include a feature that is adapted to engage corresponding surface protrusions. FIG. 28B illustrates opposed tangs $82e_1$, $82e_2$ formed on a distal portion of the feeder shoe $34_x$ for engaging the protrusions $82d_1$, $82d_2$ on the clip track 30'. The tangs $82e_1$, $82e_2$ can vary in shape and size, and they can include a lip or other protrusion configured to engage or "catch" the protrusions $82d_1$, $82d_2$. As shown in FIG. 28B, the tangs $82e_1$, $82e_2$ extend toward one another from opposed sidewalls of the feeder show $34_x$.

Figure 29A:
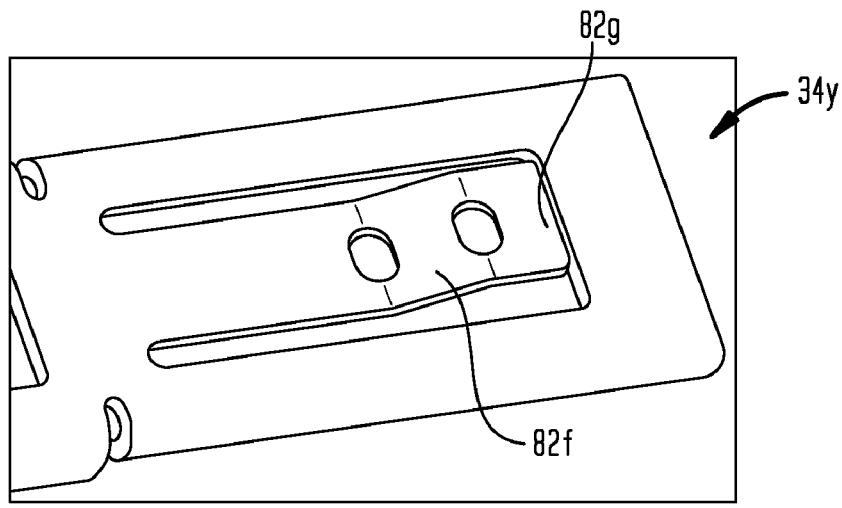
FIG. 29A is a bottom perspective view of another embodiment of a feeder shoe having a holdback lip formed on a tang that is adapted to engage a corresponding groove formed in a feed bar.
Figure 29B:
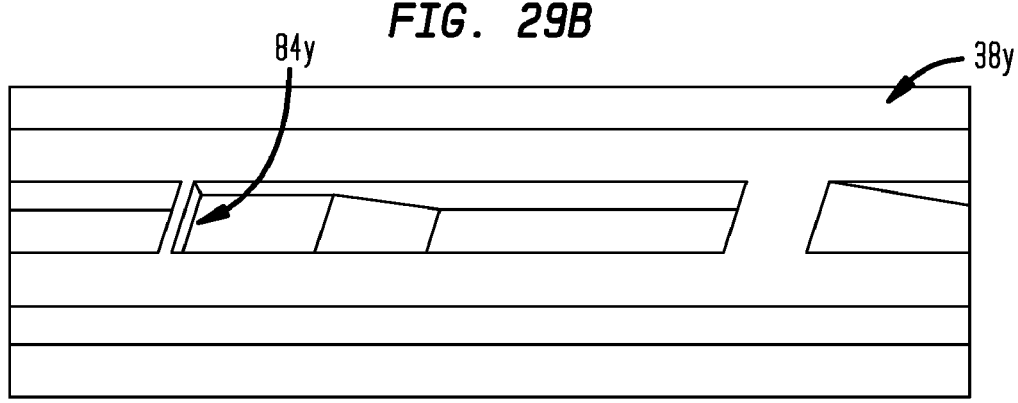
FIG. 29B is a top perspective view of another embodiment of a feed bar having a catch groove formed therein and adapted to be engaged by the holdback lip formed on the tang of the feeder shoe shown in FIG. 29A.
Figure 29C:
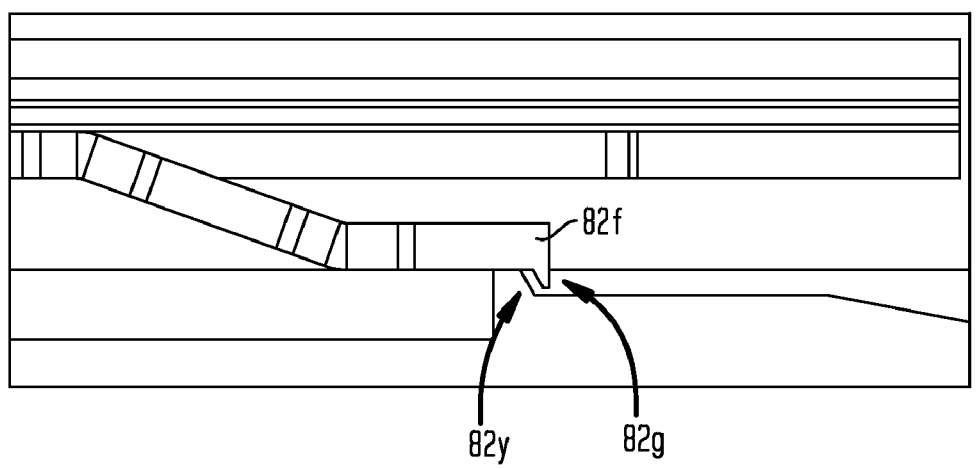
FIG. 29C is a side cross-sectional view of the feeder shoe of FIG. 29A disposed within and engaging the feed bar of FIG. 29B.

FIGS. 29A-29C illustrate another embodiment of a technique for preventing unintentional migration of the feeder shoe. In this embodiment, friction is generated between the feeder shoe and the feed bar. In particular, the feeder shoe $34_y$ includes a tang $82_f$ with a lip $82_g$ formed thereon, as shown in FIG. 29A, and the feed bar $38_y$ includes a corresponding groove $84_y$ formed therein. In use, as shown in FIG. 29C, the lip $82_g$ is configured to engage the groove $84_y$ to prevent unintentional migration of the feeder shoe $34_y$. The lip $82_g$ and groove $84_y$, however, are configured to allow movement of the feeder shoe 34y when a sufficient force is applied to the feeder shoe $34_y$ by actuation of the trigger 16.

A person skilled in the art will appreciate that a variety of other techniques can be used to prevent unintentional migration of a feeder shoe or other clip advancement mechanism within a clip track, and that any combination of features can be used and positioned at various locations on one or both components.

Figure 7:
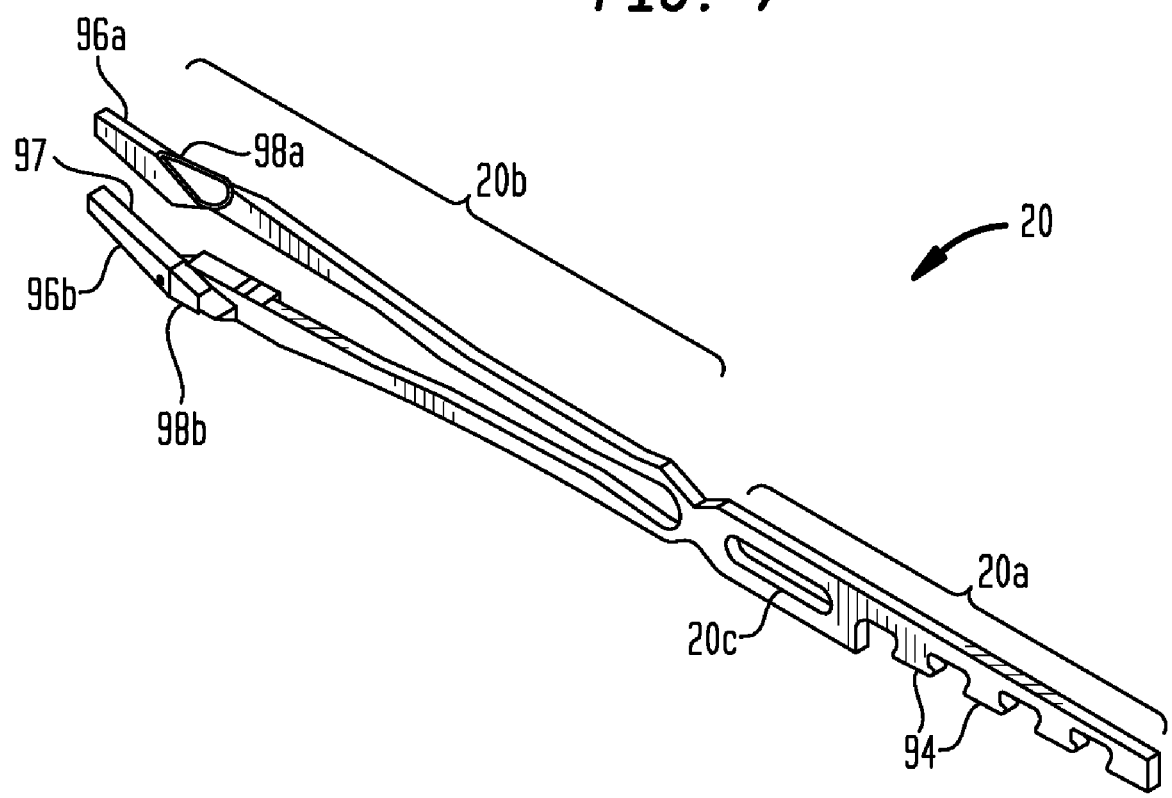
FIG. 7 is a side perspective view of a pair of jaws of the surgical clip applier shown in FIG. 1A.
Figure 8:
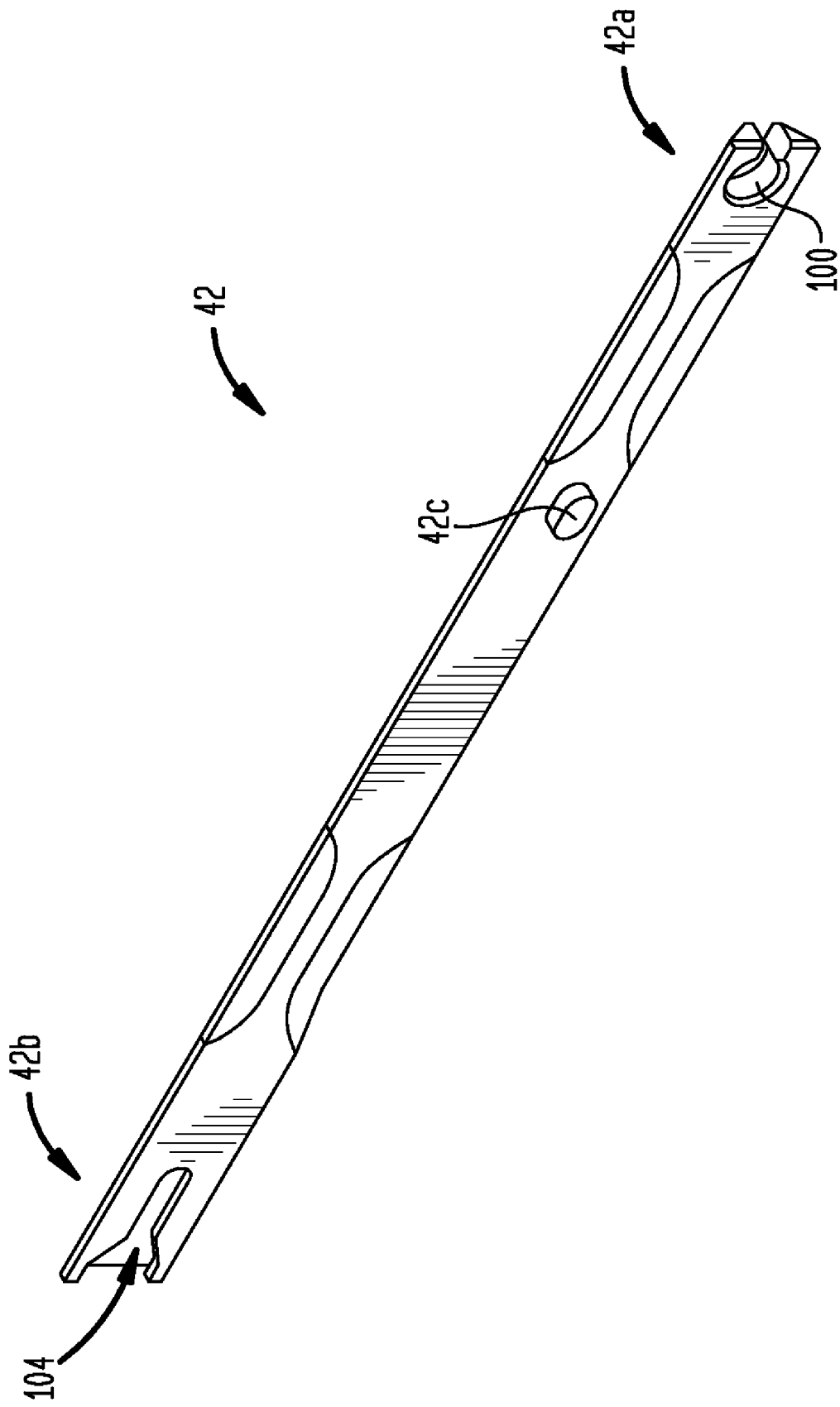
FIG. 8 is a side perspective view of a cam for use with the jaws shown in FIG. 7.

FIGS. 7-9 illustrate various exemplary components of a clip forming assembly. Referring first to FIG. 7, an exemplary embodiment of the jaws 20 are shown. As previously mentioned, the jaws 20 can include a proximal portion 20a having teeth 94 for mating with corresponding teeth 78 formed on the jaw retaining shaft 28. Other techniques can, however, be used to mate the jaws 20 to the jaw retaining shaft 28. For example, a dovetail connection, a male-female connection, etc., can be used. Alternatively, the jaws 20 can be integrally formed with the retaining shaft 28. The distal portion 20b of the jaws 20 can be adapted to receive a clip therebetween, and thus the distal portion 20b can include first and second opposed jaw members 96a, 96b that are movable relative to one another. In an exemplary embodiment, the jaw members 96a, 96b are biased to an open position, and a force is required to move the jaw members 96a, 96b toward one another. The jaw members 96a, 96b can each include a groove (only one groove 97 is shown) formed therein on opposed inner surfaces thereof for receiving the legs of a clip in alignment with the jaw members 96a, 96b. The jaws members 96a, 96b can also each include a cam track 98a, 98b formed therein for allowing the cam 42 to engage the jaw members 96a, 96b and move the jaw members 96a, 96b toward one another. In an exemplary embodiment, the cam track 98a, 98b is formed on a superior surface of the jaw members 96a, 96b.

FIG. 8 illustrates an exemplary cam 42 for slidably mating to and engaging the jaw members 96, 96b. The cam 42 can have a variety of configurations, but in the illustrated embodiment it includes a proximal end 42a that is adapted to mate to a push rod 44, discussed in more detail below, and a distal end 42b that is adapted to engage the jaw members 96a, 96b. A variety of techniques can be used to mate the cam 42 to the push rod 44, but in the illustrated exemplary embodiment the cam 42 includes a female or keyed cut-out 100 formed therein and adapted to receive a male or key member 102 formed on the distal end 44b of the push rod 44. The male member 102 is shown in more detail in FIG. 9, which illustrates the push rod 44. As shown, the male member 102 has a shape that corresponds to the shape of the cut-out 100 to allow the two members 42, 44 to mate. A person skilled in the art will appreciate that the cam 42 and the push rod 44 can optionally be integrally formed with one another. The proximal end 44a of the push rod 44 can be adapted to mate to a closure link assembly, discussed in more detail below, for moving the push rod 44 and the cam 42 relative to the jaws 20.

As is further shown in FIG. 8, the cam 42 can also include a protrusion 42c formed thereon that is adapted to be slidably received within an elongate slot 20c formed in the jaws 20. In use, the protrusion 42c and the slot 20c can function to form a proximal stop for the clip forming assembly.

Figure 10A:
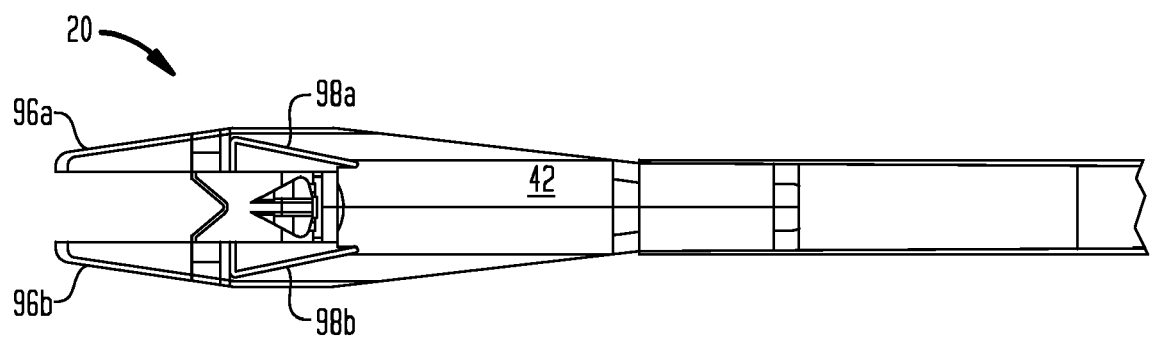
FIG. 10A is a top view of the cam shown in FIG. 8 coupled to the jaws shown in FIG. 7, showing the cam in an initial position and the jaws open.
Figure 10B:
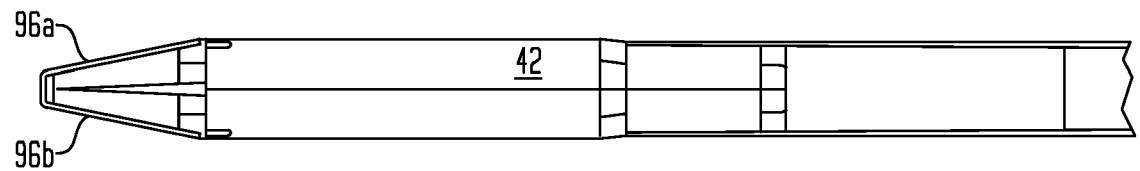
FIG. 10B is a top view of the cam shown in FIG. 8 coupled to the jaws shown in FIG. 7, showing the cam advanced over the jaws and the jaws in a closed position.

Referring back to FIG. 8, the distal end 42b of the cam 42 can be adapted to engage the jaw members 96a, 96b. While a variety of techniques can be used, in the illustrated exemplary embodiment the distal end 42b includes a camming channel or tapering recess 104 formed therein for slidably receiving the cam tracks 98a, 98b on the jaw members 96a, 96b. In use, as shown in FIGS. 10A and 10B, the cam 42 can be advanced from a proximal position, in which the jaw members 96a, 96b are spaced a distance apart from one another, to a distal position, in which the jaw members 96a, 96b are positioned adjacent to one another and in a closed position. As the cam 42 is advanced over the jaw members 96a, 96b, the tapering recess 104 will push the jaw members 96a, 96b toward one another, thereby crimping a clip disposed therebetween.

Figure 11A:
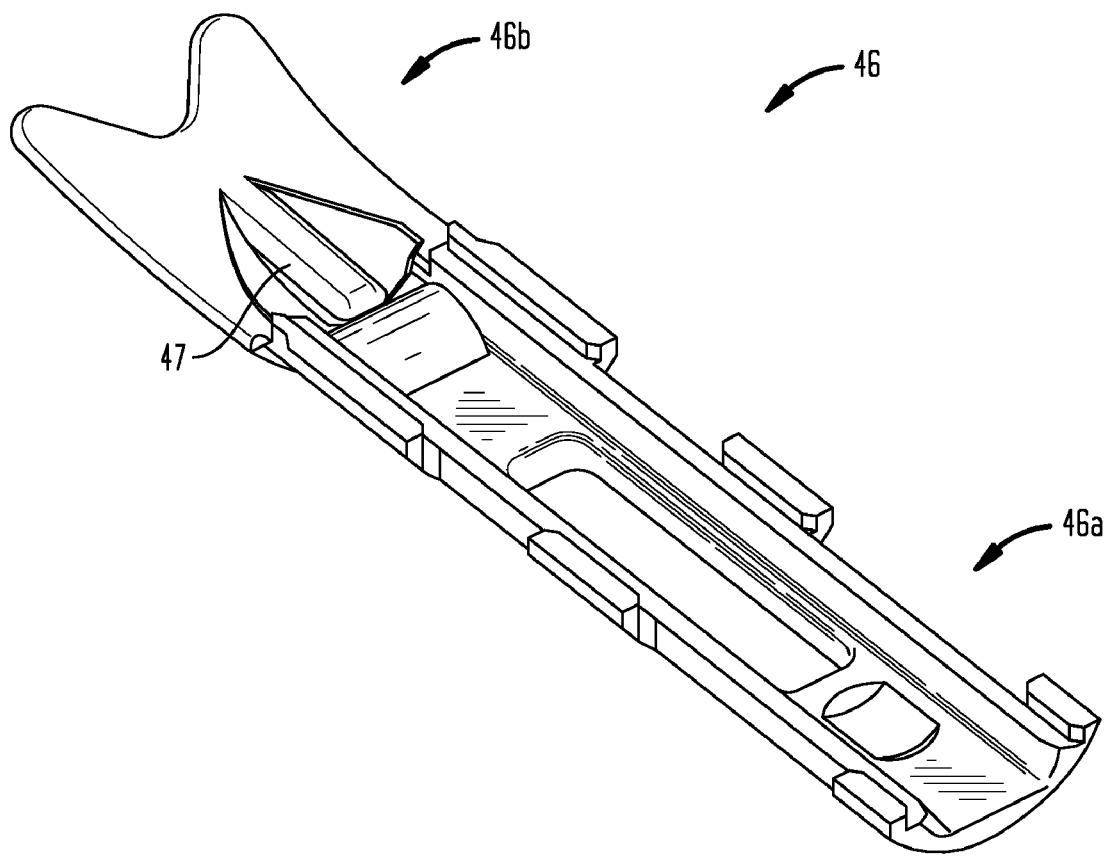
FIG. 11A is a top perspective view of a tissue stop that is adapted to couple to a distal end of the clip track of the jaw retainer assembly shown in FIGS. 2A-2D.

As previously mentioned, the surgical clip applier 10 can also include a tissue stop 46 for facilitating positioning of the tissue at the surgical site within jaws 20. FIG. 11A shows one exemplary embodiment of a tissue stop 46 having proximal end and distal ends 46a, 46b. The proximal end 46a can be adapted to mate to a distal end of the clip track 30 for positioning the tissue stop 46 adjacent to the jaws 20. However, the tissue stop 46 can be integrally formed with the clip track 30, or it can be adapted to mate to or be integrally formed with a variety of other components of the shaft 18. The distal end 46b of the tissue stop 46 can have a shape that is adapted to seat a vessel, duct, shunt, etc. therebetween to position and aligned the jaws 20 relative to the target site. As shown in FIG. 11A the distal end 46b of the tissue stop 46 is substantially v-shaped. The distal end 46b can also have a curved configuration to facilitate placement of the device through a trocar or other access tube.

The tissue stop, or other components of the device, can also optionally include features to support and stabilize a clip during clip formation. When a clip is being formed between the jaws, the clip can pivot and become misaligned. In particular, as the jaws are closed, the terminal end of each leg of the clip will be moved toward one another. As a result, the jaws will only engage a bend portion on each leg, thus allowing the terminal ends of the legs and the apex of the clip to swing out of alignment with the jaws, i.e., to pivot vertically relative to the jaws. Further closure of the jaws can thus result in a malformed clip. Accordingly, the device can include features to align and guide the clip into the jaws, and to prevent the clip from pivoting or otherwise becoming misaligned during clip formation.

While the alignment feature can have a variety of configurations, and it can be formed on various components of the device, FIG. 11A illustrates a central tang 47 formed at a mid-portion of the distal end 46b of the tissue stop 46 for maintaining a clip in alignment with the tip of the advancer assembly 40. In particular, the central tang 47 can allow the apex of a clip to ride therealong thus preventing the clip from becoming misaligned relative to the advancer assembly 40 that is pushing the clip in a distal direction. A person skilled in the art will appreciate that the tissue stop 46 can have a variety of other configurations, and it can include a variety of other features to facilitate advancement of a clip therealong.

Figure 11B:
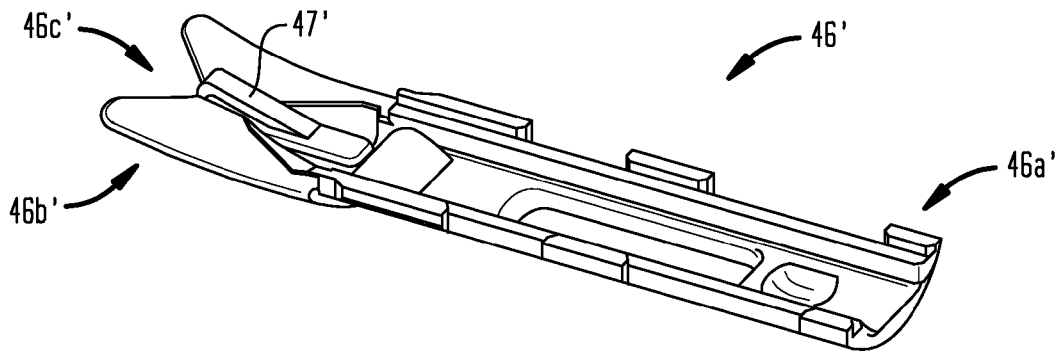
FIG. 11B is a top perspective view of another embodiment of a tissue stop having a ramp formed thereon for guiding a clip into the jaws and stabilizing the clip during clip formation.
Figure 11C:
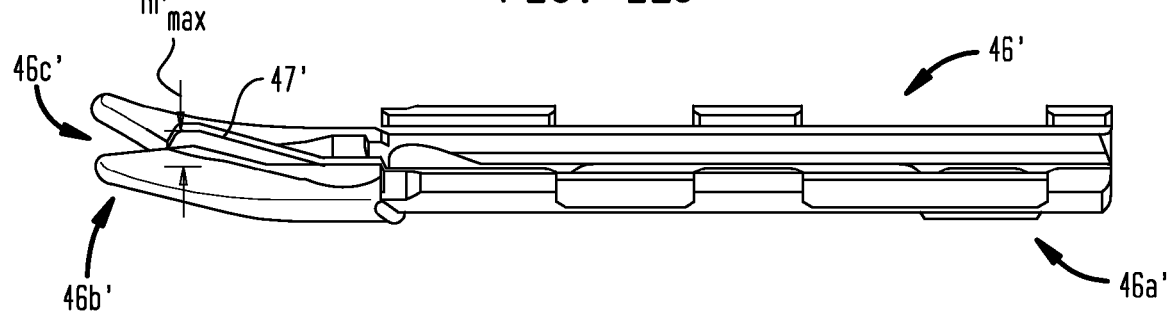
FIG. 11C is a side view of the tissue stop shown in FIG. 11B.
Figure 11D:
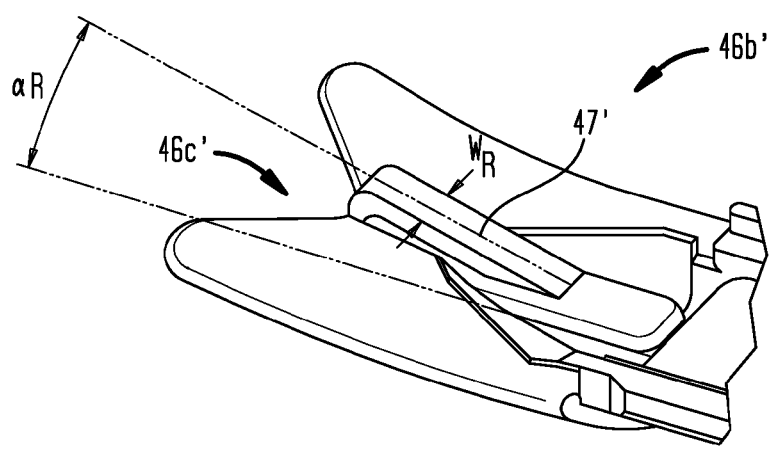
FIG. 11D is an enlarged view of the tissue stop shown in FIGS. 11B and 11C.

FIGS. 11B-11D illustrate another exemplary embodiment of a tissue stop 46' having an alignment feature or guide member formed thereon and adapted to align and guide the clip into the jaws, and more preferably to maintain the clip in alignment with the jaws during clip formation. In this embodiment, the alignment feature is in the form of a ramped member 47' extending longitudinally along a central axis of the tissue stop 46' and protruding above a superior surface of the tissue stop 46'. The ramped member 47' is preferably rigid, and increases in height from a proximal end 46a' to a distal end 46b' of the tissue stop 46'. The angle can vary, however, depending on the particular angle of the jaws. The ramp member 47' preferably terminates just proximal to the tissue-receiving recess 46c' formed in the distal tip of the tissue stop 46'. As a result, the ramped member 47' is positioned just proximal to the jaws 20, thus allowing the ramped member 47' to guide a clip, as well as the tip of the advancer assembly 40 that is pushing the clip, into the jaws 20 at an appropriate angle. In use, the ramped member 47' can abut against an inferior surface of the apex of a clip disposed between the jaws 20 to prevent the clip from pivoting vertically as the jaws 20 are closed to form the clip. In particular, when the advancer assembly 40 is moved to the distal-most position along the ramped member 47', the apex of the clip will abut against the surface of the ramped member 47'. As the clip is compressed between the jaws 20 and the legs of the clip move toward one another, the jaws 20 will only engage a bend portion on each leg. As a result, legs and the apex of the clip are free to pivot vertically. However, since the apex is resting against the superior surface 47a' of the ramped member 47', the ramped member 47' will prevent the apex from moving vertically in a downward or inferior direction, thereby preventing the legs of the clip from moving vertically in an upward or superior direction, i.e., the ramped member 47' will prevent the clip from swinging within the jaws 20. Thus, the ramped member 47' is effective to prevent or limit harmful rotational forces generated when the jaws 20 are closed to form the clip. The clip is thus maintained in alignment with the jaws 20.

A person skilled in the art will appreciate that the shape, size, and configuration of the ramp member can vary depending on the particular configuration of the jaws and other components of the clip applier. In one exemplary embodiment, the ramped member 47' can have a maximum height $h_{Rmax}$ of about 0.025", as measured from a central plane extending through the tissue stop 46'. More preferably the height $h_{Rmax}$ is in the range of about 0.008" to 0.020", and most preferably the height $h_{Rmax}$ is in the range of about 0.010" to 0.015". The incline angle $\alpha_R$ of the ramped member 47' can also vary, but in an exemplary embodiment the ramped member 47' has an incline angle $\alpha_R$ in the range of about 5° to 45°, and more preferably 5° to 30°, and most preferably 10° to 20°. The width $w_r$ of the ramped member 47' can also vary, but in an exemplary embodiment the ramped member 47' preferably has a width $w_r$ that is slightly less than a space between the jaws 20 in the fully closed position.

Figure 12:
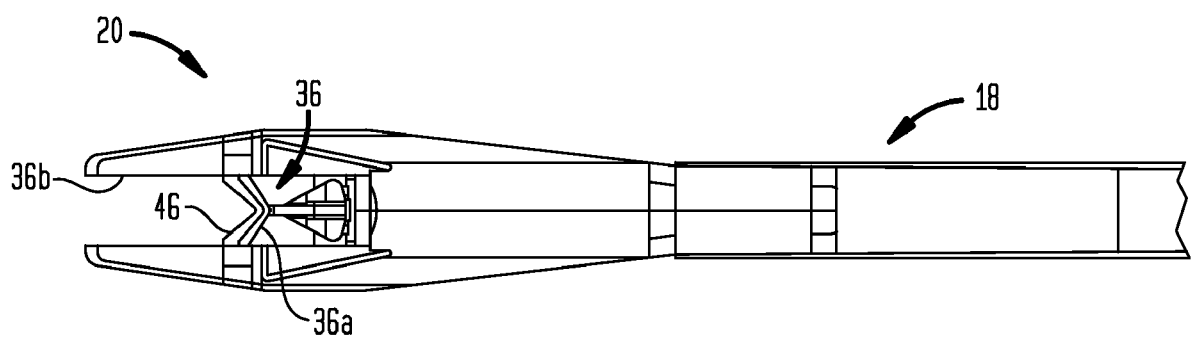
FIG. 12 is a top view of a distal end of the surgical clip applier shown in FIG. 1A showing the tissue stop shown in FIG. 11A positioned between the jaws shown in FIG. 7.
Figure 13:
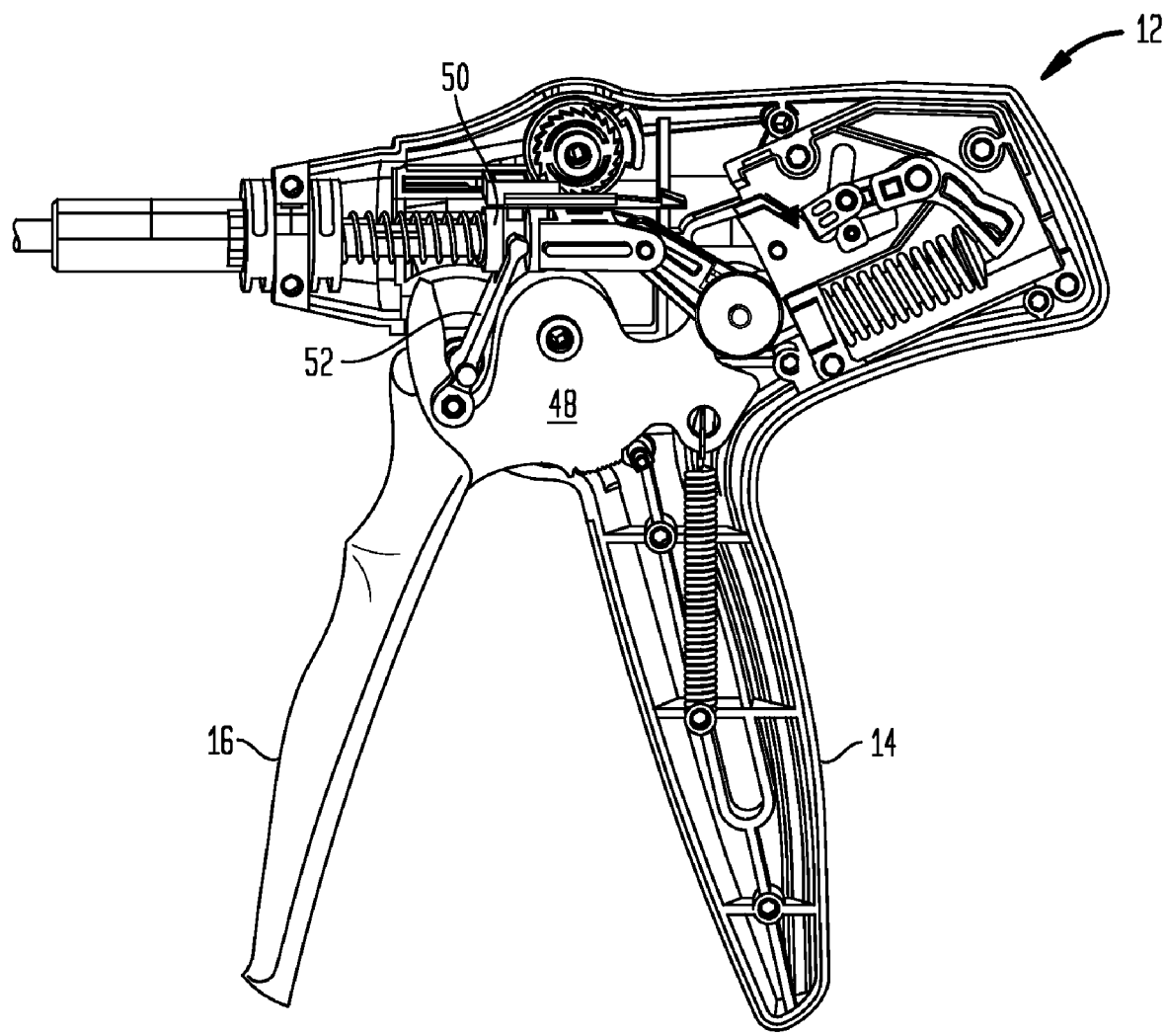
FIG. 13 is a side, partially cross-sectional view of the handle portion of the surgical clip applier shown in FIG. 1A.

FIG. 12 illustrates the tissue stop 46 in use. As shown, the tissue stop 46 is positioned just inferior to the jaws 20 and at a location that allows a vessel, duct, shunt etc. to be received between the jaws 20. As is further shown, a surgical clip 36 is positioned between the jaws 20 such that the bight portion 36a of the clip 36 is aligned with the tissue stop 46. This will allow the legs 36b of the clip 36 to be fully positioned around the vessel, duct, shunt, or other target site.

FIGS. 13-26B illustrate various exemplary internal components of the housing 12 for controlling clip advancement and forming. As previously discussed, the surgical clip applier 10 can include some or all of the features disclosed herein, and it can include a variety of other features known in the art. In certain exemplary embodiments, the internal components of the clip applier 10 can include a clip advancing assembly, that couples to the clip advancing assembly of the shaft 18, for advancing at least one clip through the elongate shaft 18 to position the clip between the jaws 20, and a clip forming assembly, that couples to the clip forming assembly of the shaft 18, for closing the jaws 20 to form a partially or fully closed clip. Other exemplary features include an antibackup mechanism for controlling movement of the trigger 16, an overload mechanism for preventing overload of the force applied to the jaws 20 by the clip forming assembly, and a clip quantity indicator for indicating a quantity of clips remaining in the device 10.

FIGS. 13-16D illustrate an exemplary embodiment of a clip advancing assembly of the housing 12 for effecting movement of the feed bar 38 within the shaft 18. In general, the clip advancing assembly can include a trigger insert 48 that is coupled to the trigger 16, a feed bar coupler 50 that can mate to a proximal end 38a of the feed bar 38, and a feed link 52 that is adapted to extend between the trigger insert 48 and the feed bar coupler 50 for transferring motion from the trigger insert 48 to the feed bar coupler 50.

Figure 14:
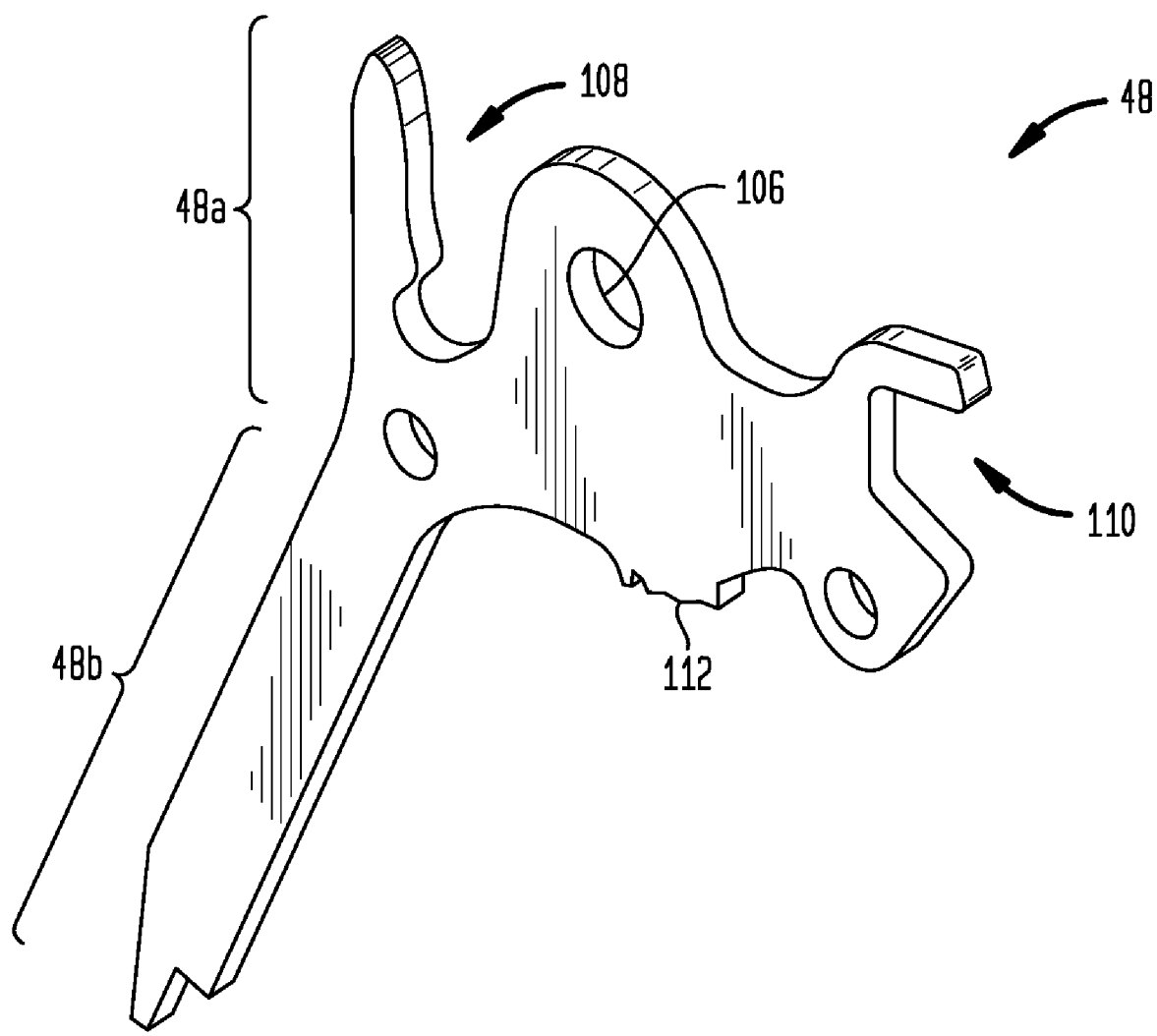
FIG. 14 is a side perspective view of a trigger insert of the surgical clip applier shown in FIG. 1A.

FIG. 14 illustrates the trigger insert 48 in more detail. The shape of the trigger insert 48 can vary depending on the other components of the housing 12, but in the illustrated embodiment the trigger insert 48 includes a central portion 48a that is adapted to pivotally mate to the housing 12, and an elongate portion 48b that is adapted to extend into and mate to the trigger 16. The central portion 48a can include a bore 106 extending therethrough for receiving a shaft for pivotally mating the trigger insert 48 to the housing 12. The central portion 48a can also include a first recess 108 formed in a superior side edge for receiving a portion of the feed link 52. The first recess 108 preferably has a size and shape that allows a portion of the feed link 52 to extend therein such that the feed link 52 will be forced to pivot when the trigger insert 48 pivots due to movement of the trigger 16. As shown in FIG. 14, the first recess 108 is substantially elongate and includes a substantially circular portion formed therein for seating a shaft formed on a proximal end of the feed link 52, as will be discussed in more detail with respect to FIG. 16. The trigger insert 48 can also include a second recess 110 formed in a back side edge for receiving a closure link roller 54 that is coupled to the push bar 44 for moving the cam 42 to close the jaws 20, and ratchet teeth 112 formed on the bottom side edge thereof for mating with a pawl 60 for controlling movement of the trigger 16, as will be discussed in more detail below.

Figure 15A:
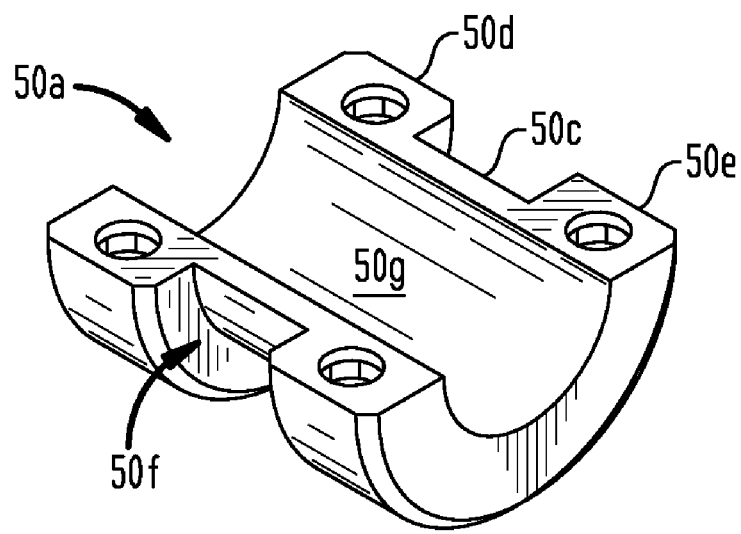
FIG. 15A is a side perspective view of one half of a feed bar coupler of the surgical clip applier shown in FIG. 1A.
Figure 15B:
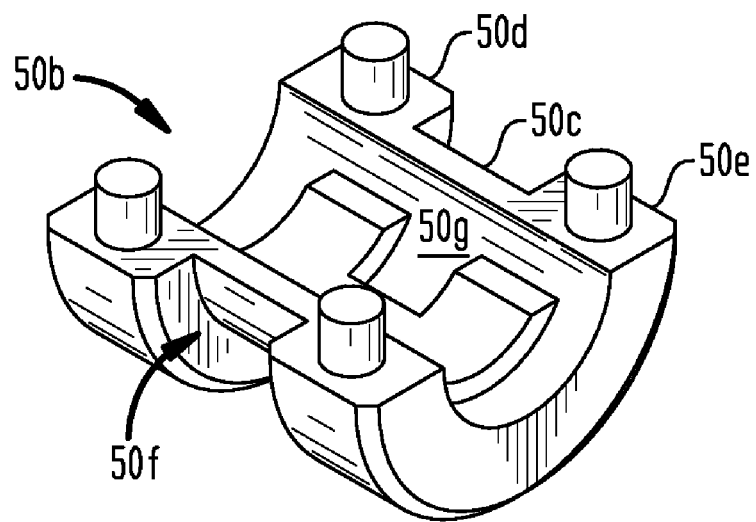
FIG. 15B is a side perspective view of the other half of the feed bar coupler shown in FIG. 15A.

The exemplary feed bar coupler 50 is shown in more detail in FIGS. 15A and 15B, and it can be adapted to couple the proximal end of the feed bar 38 to the distal end of the feed link 52. While a variety of techniques can be used to mate the feed bar coupler 50 to the proximal end 38a of the feed bar 38, in an exemplary embodiment the feed bar coupler 50 is formed from two separate halves 50a, 50b that mate together to maintain the proximal end 38a of the feed bar 38 therebetween. When mated, the two halves 50a, 50b together define a central shaft 50c having substantially circular flanges 50d, 50e formed on opposed ends thereof and defining a recess 50f therebetween for seating a distal portion of the feed link 52. The central shaft 50c defines a lumen 50g therethrough for receiving the proximal end 38a of the feed bar 38 and for locking the feed bar 38 in a substantially fixed position relative to the feed bar coupler 50. The feed bar coupler 50 can, however, be integrally formed with the feed bar 38, and it can have a variety of other shapes and sizes to facilitate mating with the feed link 52.

Figure 16:
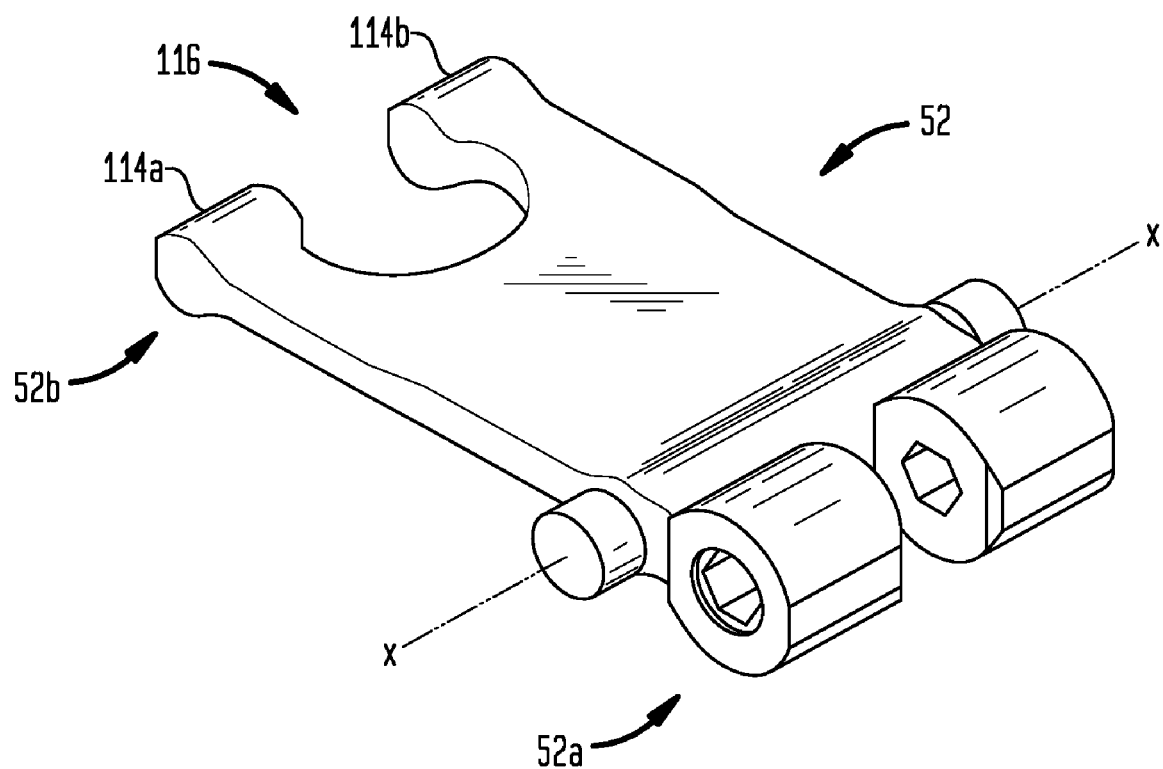
FIG. 16 is a top perspective view of a flexible link that forms part of a clip advancing assembly of the surgical clip applier shown in FIG. 1A.

FIG. 16 illustrates an exemplary feed link 52, which can extend between the trigger insert 48 and the feed bar coupler 52. In general, the feed link 52 can have a substantially planar elongate shape with proximal and distal ends 52a, 52b. The proximal end 52a is adapted to rotatably sit within the first recess 108 of the trigger insert 48 and thus, as previously discussed, it can include a shaft 53 (FIG. 1B) extending therethrough. The shaft 53 can be adapted to pivotally rotate within the first recess 108 of the trigger insert 48, thereby allowing the trigger insert 48 to pivot the feed link 52. The distal end 52b of the feed link 52 can be adapted to couple to feed bar coupler 50 and thus, in an exemplary embodiment, it includes opposed arms 114a, 114b formed thereon and defining an opening 116 therebetween for seating the central shaft 50a of the feed bar coupler 50. The arms 114a, 114b are effective to engage and move the coupler 50 as the feed link 52 pivots about a pivot axis X. The pivot axis X can be defined by the location at which the feed link 52 couples to the housing 12, and it can be positioned anywhere on the feed link 52, but in the illustrated embodiment it is positioned adjacent to the proximal end 52a of the feed link 52.

In an exemplary embodiment, the feed link 52 can be flexible to eliminate the need to calibrate the clip advancing assembly and the clip forming assembly. In particular, the feed link 52 allows the trigger 16 to continue moving toward a closed position even after the feed bar 38 and feed bar coupler 50 are in a distal-most position, and it provides some freedom to the clip forming and clip advancing assemblies. In other words, the trigger 16 is pliant relative to the feed bar 38 during closure of the trigger.

The particular stiffness and strength of the feed link 52 can vary depending on the configuration of the clip advancing assembly and the clip forming assembly, but in one exemplary embodiment the feed link 52 has a stiffness that is in the range of 75 to 110 lbs per inch, and more preferably that is about 93 lbs per inch (as measured at the interface between the link 52 and the feed bar coupler 50), and it has a strength of that is in the range of 25 lbs and 50 lbs, and more preferably that is about 35 lbs. The feed link 52 can also be formed from a variety of materials, including a variety of polymers, metals, etc. One exemplary material is a glass-reinforced polyetherimide, but a number of reinforced thermoplastics could be used, including glass reinforced liquid-crystal polymers, glass-reinforced nylons, and carbon-fiber reinforced versions of these and similar thermoplastics. Fiber-reinforced thermoset polymers such as thermoset polyesters could also be used. Feed link 52 could also be fabricated from a metal, such as spring steel to achieve the desired combination of limited flexibility and controlled strength.

Figure 17A:
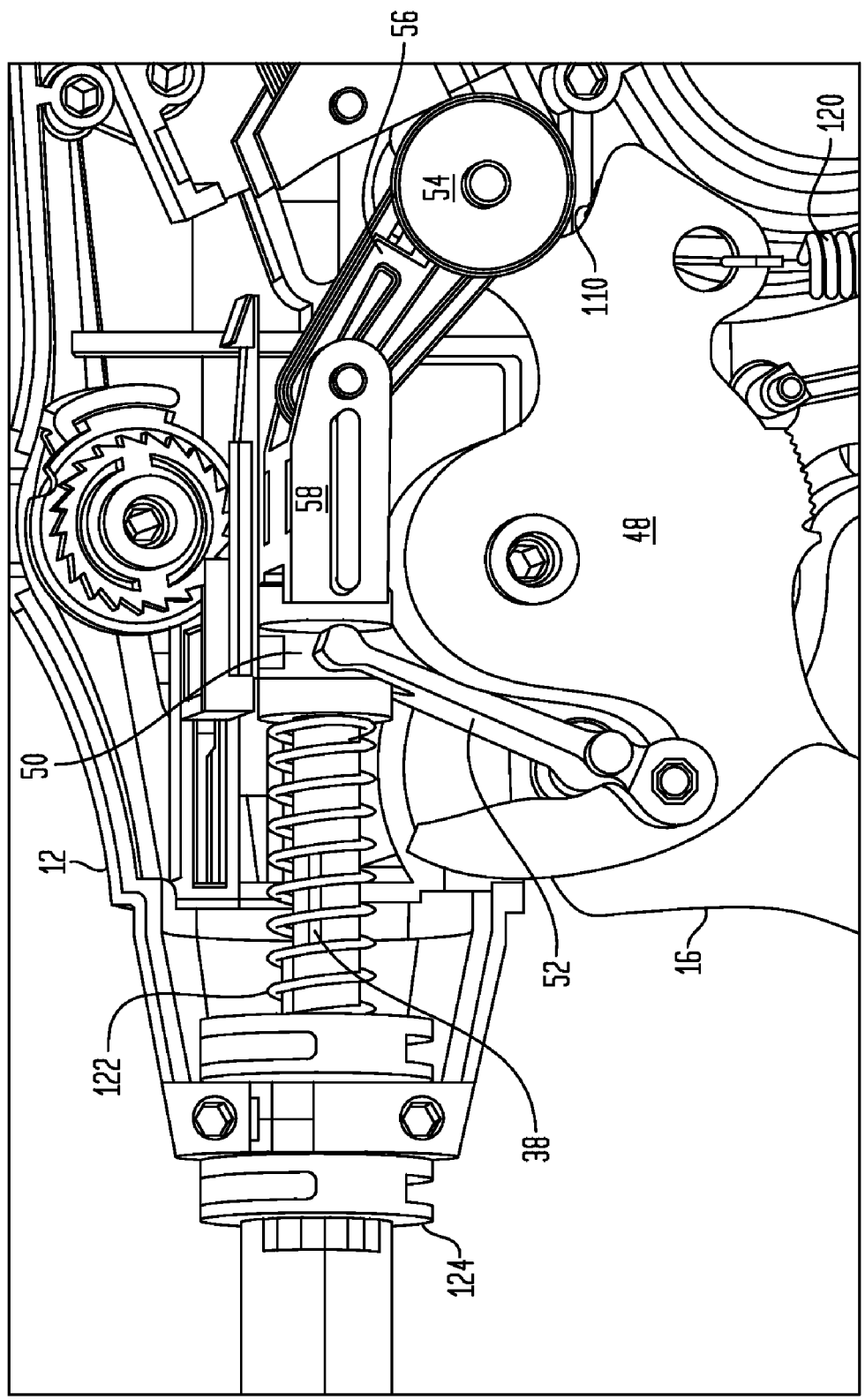
FIG. 17A is a side, partially cross-sectional view of a portion of the handle of the surgical clip applier shown in FIG. 1A, showing a clip advancing assembly in an initial position.

FIGS. 17A-17D illustrate the exemplary clip advancing assembly in use. FIG. 17A shows an initial position, wherein the trigger 16 is resting in an open position, the feed bar coupler 50 and feed bar 38 are in a proximal-most position, and the feed link 52 extends between the trigger insert 48 and the feed bar coupler 50. As previously discussed, in the initial open position the protrusion 86 on the feed bar 38 is positioned in the proximal end of the elongate slot 88 in the jaw retainer shaft 28. A first biasing member, e.g., spring 120, is coupled to the trigger insert 48 and the housing 12 to maintain the trigger insert 48 and trigger 16 in the open position, and a second biasing member, e.g., spring 122, extends between a shaft coupler 124, which rotatably mates the shaft 18 to the housing 12, and the feed bar coupler 50 to maintain the feed bar coupler 50 and feed bar 38 in the proximal-most position.

Figure 17B:
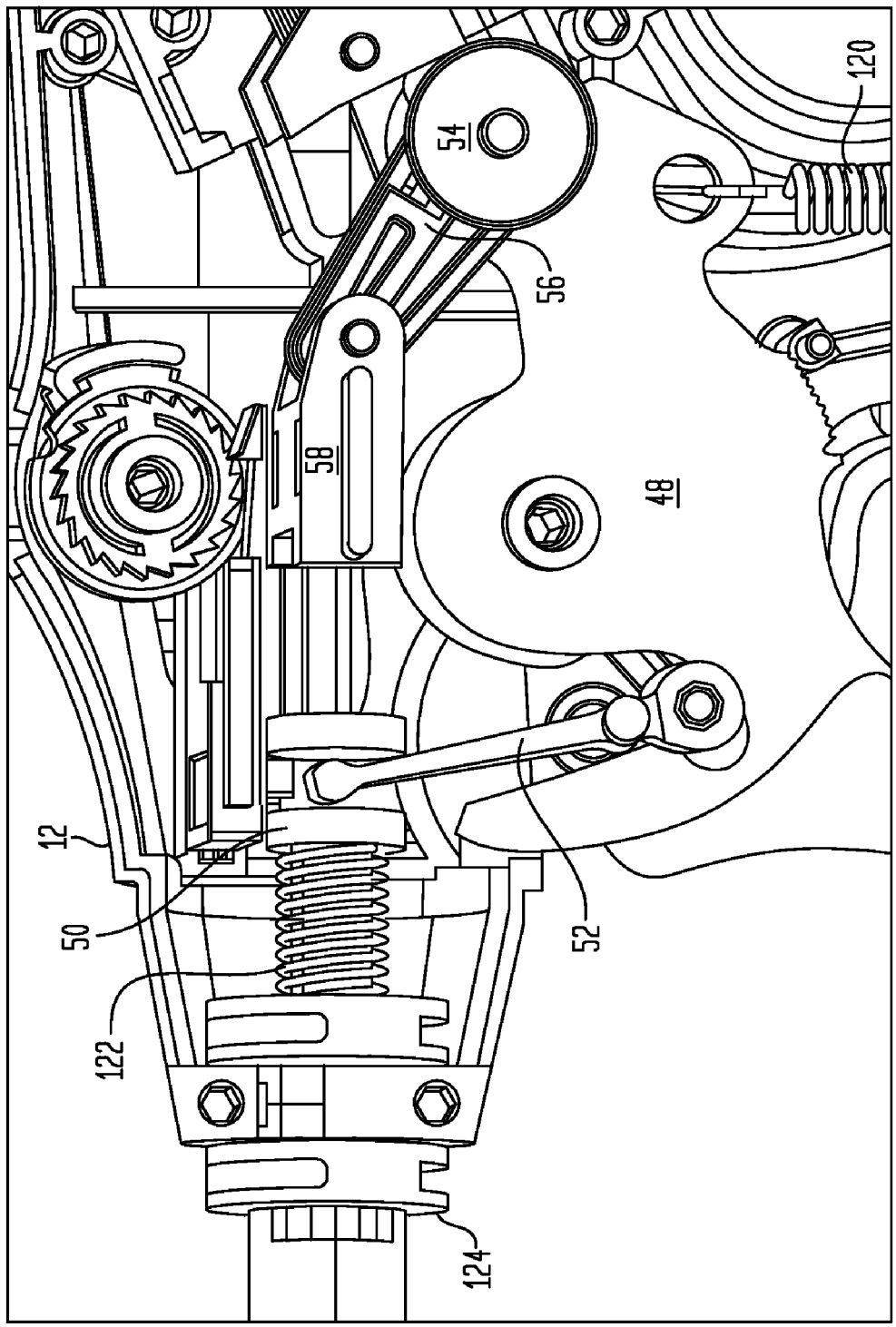
FIG. 17B is a side, partially cross-sectional view of a portion of the handle of the surgical clip applier shown in FIG. 17A, showing the clip advancing assembly partially actuated.

When the trigger 16 is actuated and moved toward the closed position, i.e., toward the stationary handle 14, to overcome the biasing forces applied by the springs 120, 122, the trigger insert 48 begins to pivot in a counter-clockwise direction, as shown in FIG. 17B. As a result, the feed link 52 is forced to pivot in a counter-clockwise direction, thereby moving the feed bar coupler 50 and feed bar 38 in a distal direction. The protrusion 86 on the feed bar 38 thus moves distally within the elongate slot 88 in the jaw retainer shaft 28, thereby advancing the feeder shoe 34 and the clips 36 disposed within the clip track. Spring 120 is extended between the housing and the trigger insert 48, and spring 122 is compressed between the feed bar coupler 50 and the shaft coupler 124.

Figure 17C:
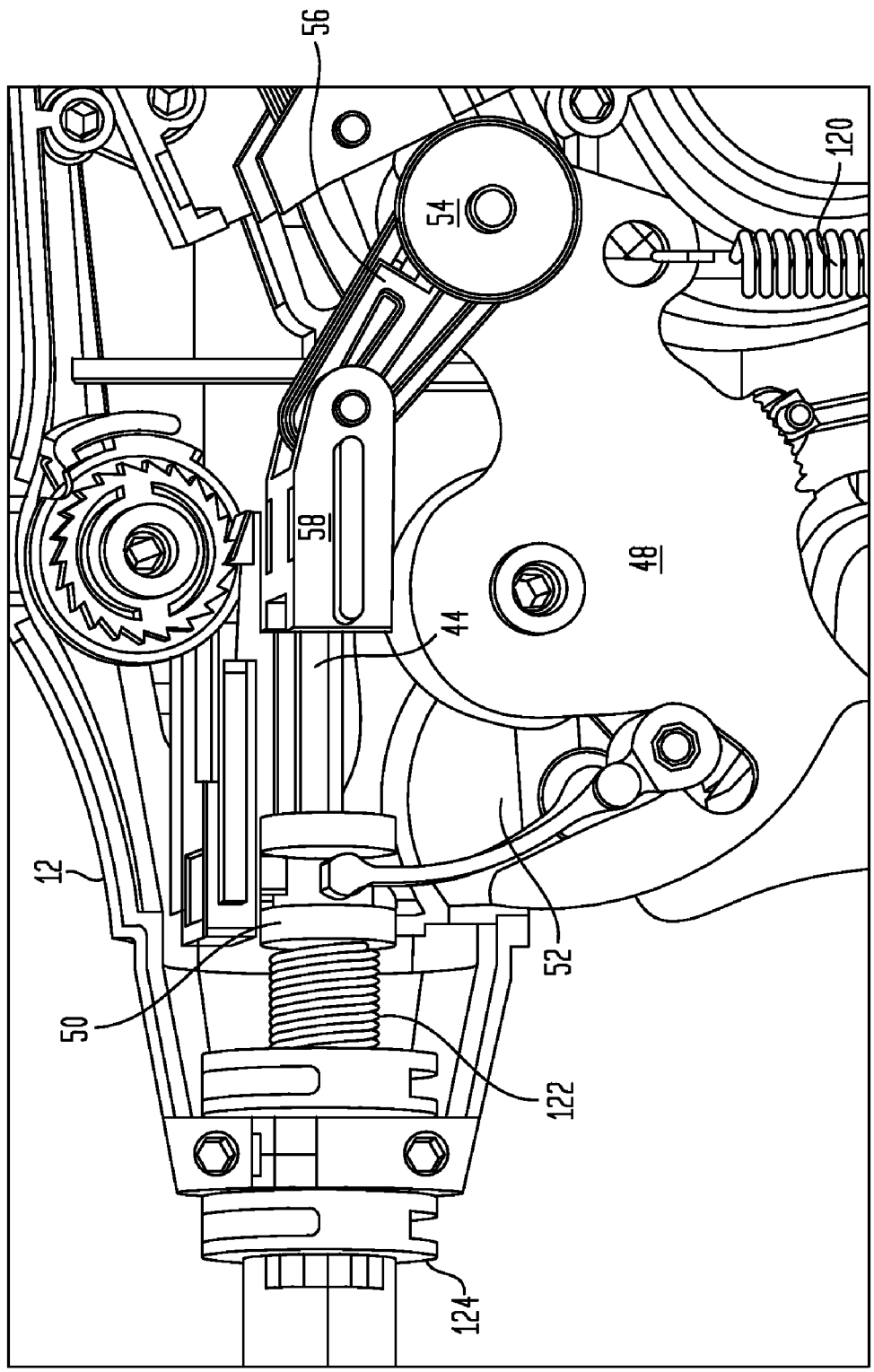
FIG. 17C is a side, partially cross-sectional view of a portion of the handle of the surgical clip applier shown in FIG. 17B, showing the clip advancing assembly fully actuated.
Figure 17D:
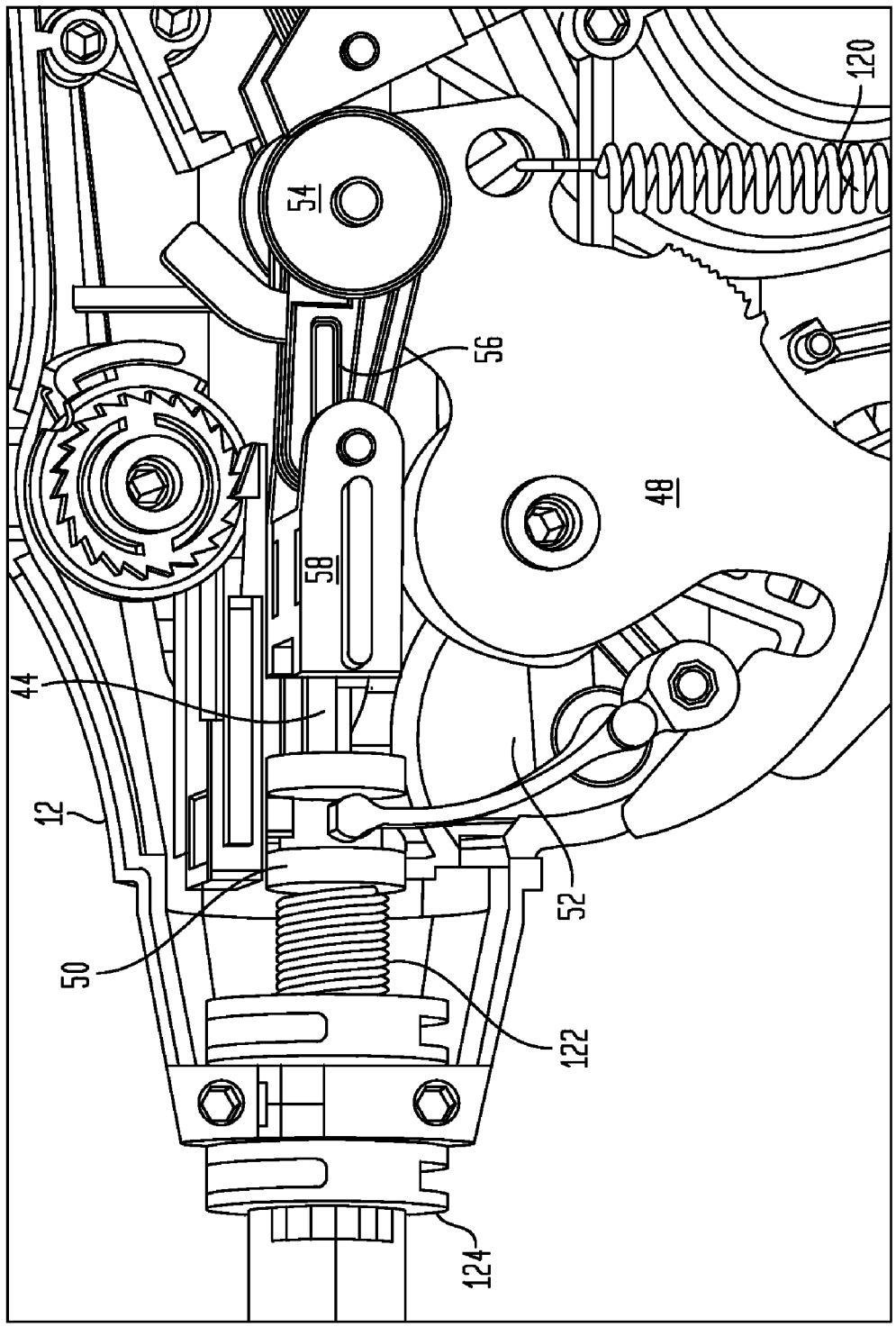
FIG. 17D is a side, partially cross-sectional view of a portion of the handle of the surgical clip applier shown in FIG. 17A, showing a clip forming assembly actuated.

As the trigger 16 is further actuated and the trigger insert 48 continues to pivot, the feed bar coupler 50 and feed bar 38 will eventually reach a distal-most position. In this position, the protrusion 86 on the feed bar 38 will be positioned at the distal end of the slot 88 in the jaw retainer shaft 28 and a clip will be positioned between the jaws 20, as previously discussed. Spring 122 will be fully compressed between the shaft coupler 124 and the feed bar coupler 50, and the feed link 52 will flex, as shown in FIGS. 17C and 17D. As the feed link 52 flexes, and more preferably once the feed link 52 fully flexed, the clip forming assembly will be actuated to close the jaws 20. The feed link 52 will remain flexed during actuation of the clip forming assembly, e.g., the second stage of actuation, such that the trigger insert 48 is pliant relative to the clip advancing assembly, and in particular the feed bar 38.

Figure 18:
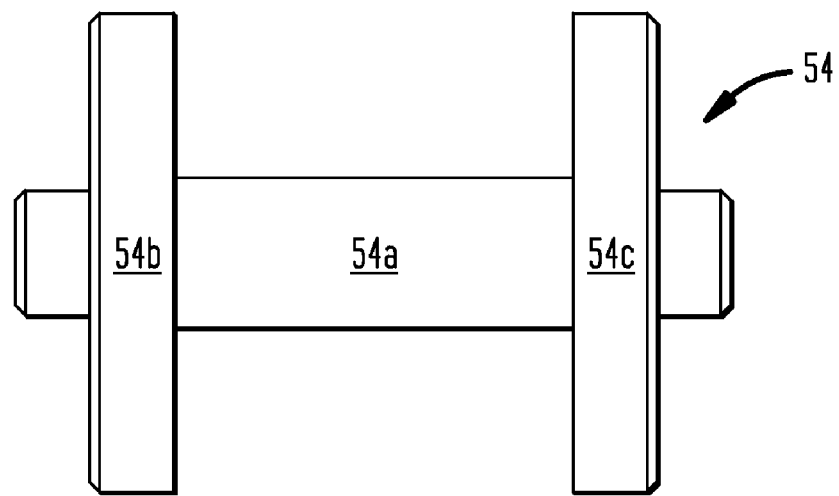
FIG. 18 is a side view of a closure link roller that forms part of a clip forming assembly of the surgical clip applier shown in FIG. 1A.
Figure 19:
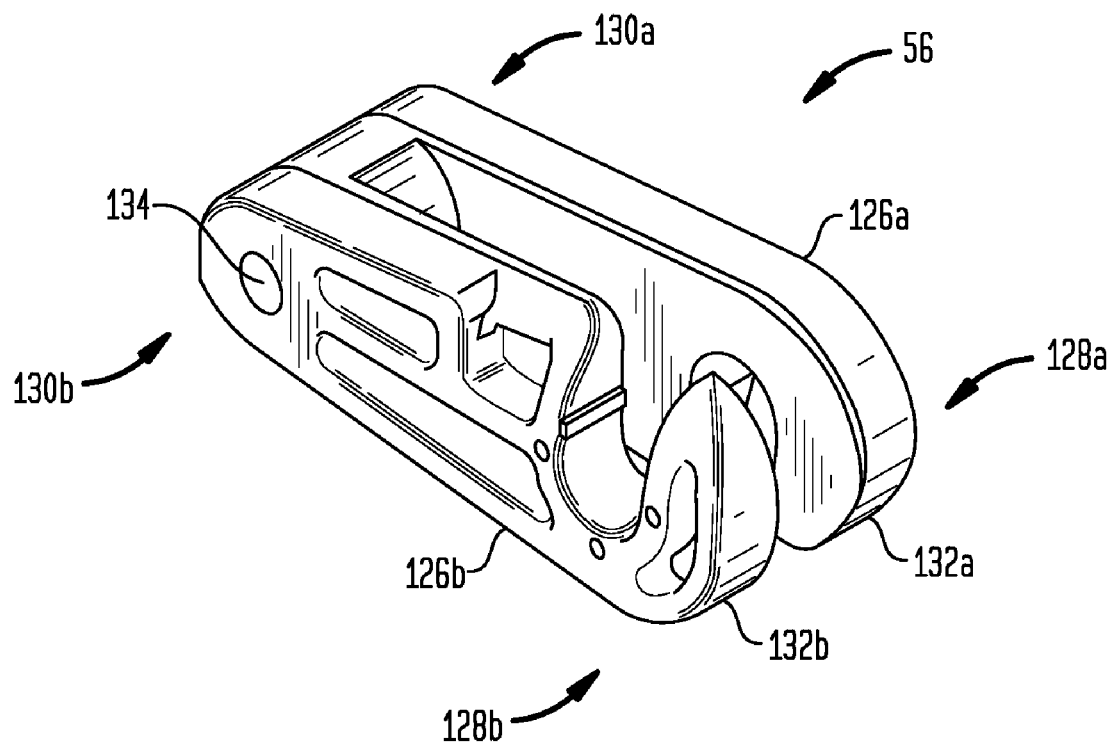
FIG. 19 is a top perspective view of a closure link that couples to the closure link roller shown in FIG. 18 to form part of a clip forming assembly of the surgical clip applier shown in FIG. 1A.

An exemplary clip forming assembly of the housing 12 is shown in more detail in FIGS. 18-20. In general, the clip forming assembly is disposed within the housing 12 and it is effective to move the push rod 44 and cam 42 relative to the jaws 20 to move the jaws 20 to a closed position and thereby crimp a clip positioned therebetween. While the clip forming assembly can have a variety of configurations, the illustrated exemplary clip forming assembly includes a closure link roller 54 that is slidably coupled to the trigger insert 48, a closure link 56 that is adapted to couple to the closure link roller 54, and a closure coupler 58 that is adapted to couple to the closure link 56 and to the push rod 44.

FIG. 18 illustrates the closure link roller 54 in more detail and, as shown, the closure link roller 54 includes a central shaft 54a having substantially circular flanges 54b, 54c formed adjacent to the opposed terminal ends thereof. The central shaft 54a can be adapted to sit within the second recess 110 in the trigger insert 48 such that the flanges 54b, 54c are received on opposed sides of the trigger insert 48. The central shaft 54a can also be adapted to mate to opposed arms 126a, 126b of the closure link 56 to position the arms on opposed sides of the trigger insert 48.

An exemplary embodiment of a closure link 56 is shown in more detail in FIG. 19, and as shown it has opposed arms 126a, 126b that are spaced a distance apart from one another. Each arm 126a, 126b includes a proximal end 128a, 128b that is adapted to engage the central shaft 54a of the closure link roller 54, and a distal end 130a, 130b that is adapted to mate to a closure coupler 58 for coupling the closure link roller 54 and closure link 56 to the push rod 44. In an exemplary embodiment, the proximal end 128a, 128b of each arm 126a, 126b is adapted to pivotally mate to the closure link roller 54, and thus the arms 126a, 126b can include, for example, hook-shaped members 132a, 132b formed thereon for engaging the central shaft 54a. The hook-shaped members 132a, 132b extend in opposite directions to facilitate engagement between the closure link 56 and the closure link roller 54. The distal end 130a, 130b of the arms 126a, 126b can be mated to one another, and they can include a lumen 134 extending therethrough for receiving a shaft that is adapted to pivotally mate the closure link 56 to the closure coupler 58. A person skilled in the art will appreciate that a variety of other techniques can be used to mate the closure link 56 to the closure link roller 54 and the closure coupler 58.

Figure 20A:
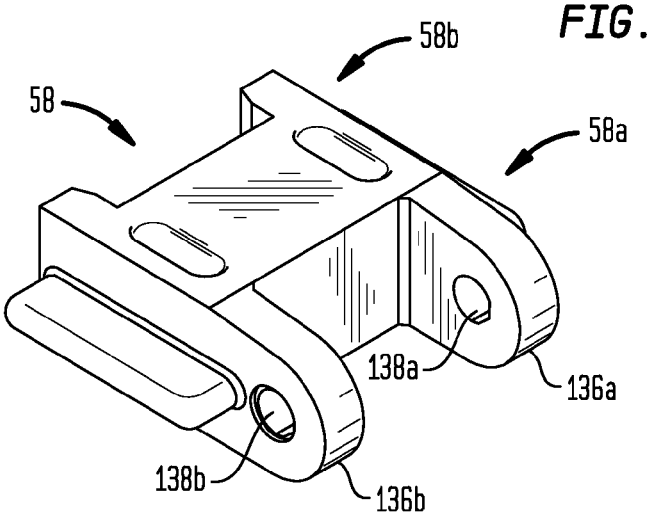
FIG. 20A is a top perspective view of a closure link coupler that couples to the closure link shown in FIG. 19 and that also forms part of the clip forming assembly of the surgical clip applier shown in FIG. 1A.
Figure 20B:
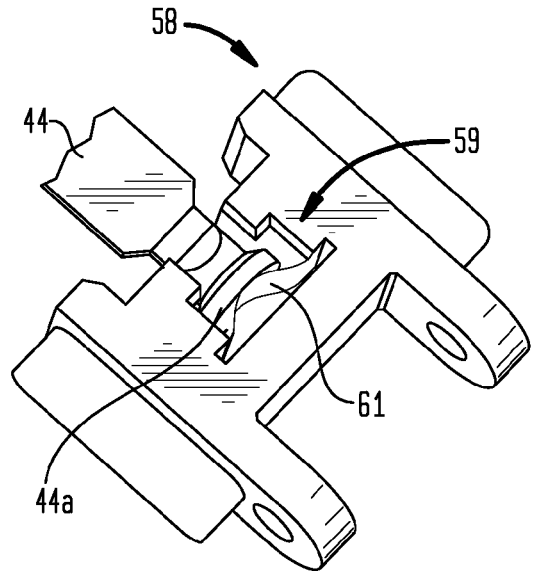
FIG. 20B is a bottom view of the closure link coupler shown in FIG. 20A coupled to the push rod of FIG. 9 and having one embodiment of a biasing element disposed therein.

An exemplary closure coupler 58 is shown in more detail in FIG. 20A, and as shown it includes a proximal portion 58a having two arms 136a, 136b with lumens 138a, 138b extending therethrough and adapted to be aligned with the lumen 134 in the closure link 56 for receiving a shaft to mate the two components. The closure coupler 58 can also include a distal portion 58b that is adapted to mate to the proximal end 44a of the push rod 44 (FIG. 9). In an exemplary embodiment, the closure coupler 58 includes a cut-out 59 (FIGS. 20B and 20C) formed therein and having a shape that is adapted to seat the proximal end 44a of the push rod 44. The distal portion 58b of the closure coupler 58 can also be configured to receive a portion of the feed bar coupler 50 when the trigger 16 is in the open position. A person skilled in the art will appreciate that a variety of other mating techniques can be used to mate the closure coupler 58 to the push rod 44, and that the closure coupler 58 and the push rod 44 can optionally be integrally formed with one another.

In other exemplary embodiments, a preloaded joint can be formed between the push rod 44 and the closure coupler 58 to prevent accidental release of a clip from the jaws, particularly during the early stages of closure, if the user eases-up on the trigger 16. In particular, while the anti-backup mechanism, discussed in more detail below, can be adapted to prevent the trigger 16 from opening until the trigger 16 reaches a predetermined position, the anti-backup mechanism may allow some minor movement of the trigger 16. Thus, in the event a user eases-up on the trigger 16 and minor opening of the trigger 16 occurs, the preloaded joint will bias the push rod 44 in a distal direction, thereby maintaining the push rod 44 in a substantially fixed position, while allowing the closure coupler 58 to move proximally until the trigger 16 is engaged by the anti-backup mechanism.

Figure 20C:
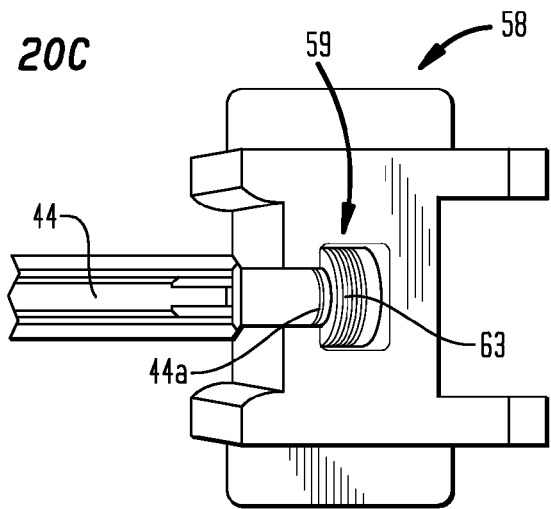
FIG. 20C is a bottom view of the closure link shown in FIG. 20A coupled to the push rod of FIG. 9 and having another embodiment of a biasing element disposed therein.

While the preloaded joint can have a variety of configurations, and it can be positioned at various locations along the clip forming assembly, in one exemplary embodiment the preloaded joint can be in the form of a biasing member disposed within the cut-out 59 to bias the push rod 44 in a distal direction. While a variety of biasing members can be used, in the embodiment shown in FIG. 20B, the biasing member is a cantilevered beam 61 that is positioned between the proximal end 44a of the push rod 44 and the back wall of the recess 59 to bias the push rod 44 distally. The cantilevered beam 61 can be formed from a shape memory material, such as Nitinol, that allows the beam 61 to flex or flatten when a proximally-directed force is applied thereto. The beam 61 can also be formed from a variety of other materials, such as spring steel or reinforced polymers, and more than one beam can be used. FIG. 20C illustrates another embodiment of a biasing member which is in the form of a coil or other type of spring 63. As shown, the spring 63 is disposed between the proximal end 44a of the push rod 44 and the back wall of the recess 59 to bias the push rod 44 distally. The spring 63 is adapted to compress when a proximally-directed force is applied thereto. A person skilled in the art will appreciate that a variety of other biasing members can be used, including elastomeric compression members.

Figure 20D:
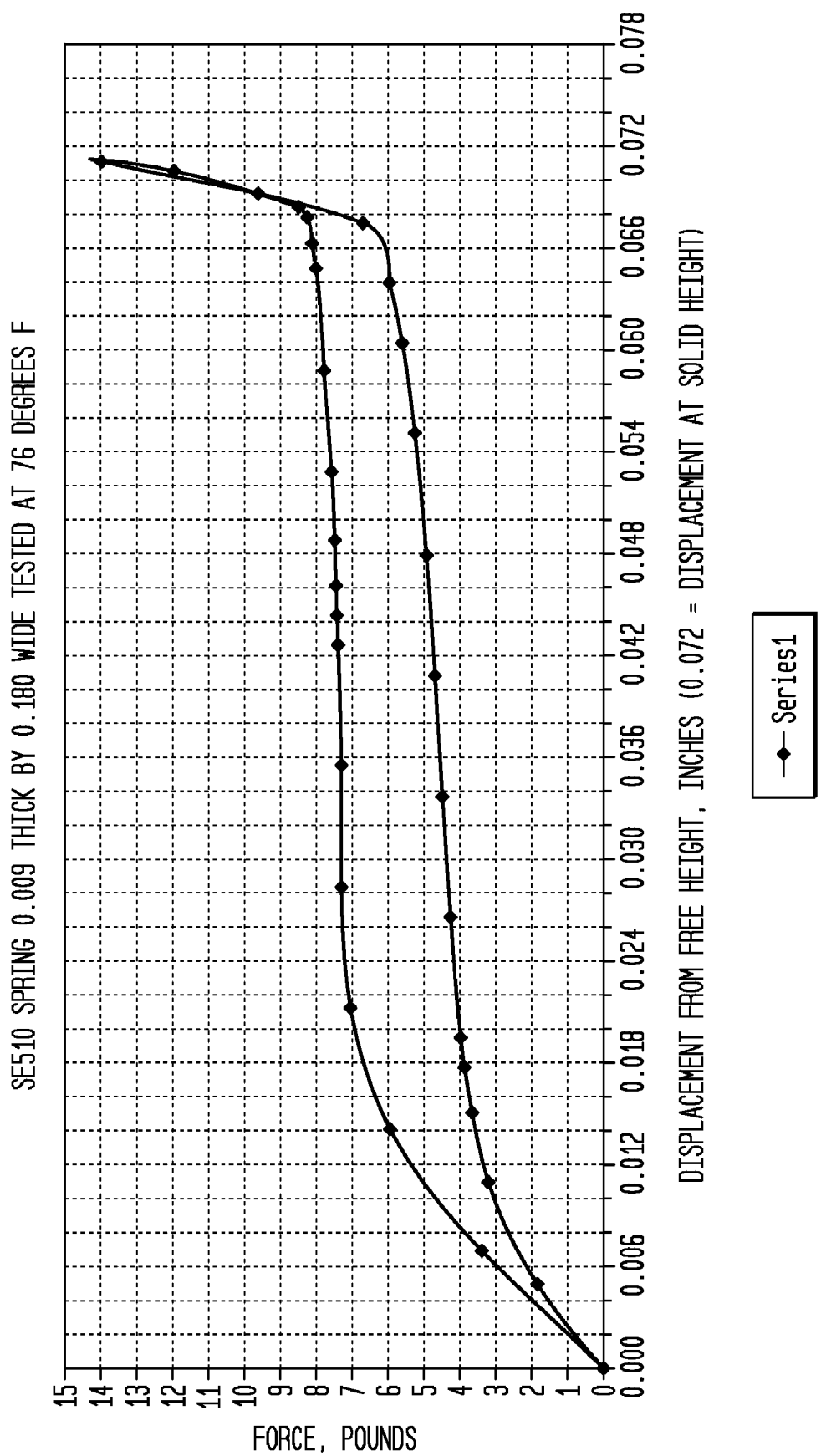
FIG. 20D is a chart showing the amount of force required to displace the biasing element shown in FIG. 20B.

The preloaded joint can also optionally include features to enhance performance of the cantilevered beam or spring during the clip forming process. In the embodiment shown in FIG. 20B, the load of the cantilevered beam 61 remains primarily uniform as the cantilevered beam is compressed during closure, however the load increases significantly during the final stages of closure. This is illustrated in FIG. 20D, which shows a graph of the load/displacement curve of the cantilevered beam 61 shown in FIG. 20B. The left end of the curve represents the unloaded height of the cantilevered beam 61, while the right end of the curve represents the point at which the cantilevered beam 61 is fully compressed or flattened. The upper curve represents the force resulting as the cantilevered beam 61 is compressed during a typical closing stroke, with the exception that the force is measured from a free state of the cantilevered beam 61 whereas the cantilevered beam 61 is initially partially compressed when it is disposed within the closure coupler 58. As shown, the load remains substantially constant (excluding the initial compression stages), increasing only slightly during the closing stroke as the cantilevered beam 61 is being compressed. However, the load increases significantly at the final stages of closure when the cantilevered beam 61 is fully flattened. This is due to deflection of the cantilevered beam 61 which causes the load to be transferred from the terminal ends of the cantilevered beam 61 inward. As the cantilevered beam 61 deflects and the load is transferred inward, the effective length of the cantilevered beam 61 is decreased, thereby increasing the load. In order to prevent this, the preloaded joint can optionally include features to enhance the cantilevered beam or spring performance, and in particular to maintain a substantially constant load during clip formation.

Figure 20E:
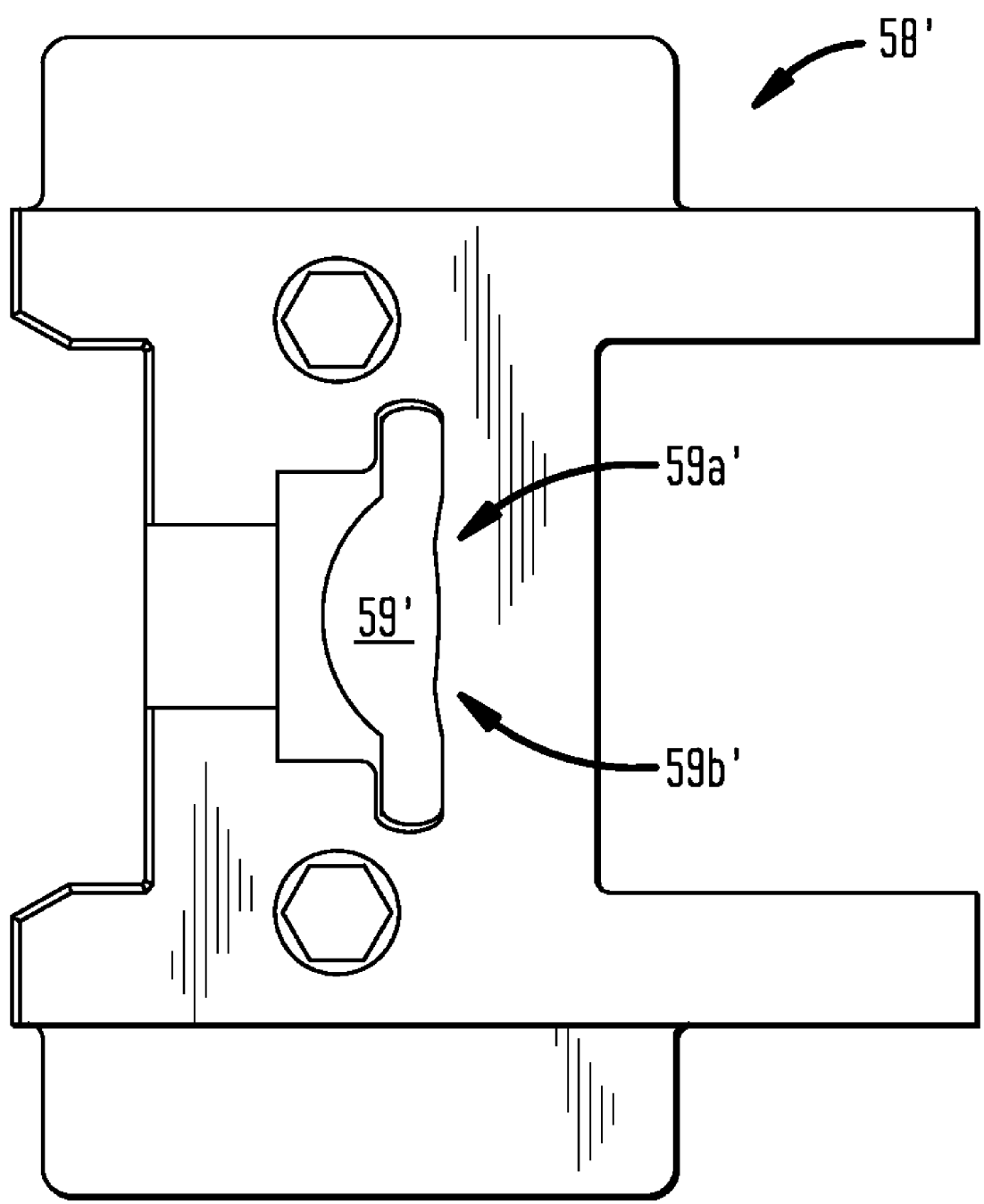
FIG. 20E is a side view of another embodiment of a portion of a closure link coupler having ridges formed therein.

FIG. 20E illustrates one exemplary embodiment of a technique for enhancing the cantilevered beam or spring performance. As shown, the recess 59' in the closure coupler 58' includes two ridges 59a', 59b' formed therein on the back surface thereof such that the ridges 59a', 59b' are positioned underneath or behind the cantilevered beam (not shown). The ridges 59a', 59b' are spaced a distance apart from one another and each ridge 59a', 59b' has a height of at least about 0.005" to prevent the cantilevered beam from fully flattening against the back surface of the recess. As a result, the ridges 59a', 59b' will prevent the cantilevered beam from deflecting, thereby preventing the load of the spring or cantilevered beam from transferring from the terminal ends inward. A person skilled in the art will appreciate that the particular location, quantity, and size of the ridges 59a', 59b' can vary depending on the configuration of the preloaded joint, as well as the forces necessary to prevent clip fallout during closure.

In use, referring back to FIGS. 17A-17D, as the trigger 16 is initially moved from the open position toward the closed position, the closure link roller 54 will roll within the recess 110 in the trigger insert 48. Once the feed bar 38 and feed bar coupler 50 are in the distal-most position, as shown in FIG. 17C, further actuation of the trigger 16 will cause the recess 110 in the trigger insert 48 to engage the closure link roller 54 forcing it to pivot with the trigger insert 48, as shown in FIG. 17D. As a result, the closure coupler 58 will move distally, thereby causing the push rod 44 to move distally. As the push rod 44 advances distally, the cam 42 is advanced over the jaws 20 to close the jaws 20 and crimp the clip positioned therebetween. The trigger 16 can optionally be partially closed to only partially close the jaws 20 and thus partially crimp a clip disposed therebetween. Exemplary techniques for facilitating selective full and partial closure of the clip will be discussed in more detail below. Once the clip is applied, the trigger 16 can be released thereby allowing spring 120 to pull the trigger insert 48 back to its initial position, and allowing spring 122 to force the feed bar coupler 50 and feed bar 38 back to the proximal position. As the trigger insert 48 returns to its initial position, the closure link roller 54 is moved back to its initial position as well, thereby pulling the closure link 56, closure coupler 58, and push bar 44 proximally.

The surgical clip applier 10 can also include a variety of other features to facilitate use of the device 10. In one exemplary embodiment, the surgical clip applier 10 can include an anti-backup mechanism for controlling movement of the trigger 16. In particular, the anti-backup mechanism can prevent the trigger 16 from opening during a partial closing stroke. However, once the trigger reaches a predetermined position, at which point the clip positioned between the jaws can be partially crimped, the anti-backup mechanism can release the trigger allowing the trigger to open and release the clip or to close to fully crimp the clip, as may be desired by the user.

Figure 21A:
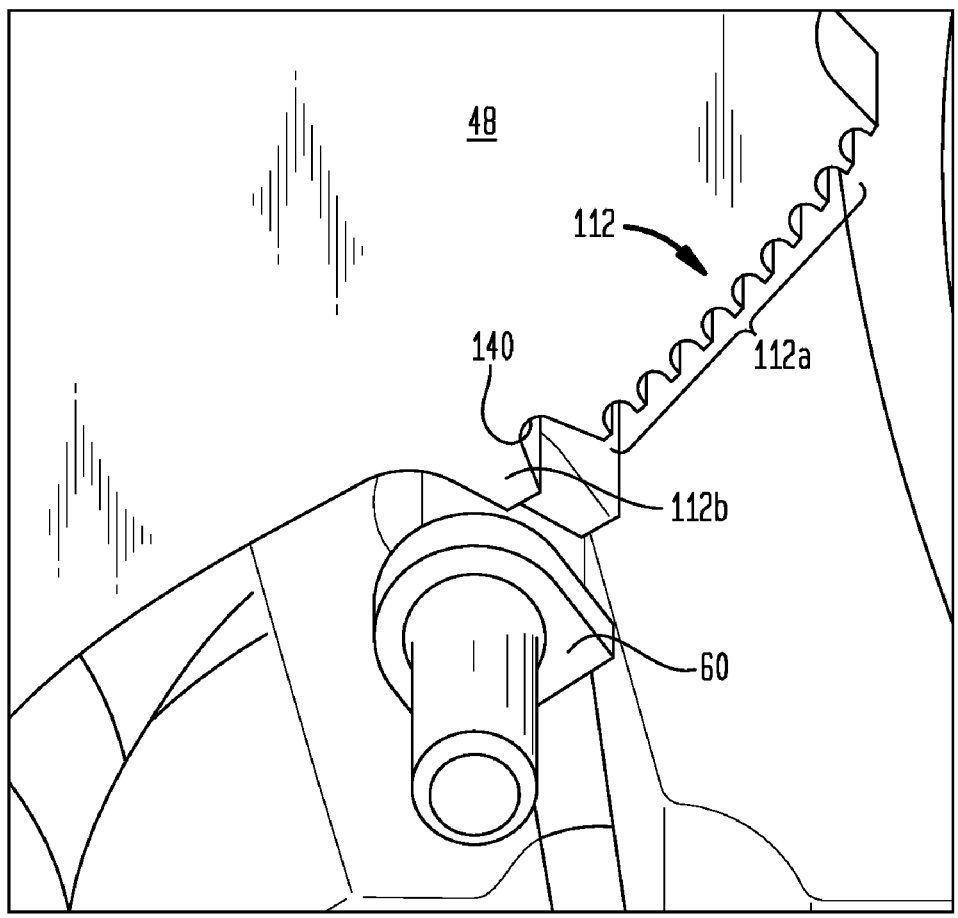
FIG. 21A is an enlarged side perspective view of an anti-backup mechanism of the surgical clip applier shown in FIG. 1A.
Figure 21B:
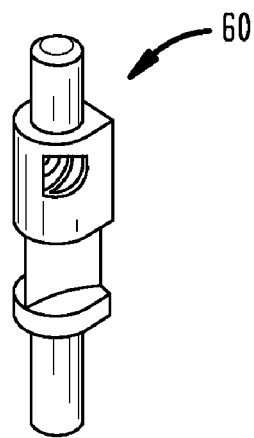
FIG. 21B is a perspective view of a pawl mechanism of the anti-backup mechanism shown in FIG. 21A.

FIGS. 21A and 21B illustrate one exemplary embodiment of an anti-backup mechanism in the form of a ratchet. As shown, the ratchet includes a set of teeth 112 formed on the trigger insert 48, and a pawl 60 that is adapted to be rotatably disposed within the housing 12 and positioned adjacent to the trigger insert 48 such that closure of the trigger 16 and pivotal movement of the trigger insert 48 will cause the pawl 60 to engage the teeth 112. The teeth 112 can be configured to prevent rotation of the pawl 60 until the pawl 60 reaches a predetermined position, at which point the pawl 60 is free to rotate, thereby allowing the trigger 16 to open or close. The predetermined position preferably corresponds to a position at which the jaws 20 are partially closed. In an exemplary embodiment, as shown, the teeth 112 include a first set of teeth 112a, e.g., ten teeth, having a size that prevents rotation of the pawl 60 relative thereto, thus preventing the trigger 16 from opening when the pawl 60 is engaged with the first set 112a of teeth 112. The teeth 112 can also include a final or terminal tooth, referred to as a tock tooth 112b, that has a size that allows the pawl 60 to rotate relative thereto when the pawl 60 is engaged with the tock tooth 112b. In particular, the tock tooth 112b preferably has a size that is substantially greater than the size of the first set of teeth 112a such that a relatively large notch 140 is formed between the first set of teeth 112a and the tock tooth 112b. The notch 140 has a size that allows the pawl 60 to pivot therein, thus allowing the pawl 60 to be selectively moved beyond the tock tooth 112b or back toward the first set of teeth 112a. A person skilled in the art will appreciate that the tock tooth 112b can have the same size or a smaller size than the first ten teeth 112a while still providing a notch 140 formed therebetween that allows the pawl 60 to pivot therein.

Figure 22B:
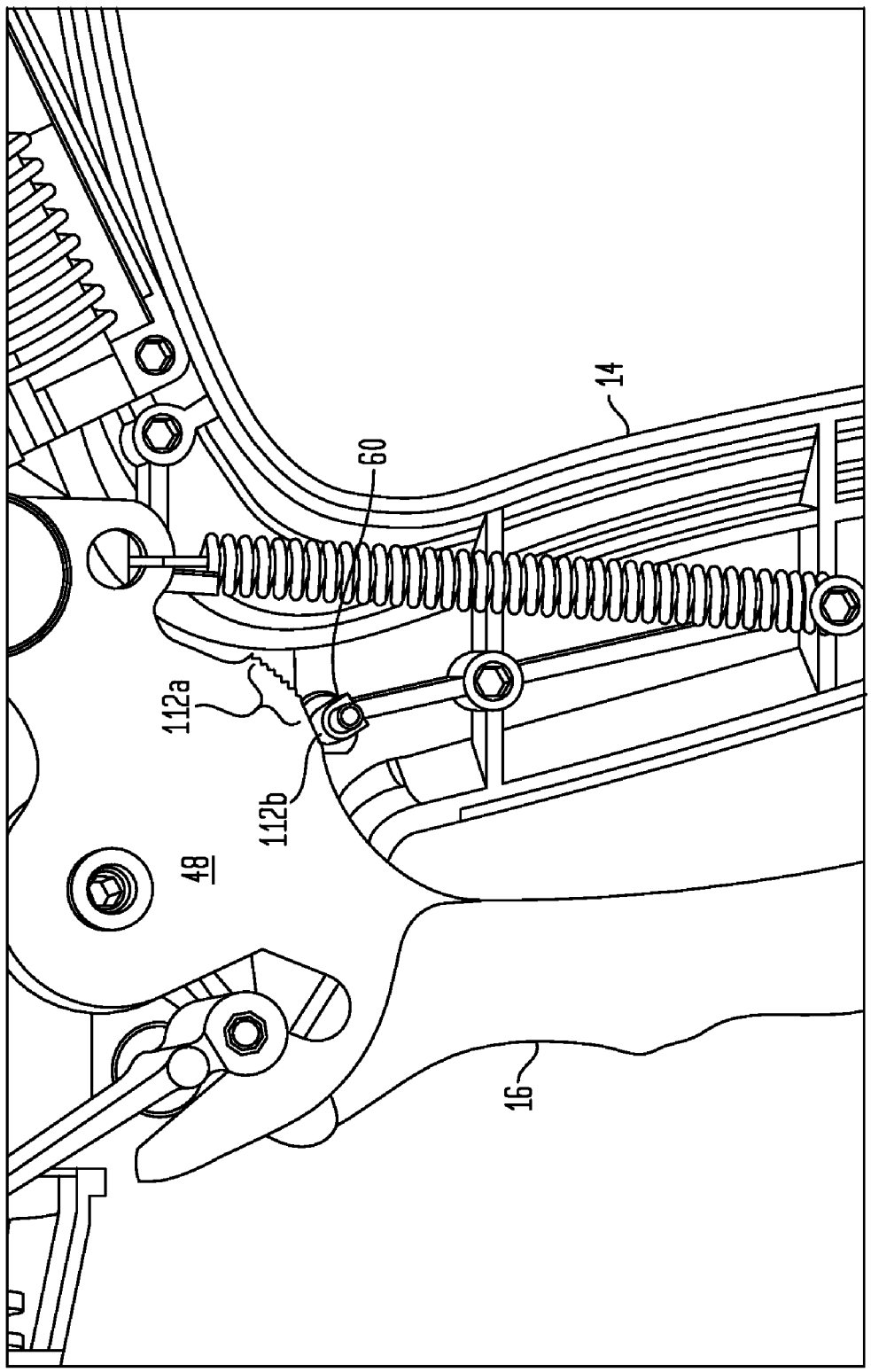
FIG. 22B is a side, partially cross-sectional view of a portion of the handle of the surgical clip applier shown in FIG. 22A, showing the anti-backup mechanism in a partially actuated position.
Figure 22D:
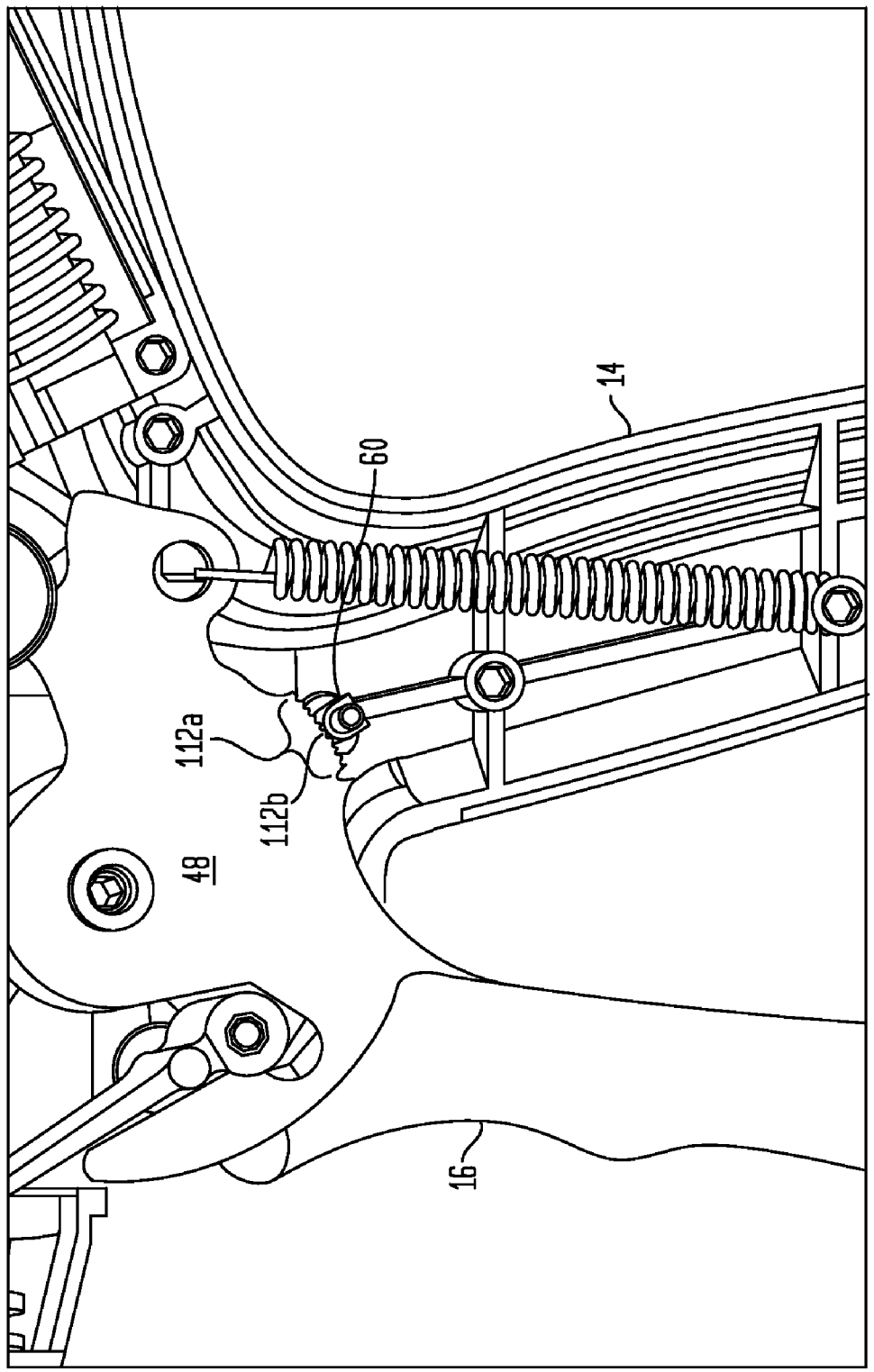
FIG. 22D is a side, partially cross-sectional view of a portion of the handle of the surgical clip applier shown in FIG. 22C, showing the anti-backup mechanism returning to an initial position.
Figure 22E:
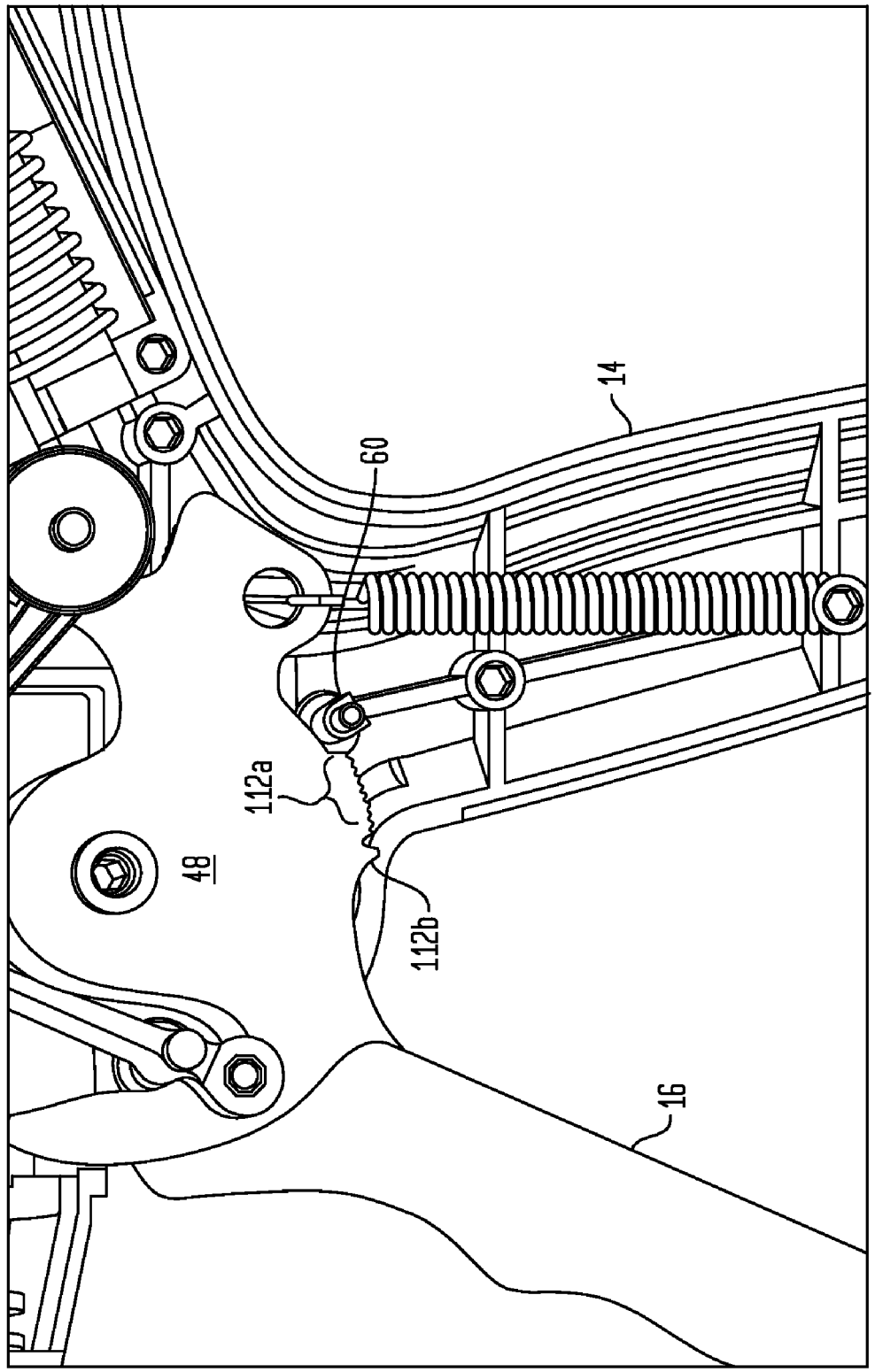
FIG. 22E is a side, partially cross-sectional view of a portion of the handle of the surgical clip applier shown in FIG. 22D, showing the anti-backup mechanism returned to the initial position.

FIGS. 22A-22D illustrates the ratchet mechanism in use. When the trigger 16 is initially moved toward a closed position, as shown in FIG. 22A, the pawl 60 will engage the first set of teeth 112a thereby preventing the trigger 16 from opening. Further actuation of the trigger 16 will cause the pawl 60 to advance past the first set of teeth 112a until the pawl 60 reaches the notch 140 next to the tock tooth 112b. Once the pawl 60 reaches the tock tooth 112b, at which point the jaws 20 are partially closed due the partial distal movement of the cam 42 over the jaws 20, the pawl 60 is free to rotate thereby allowing the trigger 16 to open or close, as may be desired by the user. FIG. 22C illustrates the trigger 16 in a fully-closed position, and FIGS. 22D and 22E illustrate the trigger 16 returning to the open position.

The ratchet mechanism can also be configured to emit an audible sound that indicates the position of the jaws 20. For example, a first sound can be emitted when the pawl 60 engages the first set of teeth 112a, and a second, different sound, e.g., a louder sound, can be emitted when the pawl 60 engages the tock tooth 112b. As a result, when the trigger 16 reaches the predetermined position at which the pawl 60 is engaged with the tock tooth 112b, the sound indicates to the user that the jaws 20 are in the partially closed position. The user can thus release the trigger 16 to release a partially closed clip, or they can fully close the trigger 16 to fully close the clip.

In another exemplary embodiment, the surgical clip applier 10 can include an overload mechanism that is adapted to prevent overload of a force applied to the jaws 20 by the trigger 16. Typically, during application of a surgical clip, a certain force is required to close the jaws 20 and crimp the clip around the tissue positioned therebetween. As the forming process proceeds and the clip is at least partially closed, the force required to continue closing the jaws 20 around the clip significantly increases. Accordingly, in an exemplary embodiment, the overload mechanism can have a resistance that correlates to the force required to close the jaws 20. In other words, the resistance of the overload mechanism can increase as the force required to close the jaws 20 increases. The resistance is, however, preferably slightly greater than the force required to close the jaws 20 to prevent accidental actuation of the overload mechanism. As a result, if the jaws 20 are prevented from closing when the trigger 16 is initially actuated, the force required to overcome the resistance of the overload mechanism is relatively low. This is particularly advantageous as the jaws 20 are more susceptible to being deformed when they are open or only partially closed. The overload mechanism will actuate more readily in the early stages of clip formation to prevent deformation of the jaws. Conversely, when the jaws 20 are substantially closed, the resistance is relatively high such that the overload mechanism can only be actuated upon application of a significant force applied to the jaws 20.

Figure 23A:
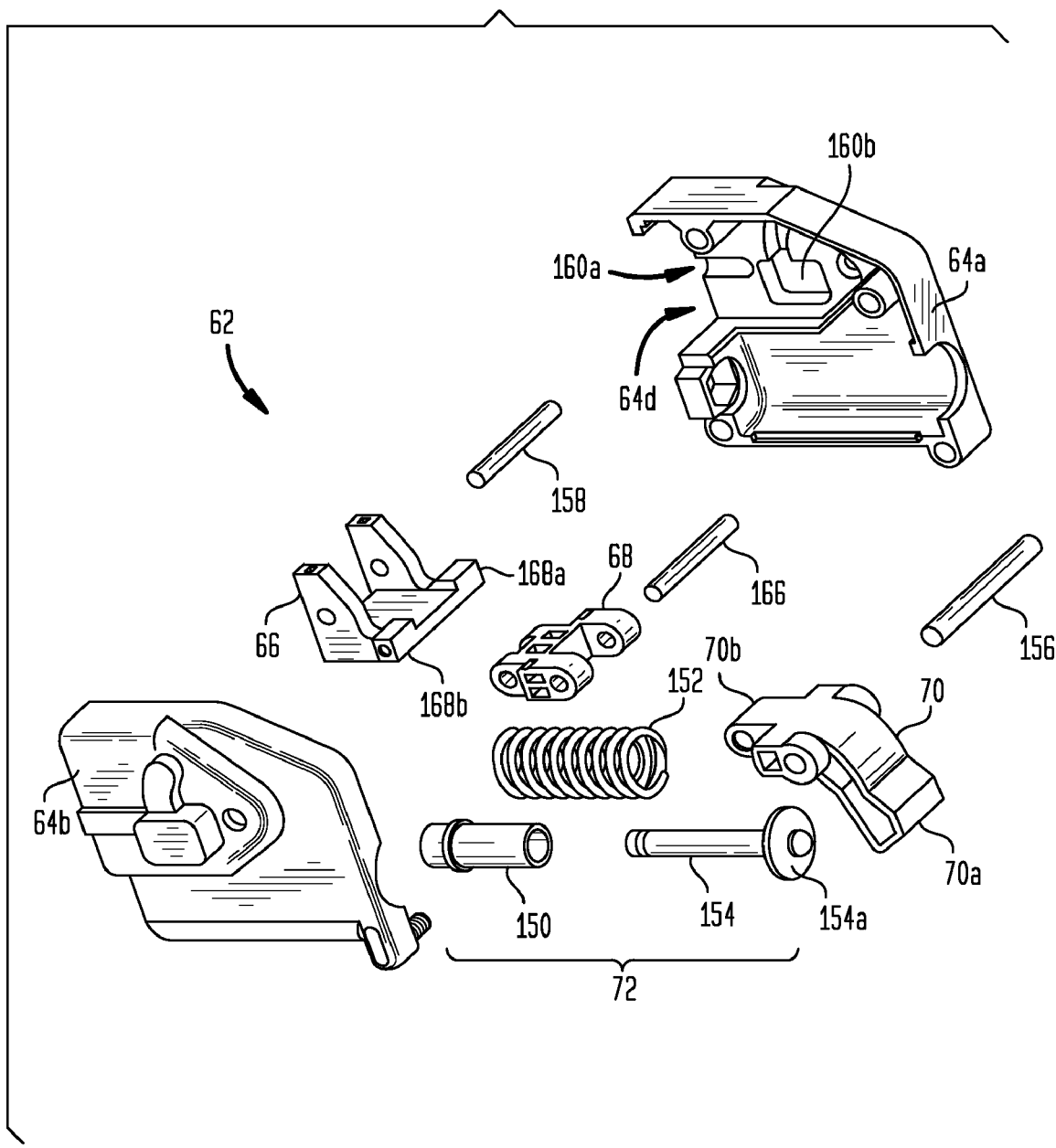
FIG. 23A is an exploded view of an overload mechanism of the surgical clip applier shown in FIG. 1A.

FIG. 23A illustrates one exemplary embodiment of an overload mechanism 62, showing an exploded view. In general, the overload mechanism can include an overload housing 64 formed from two halves 64a, 64b and containing a profile link 66, a toggle link 68, a pivot link 70, and a biasing assembly 72. The biasing assembly 72 can include a spring post 150 that is coupled to the housing 64 and that includes a bore extending therethrough for receiving a plunger 154. A spring 152 is disposed around the spring post 150, and the plunger 154 extends through the spring post 150 and includes a head 154a formed thereon that is adapted to abut against the spring 152. The pivot link 70 can be generally L-shaped and it can be coupled to the housing 64 by a pivot pin 156 extending therethrough. A proximal end 70a of the pivot link 70 can contact the head 154a of the plunger 154, and a distal end 70b of the pivot link 70 can be pivotally coupled to the toggle link 68 by a pivot pin 166. The toggle link 68, in turn, can be coupled to the profile link 66, which can be slidably and pivotally positioned within the housing 64 adjacent to an opening 64d formed in the housing. Pivotal movement of the profile link 66 within the housing 64 can be achieved by, for example, a pivot pin 158 that extends through the profile link 66 and is that disposed within a first slot 160a (only one slot is shown) formed in each half 64a, 64b of the housing 64, and slidable movement of the profile link 66 within the housing 64 can be achieved by, for example, opposed protrusions 168a, 168b formed on the profile link 66 that are received within a second slot 160b (only one slot is shown) formed in each half 64a, 64b of the housing 64.

In use, the profile link 66 can be adapted to receive a force from the clip forming assembly and to counter the force with the resistance of the biasing assembly 72. In particular, the overload mechanism 62 uses the spring 152 along with the toggle link 68 and pivot link 70 to bias the profile link 66 from either rotating about the pivot pin 158 or sliding against the housing 64. For the rotational aspect, the force exerted by the compressed spring 152 is transferred through the toggle link 68 and pivot link 70, such that a rotational moment is applied to the profile link 66 against the housing 64. Thus this assembly causes the profile link 66 to resist rotation with respect to the housing 64. If the moment generated by a radial load from the closure link roller 54 against the profile link 66 exceeds the moment of the pivot link 70 and toggle link 68, the profile link 66 begins to rotate, buckling the toggle link 68 and causing the pivot link 70 to further compress the spring 152. For the sliding aspect, the pivot link 70, toggle link 68, and profile link 66 are aligned such that the sliding force (resistance to slide) is the force required to buckle the toggle link 68 and pivot link 70. If the radial load from the closure link roller 54 against the profile link 66 exceeds the buckling force of the linkages, then the pivot link 70 further compresses the spring 152 as the profile link 66 slides proximally.

Figure 23B:
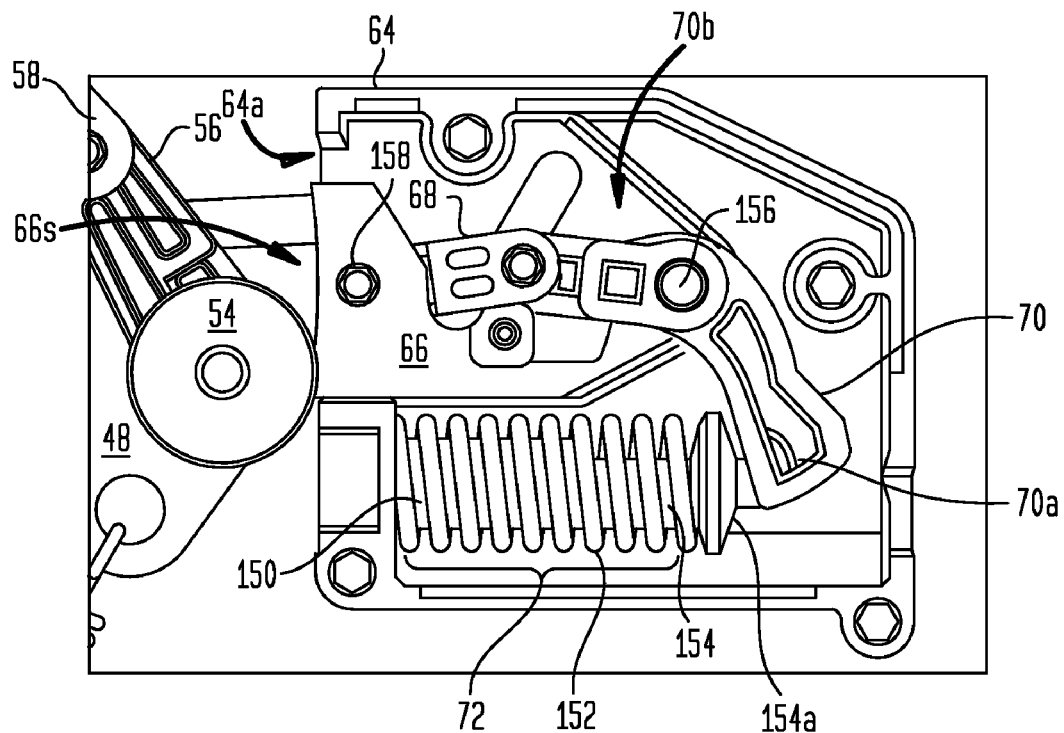
FIG. 23B is a partially cross-sectional view of the overload mechanism shown in FIG. 23A, showing the closure link roller first coming into contact with the profile link.
Figure 23C:
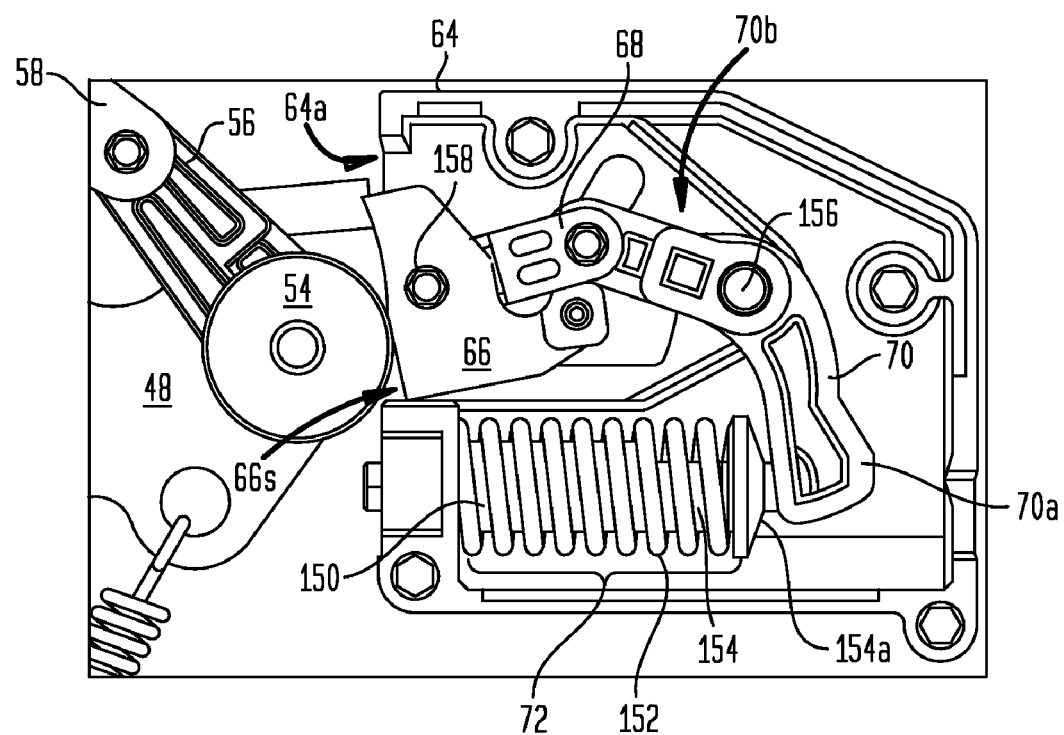
FIG. 23C is a partially cross-sectional view of the overload mechanism shown in FIG. 23B, showing the closure link roller applying a force to the profile link causing the profile link to pivot.

This is shown in more detail in FIGS. 23B-23C, and as shown the opening 64d in the housing 64 allows the closure link roller 54 of the clip forming assembly to roll against the profile link 66. As a result, when the trigger 16 is actuated and moved toward the closed position, the closure link roller 54 applies a force to the profile link 66. The resistance of the overload spring 152 will, however, maintain the profile link 66 in a substantially fixed position unless the force applied by the closure link roller 54 increases to a force that is greater than the resistance, e.g., a threshold force. This can be caused by, for example, a foreign object positioned between the jaws 20 or when the jaws 20 are fully closed with the clip and vessel, duct, shunt, etc. therebetween. When the jaws 20 cannot be further closed, the force applied to the closure link roller 54 from the closing motion of the trigger 16 will be transferred to the profile link 66, which will then pivot and slide within the housing 64, thereby causing the pivot link 70 to pivot, which forces the plunger 154 to compress the overload spring 152.

As previously noted, the force required to actuate the overload mechanism can correlate to the force required to close the jaws 20, which increases as the trigger 16 is moved to the closed position. This can be achieved due to the configuration of the profile link 66. In particular, when the closure link roller 54 first comes into contact with the profile link 66 and is thus in a lower position, the profile link 66 can pivot within the housing 64, as shown in FIG. 23B. As the closure link roller 54 moves upward along the profile link 66, the force required to overcome the resistance of the overload mechanism increases because the profile link 66 must slide within the housing 64, as shown in FIG. 23C. The force required to pivot the profile link 66 can be less than the force required to slide the profile link 66. Accordingly, if the jaws 20 are prevented from being closed, e.g., by a foreign object, as the trigger is initially actuated, a minimal force will be required to cause the closure link roller 54 to transfer the force to the lower portion of the profile link 66 causing the profile link 66 to pivot. When the jaws 20 are substantially closed and the trigger 16 is almost fully actuated, a significant amount of force is required to cause the closure link roller 54 to transfer the force to the upper portion of the profile link 66 causing the profile link 66 to slide within the housing 64 to overcome the resistance of the overload spring 152. While the amount of force required to actuate the overload mechanism can be greater than and can increase relative to the amount of force required to close the jaws 20, the force is preferably only slightly greater than the force required to close the jaws 20 to prevent deformation or other damage to the jaws 20. A person skilled in the art will appreciate that the resistance can be adjusted based on the force necessary to close the jaws 20.

The profile link 66, and in particular the distal-facing surface 66s of the profile link 66, can also have a shape that facilitates correlation between the force required to actuate the overload mechanism and the force required to close the jaws 20. For example, where the force required to close the jaws 20 increases at a linear rate, the distal-facing surface 66s of the profile link 66 can be planar to prevent the profile link 66 from interfering with movement of the closure link roller 54 there over, and to allow a linear force to be applied to the trigger 16 to close the jaws 20. Conversely, where the force required to close the jaws 20 is non-linear as the trigger 16 is moved to the closed position, the profile link 66 can have a non-linear shape that corresponds to the non-linear force. Such a configuration will prevent the forces required to close the cam 42 (FIG. 8) from becoming too high.

By way of non-limiting example, the force required to close the jaws 20 can be non-linear due to the shape of the recess 104 in the cam 42 that is adapted to push the jaw members 96a, 96b toward one another. As shown in FIG. 8, the recess 104 can have a curved configuration such that the force will vary as the cam 42 passes over the jaw members 96a, 96b. The profile link 66 can therefore having a corresponding curved distal-facing surface such that the force will also vary as the closure link roller 54 passes there over. As shown in FIGS. 23A and 23B, the profile link 66 is curved such that the lower portion of the profile link 66 is substantially convex and the upper portion of the profile link 66 is substantially concave. A person skilled in the art will appreciate that the profile link 66 can have a variety of other shapes, and that a variety of other techniques can be used to optimize the force necessary to close the jaws 20 and the force necessary to actuate the overload mechanism.

Figure 23D:
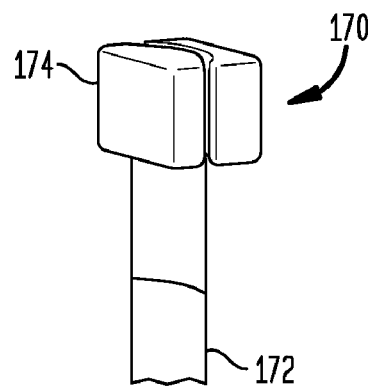
FIG. 23D is a perspective view of another embodiment of an overload mechanism for use with a surgical clip applier.

A person skilled in the art will also appreciate that the overload mechanism can have a variety of other configurations. By way of non-limiting example, FIG. 23D illustrates an overload mechanism that is in the form of a cantilevered beam 170 for receiving a force applied by the closure link roller 54. The beam 170 can have a substantially curved member 172 with a bracket 174 coupled to one end thereof. The curved member 172 can have a bending moment that, when loaded with a force greater then the bending moment, buckles to assume a low rigidity condition. The bracket 174 can provide more rigidity to the curved member 172 such that the bending moment increases adjacent to the bracket 174. In use, the beam 170 can be loaded within the housing 12 of the clip applier 10 such that the closure link roller 54 contacts the concave surface, and the beam 170 can be positioned at an angle such that the closure link roller 54 is farther away from the beam when the trigger 16 is initially actuated, and the closure link roller 54 becomes closer to the beam as the trigger 16 moves to the closed position. As a result, the resistance to buckling will increase as the closure link roller 54 moves thereof and the trigger 16 of the clip applier is moved to the closed position. Although not shown, multiple beams could optionally be used in a stacked fashion and the terminal or free end of the beam(s) could be contoured to tailor the buckling load at a particular point along the length of the beam.

In another exemplary embodiment, the surgical clip applier 10 can include a clip quantity indicator for indicating the number of clips remaining in the device 10. While various techniques can be used to indicate the quantity of clips remaining, FIGS. 24A-25 illustrate one exemplary embodiment of a clip quantity indicator having an indicator wheel 74 and an indicator actuator 76.

Figure 24A:
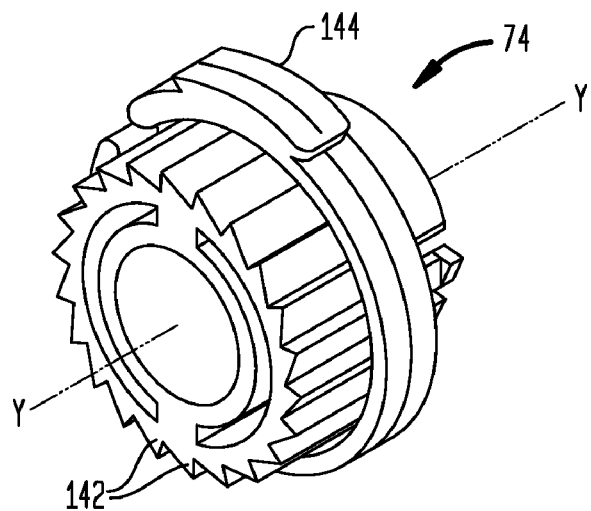
FIG. 24A is a side perspective view of a clip quantity indicator wheel of the surgical clip applier shown in FIG. 1A.
Figure 24B:
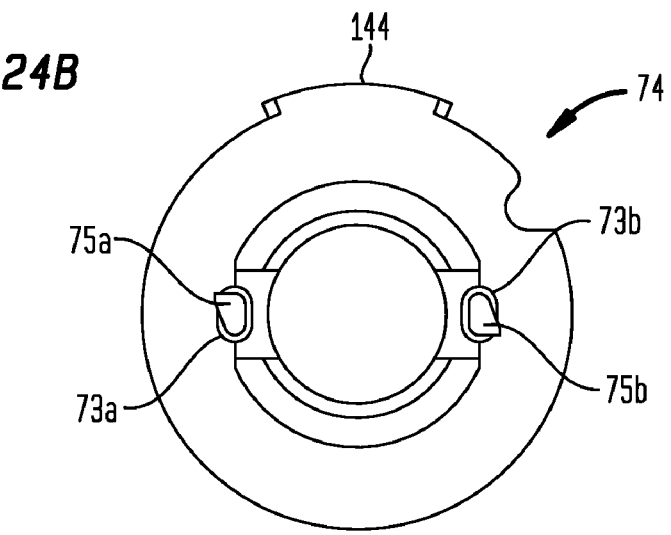
FIG. 24B is a side view of a clip quantity indicator wheel shown in FIG. 24A.

The indicator wheel 74 is shown in detail in FIGS. 24A and 24B, and as shown it has a generally circular or cylindrical shape that defines a central axis Y about which the wheel 74 is adapted to rotate. The wheel 74 includes teeth 142 formed therearound and adapted to be engaged by the indicator actuator 76, and an indicator member 144. The indicator member 144 can have a variety of configurations, but in an exemplary embodiment the indicator member 144 is in the form of a contrasting color pad having a color, e.g., orange, red, etc., that differs from the remainder of the indicator wheel 74.

Figure 25:
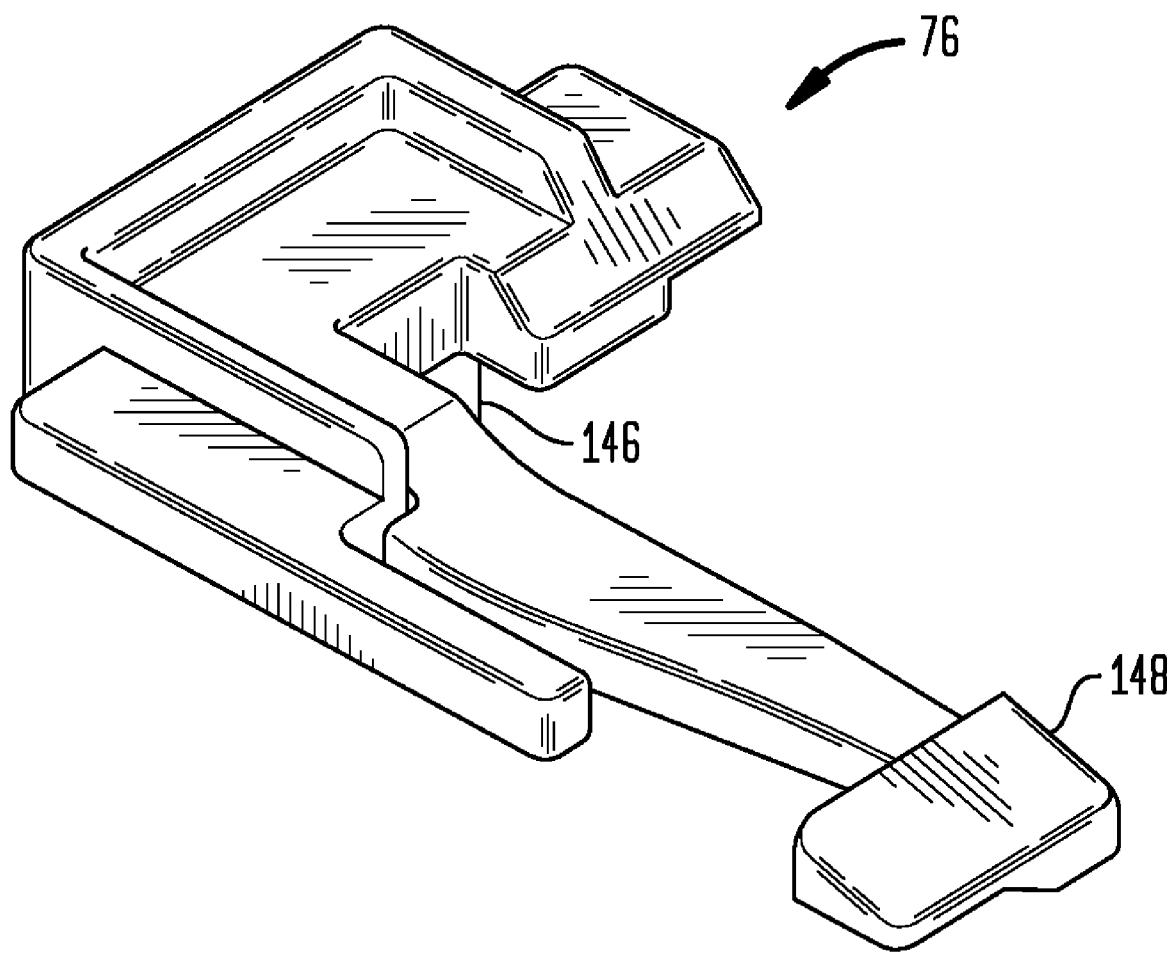
FIG. 25 is a top perspective view of a clip quantity actuator for use with the clip quantity indicator wheel shown in FIG. 24.

FIG. 25 illustrates the exemplary indicator actuator 76 in more detail. The actuator 76 is adapted to be slidably disposed within the housing 12 and to couple to the feed link coupler 50 and move as the feed bar coupler 50 and feed bar 38 are moved. Accordingly, the indicator actuator 76 can include a protrusion 146, only a portion of which is shown, formed on an inferior surface thereof for extending into the recess 50f formed between the circular flanges 50d, 50e on the feed bar coupler 50. The protrusion 146 allows the indicator actuator 76 to be engaged by the feed bar coupler 50 and moved therewith. The indicator actuator 76 can also include an engagement mechanism 148 formed thereon and adapted to engage the teeth 142 formed on the indicator wheel 74. As shown in FIG. 25, the engagement mechanism 148 on the indicator actuator 76 is in the form of an arm having a tab formed on the end thereof for engaging the teeth 142.

Figure 26A:
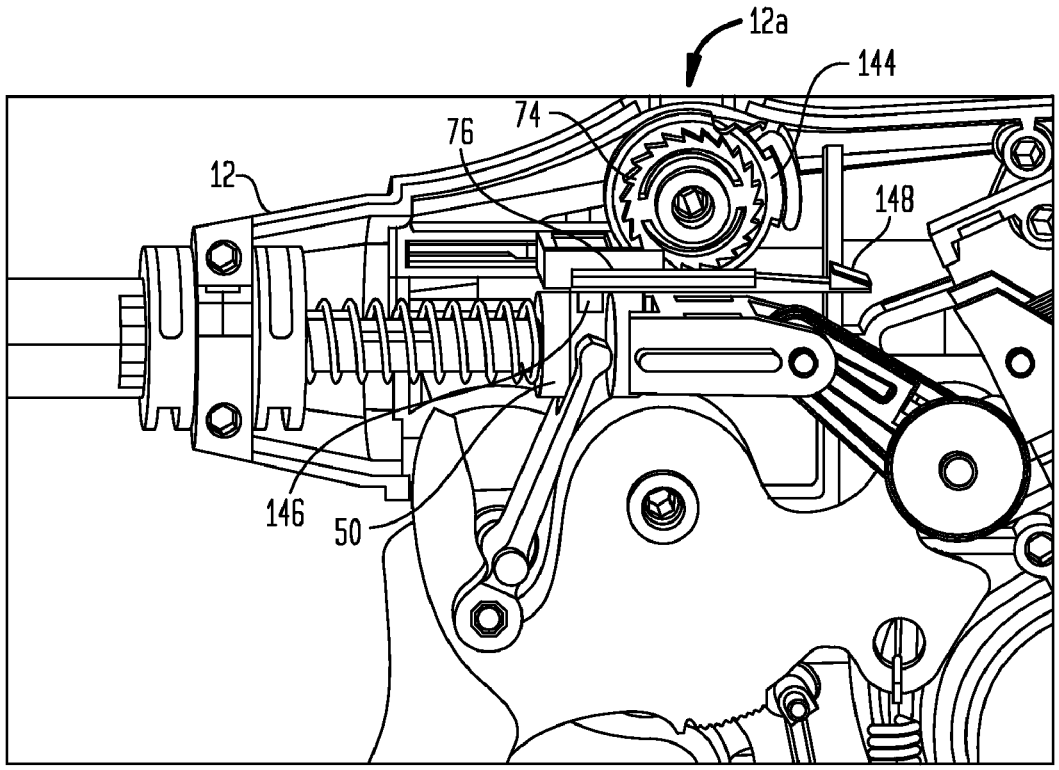
FIG. 26A is a side, partially cross-sectional view of a portion of the handle of the surgical clip applier shown in FIG. 1A, showing movement of the clip quantity actuator of FIG. 25 and the clip quantity indicator wheel of FIG. 24.
Figure 26B:
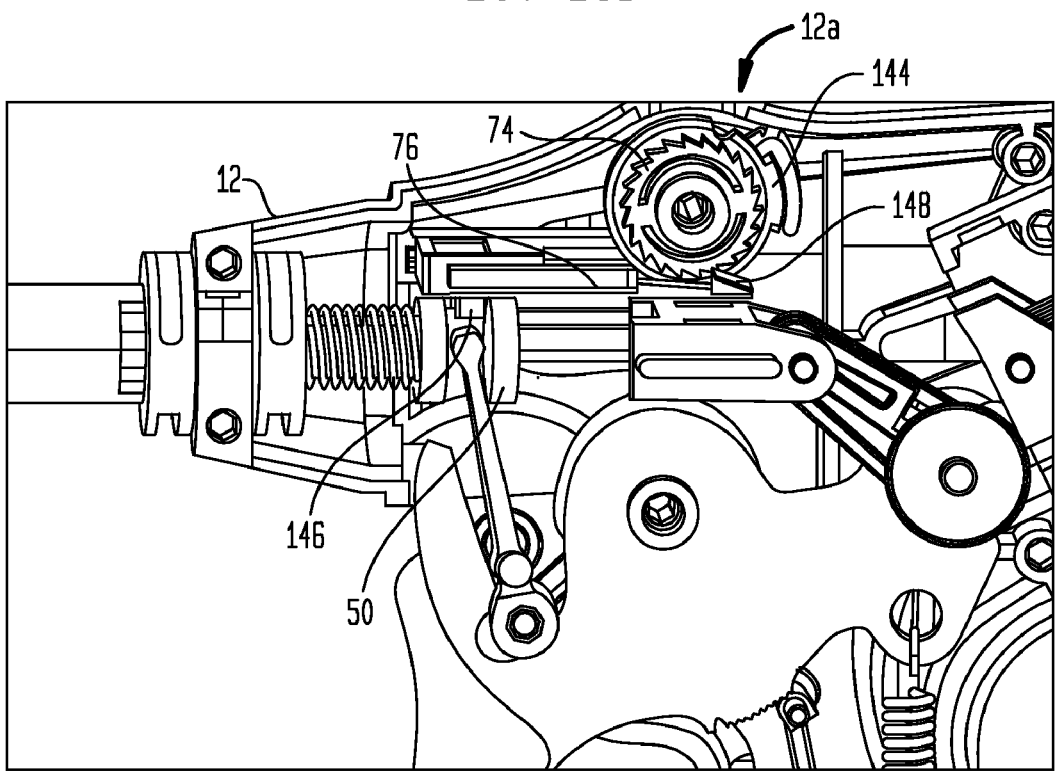
FIG. 26B is a side, partially cross-sectional view of a portion of the handle of the surgical clip applier shown in FIG. 26A, showing further movement of the clip quantity actuator of FIG. 25 and the clip quantity indicator wheel of FIG. 24.

In use, the indicator wheel 74 is rotatably disposed within the housing 12, as shown in FIGS. 26A-26B, and the indicator actuator 76 is slidably disposed within the housing 12 such that the engagement mechanism 148 is positioned adjacent to the indicator wheel 74 and the protrusion 146 extends into the feed bar coupler 50. The housing 12 includes a window 12a formed therein for providing visual access to the indicator wheel 144. As the trigger 16 is moved to the closed position and the feed bar coupler 50 is moved distally, the indicator actuator 76 will move distally with the feed bar 38 and feed bar coupler 50. As a result, the engagement mechanism 148 on the indicator actuator 76 will engage the teeth 142 on the indicator wheel 74, thereby causing the wheel 74 to rotate as a clip is advanced into the jaws 20. Each time the trigger 16 is actuated to advance a clip 20 into the jaws 20, the indicator actuator 74 rotates the indicator wheel 76. When the clip supply has two or three clips left, the contrasting color pad 144 on the indicator wheel 74 will begin to appear in the window 12a formed in the housing 12, thereby indicating to the user that only a few clips remain. The contrasting color pad 144 can be adapted to occupy the entire window 12a when the clip supply is depleted.

In another exemplary embodiment, the indicator wheel 74 can include an anti-backup mechanism that is adapted to prevent the indicator wheel 74 from rotating in a reverse direction, e.g., a counter-clockwise direction, after being advanced. While the anti-backup mechanism can have a variety of configurations, in the embodiment shown in FIG. 24B the indicator wheel 74 includes opposed arms 73a, 73b that extend substantially parallel to the axis Y. Each arm 73a, 73b has a pawl 75a, 75b formed on a distal-most end thereof that is adapted to engage corresponding teeth formed on the housing 12. While not shown, the corresponding teeth can be formed within a circular protrusion formed on an inner portion of the housing 12 adjacent to the window 12a. When the indicator wheel 74 is disposed within the housing 12, the arms 73a, 73b extend into the circular protrusion formed around the inner circumference thereof. As a clip is applied and the indicator wheel 74 is rotated, the arms 73a, 73b can deflect over the teeth in the housing to move to the next position. When the indicator actuator 76 slides proximally to return to its initial position, the arms 73a, 73b will engage the teeth in the housing to prevent the indicator wheel 74 from rotating in a reverse direction, i.e., returning to the previous position. A person skilled in the art will appreciate that a variety of other techniques can be used to prevent backup of the indicator wheel 74.

As previously mentioned, the surgical clip applier 10 can be used to apply a partially or fully closed clip to a surgical site, such as a vessel, duct, shunt, etc. In laparoscopic and endoscopic surgery, a small incision is made in the patient's body to provide access to a surgical site. A cannula or access port is typically used to define a working channel extending from the skin incision to the surgical site. Often during surgical procedures it is necessary to cease blood flow through the vessels or other ducts, and some procedures may require the use of a shunt. A surgical clip can thus be used to crimp the vessel or to secure the shunt to the vessel. Accordingly, a surgical clip applier, such as clip applier 10, can be introduced through the cannula or otherwise introduced into the surgical site to position the jaws 20 around the vessel, shunt, or other duct. The tissue stop 46 can facilitate positioning of the jaws 20 around the target site. The trigger 16 can then be actuated to cause a clip to be advanced between the jaws and positioned around the target site, and to cause the jaws 20 to close to crimp the clip. Depending on the intended use of the clip, the trigger 16 can be partially actuated, as indicated by the audible sound of the pawl 60 reaching the tock tooth 112b, or it can be fully actuated. The trigger 16 is then released to release the partially or fully closed clip, and the procedure can be repeated if necessary to apply additional clips.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An improved endoscopic surgical clip applier having jaws which close together to approximate tissues to be clipped, and a push rod adapted to close the jaws, the improvement comprising:
a preloaded rotary joint formed between the push rod and a linkage coupled to the push rod, the preloaded rotary joint being effective to maintain the jaws in a substantially fixed partially closed position when a force applied to close the jaws is partially released during a closing stroke to retain a partially formed clip between the jaws, wherein the preloaded rotary joint includes a biasing element disposed in a recess that includes at least one ridge formed therein configured to maintain the biasing element at a substantially constant load during a closing stroke and up through full closure of the jaws.

2. The surgical clip applier of claim 1, wherein the preloaded rotary joint is adapted to maintain the push rod in a substantially fixed position while allowing the linkage to move proximally.

3. The surgical clip applier of claim 1, wherein the biasing element is adapted to be compressed by the push rod during a closing stroke, and adapted to apply a biasing force to the push rod when a force applied to close the jaws is at least partially released.

4. The surgical clip applier of claim 1, wherein the biasing element comprises a cantilevered beam.

5. The surgical clip applier of claim 1, wherein the biasing element comprises a spring.

6. The surgical clip applier of claim 3, wherein a proximal end of the push rod and the biasing element are disposed within the recess formed in a coupling mechanism, the biasing element biasing the proximal end of the push rod distally.

7. The surgical clip applier of claim 1, wherein the at least one ridge is adapted to prevent the biasing element from fully compressing.

8. A surgical clip applier, comprising:
a shaft;
jaws formed on a distal end of the shaft;
a jaw closing mechanism extending through the shaft and coupled to the jaws;
a preloaded joint associated with the jaw closing mechanism and being advanceable distally during a closing stroke, the preloaded joint being configured to prevent a clip from falling out of the jaws when a force applied to close the jaws is at least partially released during the closing stroke, and the preloaded joint including a biasing element disposed in a recess that includes at least one ridge formed therein configured to maintain the biasing element at a substantially constant load during a closing stroke and up through full closure of the jaws.

9. The surgical clip applier of claim 8, wherein the biasing element is adapted to be compressed by a portion of the jaw closing mechanism during a closing stroke.

10. The surgical clip applier of claim 9, wherein the biasing element is formed from Nitinol.

11. The surgical clip applier of claim 8, wherein the jaw closing mechanism includes a cam adapted to close the jaws and a push rod coupled to the cam.

12. The surgical clip applier of claim 11, wherein the recess is formed in a coupling mechanism and is adapted to be compressed by the push rod during a closing stroke.

13. The surgical clip applier of claim 8, wherein the at least one ridge is adapted to prevent the biasing element from fully compressing.

14. A surgical clip applier, comprising:
a shaft;
first and second jaws formed on a distal end of the shaft; and
an assembly coupled to the jaws and adapted to prevent clip fallout when a force applied to close the jaws is at least partially released during a closing stroke, the assembly including a recess and a biasing element formed in the recess, the recess including at least one ridge configured to prevent the biasing element from deflecting under compression during final stages of a closing stroke.

15. The surgical clip applier of claim 14, wherein the recess and the biasing element form a preloaded joint for maintaining a portion of the assembly in a fixed position and allowing a portion of the assembly to move proximally.

16. The surgical clip applier of claim 15, wherein the preloaded joint is formed between a push rod adapted to advance a cam over the jaws to close the jaws, and a coupling mechanism for coupling the push rod to an actuation mechanism for actuating the jaws, and wherein the preloaded joint maintains the push rod in a fixed position and allows the coupling mechanism to move proximally.

17. The surgical clip applier of claim 16, wherein the biasing element is disposed between the push rod and the coupling mechanism.

18. The surgical clip applier of claim 16, wherein the push rod is rotatably coupled to the coupling mechanism.

19. An improved endoscopic surgical clip applier having jaws which close together to approximate tissues to be clipped, and a push rod adapted to close the jaws, the improvement comprising:

a preloaded rotary joint formed between the push rod and a linkage coupled to the push rod, the preloaded rotary joint being effective to maintain the jaws in a substantially fixed partially closed position when a force applied to close the jaws is partially released during a closing stroke to retain a partially formed clip between the jaws, and the preloaded rotary joint including a biasing element being formed in a recess that includes at least one ridge formed therein and adapted to maintain the biasing element at a substantially constant load as the biasing element is compressed during a closing stroke.

* * * * *